US012630551B2

(12) United States Patent
Gu et al.

(10) Patent No.: US 12,630,551 B2
(45) Date of Patent: May 19, 2026

(54) ENDOCYCLIC PYRIMIDINONE COMPOUNDS, AND PREPARATION METHODS, COMPOSITIONS AND USE THEREOF

(71) Applicant: NEUSCO BIOTECH LIMITED, Shanghai (CN)

(72) Inventors: Zhenghua Gu, Shanghai (CN); Dongqin Wang, Shanghai (CN)

(73) Assignee: NEUSCO BIOTECH LIMITED, Shanghai (CN)

(*) Notice: Subject to any disclaimer, the term of this patent is extended or adjusted under 35 U.S.C. 154(b) by 693 days.

(21) Appl. No.: 17/998,569

(22) PCT Filed: May 12, 2021

(86) PCT No.: PCT/CN2021/093437

§ 371 (c)(1),
(2) Date: Nov. 11, 2022

(87) PCT Pub. No.: WO2021/228159

PCT Pub. Date: Nov. 18, 2021

(65) Prior Publication Data

US 2023/0212168 A1 Jul. 6, 2023

(30) Foreign Application Priority Data

May 13, 2020 (CN) ......................... 202010402611.4
Jul. 20, 2020 (CN) ......................... 202010700049.3

(51) Int. Cl.
*C07D 471/18* (2006.01)
*C07D 498/18* (2006.01)

(52) U.S. Cl.
CPC ......... *C07D 471/18* (2013.01); *C07D 498/18* (2013.01)

(58) Field of Classification Search
CPC .................................................... C07D 471/18
See application file for complete search history.

(56) References Cited

FOREIGN PATENT DOCUMENTS

| | | | |
|---|---|---|---|
| CN | 103827116 | A | 5/2014 |
| CN | 103827118 | A | 5/2014 |
| CN | 106536521 | A | 3/2017 |
| CN | 106536525 | A | 3/2017 |
| WO | 2013014185 | A1 | 1/2013 |
| WO | 2021/063145 | A1 | 4/2021 |

OTHER PUBLICATIONS

Nikolaou, A. "Small-molecule inhibitors as potential therapeutics and as tools to understand the role of phospholipases A2" BBA—Molecular and Cell Biology of Lipids 1864 (2019) 941-956.*

Bertilsson H, Tessem MB, Flatberg A, Viset T, Gribbestad I, Angelsen A, Halgunset J. Clin Cancer Res. 2012, 18, 3261-3269.*

Han "Diferential diagnosis of uncommon prostate diseases: combining mpMRI and clinical information" Han et al. Insights Imaging (2021) 12:79, 1-17.*

Campochiaro "The Complexity of Animal Model Generation for Complex Diseases" JAMA, Feb. 17, 2010—vol. 303, No. 7 657-658.*

Edwards et al. Molecular genetics of AMD and current animal models. Angiogenesis 2007 10:119-132.*

International Search Report issued in corresponding International Application No. PCT/CN2021/093437; mailed Aug. 20, 2021; 7 pgs.

First Office Action issued in corresponding Chinese Application No. 202010700049.3; mailed Mar. 8, 2022; 12 pgs.

Extended Search Report in Corresponding European Application No. 21803295.1, mailed May 15, 2024; 7 pgs.

Notice of Reasons for Refusal in Corresponding Japanese Application No. 2022-569274, mailed Jan. 16, 2024; 5 pgs.

Notice of Reasons for Refusal in Corresponding Japanese Application No. 2022-569274, mailed Jun. 25, 2024; 6 pgs.

Notice of Reasons for Rejection in Corresponding Korean Application No. 10-2022-7041660, dated Dec. 12, 2024; 12 pgs.

Notice of Reasons for Rejection in Corresponding Russian Application No. 2022129338/04, dated Mar. 12, 2024; 15 pgs.

Notice of Reasons for Rejection in Corresponding Russian Application No. 2022129338/04, dated Sep. 13, 2023; 20 pgs.

Notice of Reasons for Rejection in Corresponding Singapore Application No. 11202260172R, dated Mar. 26, 2025; 9 pgs.

* cited by examiner

*Primary Examiner* — David K O'Dell
(74) *Attorney, Agent, or Firm* — HAUPTMAN HAM, LLP

(57) ABSTRACT

Disclosed is an endocyclic pyrimidinone compound of Formula (I) or a pharmaceutically acceptable salt thereof, which is an entirely new Lp-PLA2 inhibitor useful in treating neurodegeneration-related diseases such as Alzheimer's disease (AD), glaucoma and age-related macular degeneration (AMD), or cardiovascular diseases including atherosclerosis.

10 Claims, No Drawings

ENDOCYCLIC PYRIMIDINONE COMPOUNDS, AND PREPARATION METHODS, COMPOSITIONS AND USE THEREOF

RELATED APPLICATIONS

The present application is a U.S. National Phase of International Application Number PCT/CN2021/093437, filed May 12, 2021, and claims priority to Chinese Application Numbers CN 202010402611.4, filed May 13, 2020, and CN 202010700049.3, filed Jul. 20, 2020.

TECHNICAL FIELD

The present disclosure relates to an endocyclic pyrimidinone compound, or a tautomer, meso isomer, racemate, enantiomer, diastereomer or mixture thereof, and to a preparation method, composition and medicinal use thereof. In particular, the present disclosure relates to an endocyclic pyrimidinone of Formula (I), a method of preparing it, and a pharmaceutical composition containing it, and to use of it as an LpPLA2 inhibitor in the treatment of neurodegenerative diseases such as Alzheimer's disease, glaucoma, and age-related macular degeneration (AMD), or the treatment of atherosclerosis and diabetic macular edema.

BACKGROUND

Lipoprotein-associated phospholipase A2 (Lp-PLA2) is a member of the phospholipase A2 superfamily (Dennis E A, Cao J, Hsu Y H, Magrioti V, Kokotos G. Chem Rev. 2011, 111, 6130-6185). It is mainly secreted by monocytes, macrophages, T lymphocytes and chief cells (Stafforini D M, Elstad M R, McIntyre T M, Zimmerman G A, Prescott S M. J Biol Chem. 1990, 265:9682-9687; Nakajima K, Murakami M, Yanoshita R, Samejima Y, Karasawa K, Setaka M, Nojima S Kudo I. J Biol Chem. 1997, 272, 19708-19713). Phosphatidylcholine sn-2 ester is produced during the oxidation of low density lipoprotein (LDL); Lp-PLA2 is responsible for the hydrolysis of oxidized phosphatidylcholine sn-2 ester, which then produces oxidized fatty acids and lysophosphatidylcholine (LysoPC) (Caslake M J, Packard C J, Suckling K E, Holmes S D, Chamberlain P, Macphee C H. Atherosclerosis. 2000, 150, 413-419; MacPhee C H, Moores K E, Boyd H F, Dhanak D, Ife R J, Leach C A, Leake D S, Milliner K J, Patterson R A, Suckling K E, Tew D G, Hickey D M. Biochem J. 1999, 338, 479-487). Both oxidized fatty acids and LysoPC play roles in activating macrophages, increasing oxidative stress, affecting the function of T lymphocytes, and inducing inflammatory responses (Quinn M T, Parthasarathy S, Steinberg D. Proc Natl Acad Sci USA. 1988, 85, 2805-2809). LysoPCs have been reported to induce the release of multiple cytotoxic inflammatory cytokines (Shi, et al, Atherosclerosis, 2007, 191, 54-62). In addition, LysoPCs have also been involved in the activation of leukocytes, the induction of apoptosis, and the mediation of endothelial dysfunction (Wilensky et al, Current Opinion in Lipidology, 2009, 20, 415-420).

It has been reported that plasma level of Lp-PLA2 is associated with cardiovascular diseases (Fitzpatrick A L, Irizarry M C, Cushman M, Jenny N S, Chi G C, Koro C. *Atherosclerosis.* 2014, 235, 384-391), diabetic macular edema (DME) (Staurenghi G, Ye L, Magee M H, Danis R P, Wurzelmann J, Adamson P, Mclaughlin M M, Darapladib DMES G. *Ophthalmology.* 2015, 122, 990-996), and prostate cancer (Bertilsson H, Tessem M B, Flatberg A, Viset T, Gribbestad I, Angelsen A, Halgunset J. Clin Cancer Res. 2012, 18, 3261-3269).

Alzheimer's disease (AD) is a chronic neurodegenerative disease that results in decreased cognitive abilities, mood swings, irreversible memory loss, disorientation, speech impairment, and loss of self-protection (Hardy J, et al. *Science* 2002, 297, 353-356). Alzheimer's disease usually begins slowly and progressively worsens over time, which is the cause of 60% to 70% of dementia cases and affects about 6% of the population over 65 years old. AD patients gradually go away from family and society, rely increasingly on help, and eventually progress to death. AD is one of the most costly diseases in developed countries and also incurs high costs in other countries. Especially as aging becomes an important social problem, these costs will grow dramatically. Needless to say, AD is a complex disease involving multiple factors. Although the etiology of AD has not been fully elucidated, it is clear that several factors are involved in the development and progression of the disease, including aggregated tau protein and Aβ peptides, oxidative stress and neuroinflammation (Echeverria V, Yarkov A, Aliev G. *Prog Neurobiol.* 2016, 144, 142-157). The current research and development of AD medicaments is focused primarily on targets of Aβ amyloidosis and tau (Chiang K, Koo E H. *Annu Rev Pharmacol Toxicol.* 2014, 54, 381-405; Awasthi M, Singh S, Pandey V P, Dwivedi U N. *J Neurol Sci.* 2016, 361, 256-271). However, despite the strong preclinical data, the results of later clinical trials have not demonstrated clinical efficacy to date. These disappointing results predict that other neuropathological mechanisms such as oxidative stress and neuroinflammation may have to be explored for AD treatment.

Elevated levels of Lp-PLA2 in plasma increase the risk of dementia, including AD (Van Oijen, et al. Annals of Neurology, 2006, 59,139). In addition to vascular dementia and mixed dementia, high oxidized LDL levels have been found in AD patients (Maher-Edwards G, De'Ath J, Barnett C, Lavrov A, Lockhart A, Alzheimer's & Dementia: Translational Research & Clinical Interventions. 2015, 1, 131-140; Kassner et al. Current Alzheimer Research, 2008, 5, 358-366; Dildar, et al., Alzheimer Dis Assoc Disord, 24, April-June (2010); Sinem, et al. Current Alzheimer Research, 2010, 7, 463-469). Neuroinflammation and upregulation of multiple inflammatory cytokines have also been found in AD patients (Colangelo, et al., Journal of Neuroscience Research, 2002, 70, 462-473; Wyss-Coray, Nature Medicine, 2006, 12, September).

Based on all these findings, Lp-PLA2 is a potential target for the treatment of AD, and this is further confirmed by the clinical results of the Lp-PLA2 inhibitor Rilapladib for AD patients (Maher-Edwards G, De'Ath J, Barnett C, Lavrov A, Lockhart A, *Alzheimer's & Dementia: Translational Research & Clinical Interventions.* 2015, 1, 131-140).

Glaucoma and age-related macular degeneration (AMD) are among retinal neurodegenerative diseases. Buschini et al reported that inflammation, including TNF-α signaling, may play an important role in the pathogenesis of glaucoma and AMD (Buschini et al, Progress in Neurobiology, 2011, 95, 14-25; Tezel, Progress in Brain Research, vol. 173, ISSN0079-6123, Chapter 28). Additionally, Shi et al demonstrated that Lp-PLA2 inhibitors can block the release of inflammatory cytokines (Shi, et al, Atherosclerosis, 2007, 191, 54-62). Inhibition of Lp-PLA2 is potential therapy for glaucoma and AMD.

A number of Lp-PLA2 inhibitors have been reported, including β-lactams (Tew D G, Boyd H F, Ashman S, Theobald C, Leach C A. Biochemistry. 1998, 37, 10087-10093), oximes (Jeong T S, Kim M J, Yu H, Kim H S, Choi J K, Kim S S, Lee W S. Bioorg Med Chem Lett. 2005, 15, 1525-1527; Jeong H J, Park Y D, Park H Y, Jeong I Y, Jeong T S, Lee W S. Bioorg Med Chem Lett. 2006, 16, 5576-5579), amides of xanthuric acid (Lin E C, Hu Y, Amantea C M, Pham L M, Cajica J, Okerberg E, Brown H E, Fraser A, Du L, Kohno Y, Ishiyama J, Kozarich J W, Shreder K R. Bioorg Med Chem Lett. 2012, 22, 868-871; Hu Y, Lin E C, Pham L M, Cajica J, Amantea C M, Okerberg E, Brown H E, Fraser A, Du L, Kohno Y, Ishiyama J, Kozarich J W, Shreder K R. Bioorg Med Chem Lett. 2013, 23, 1553-1556), and carbamates (Nagano J M, Hsu K L, Whitby L R, Niphakis M J, Speers A E, Brown S J, Spicer T, Fernandez-Vega V, Ferguson J, Hodder P, Srinivasan P, Gonzalez T D, Rosen H, Bahnson B J, Cravatt B F. Bioorg Med Chem Lett. 2013, 23, 839-843).

The Lp-PLA2 inhibitor Darapladib has been reported to be potential therapy for atherosclerosis and DME (Magrioti V, Kokotos G. *Expert Opin Ther Pat.* 2013; 23:333-344).

SUMMARY

The present inventors have found that Lp-PLA2 inhibitors play an important role in the treatment of neurodegeneration-related diseases such as Alzheimer's disease (AD), glaucoma and age-related macular degeneration (AMD), or cardiovascular diseases including atherosclerosis and the like. Thus, the present inventors have endeavored to develop an entirely new Lp-PLA2 inhibitor: an endocyclic pyrimidinone compound.

The endocyclic pyrimidinone compound is a compound having a structure represented by Formula (I) or a pharmaceutically acceptable salt thereof, (I)

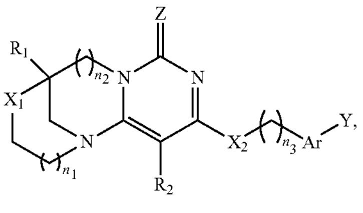

wherein

- $n_1$, $n_2$, and $n_3$ are each independently 0, 1, or 2;
- $R_1$ and $R_2$ are each independently selected from —H, hydroxyl, cyano, halogen, alkyl, deuterated alkyl, deuterated alkoxy, hydroxyalkyl, haloalkyl, haloalkoxy, cycloalkyl, alkoxy, arylene, or heteroarylene;
- $X_1$ and $X_2$ are each independently selected from alkylene, —O—, —S—, or —NR'—,
- R' is selected from —H, alkyl, deuterated alkyl, or cycloalkyl;
- Ar is arylene or heteroarylene, wherein hydrogen atoms in the arylene or heteroarylene are optionally substituted with one or more substituents, and the substituents are each independently selected from halogen, alkyl, deuteroalkyl, haloalkyl, alkoxy, deuteroalkoxy, haloalkoxy, hydroxy, hydroxyalkyl, cyano, amino, monoalkyl- or dialkyl-substituted amino, nitro, carboxy, formyl, cycloalkyl, heterocyclyl, aryl, or heteroaryl;
- Y is —H, halogen, alkyl, haloalkyl, haloalkoxy, cycloalkyl, alkoxy, deuterated alkyl, deuterated alkoxy, hydroxy, hydroxyalkyl, cyano, arylene, heteroarylene, —OAr', —SAr', —NR"—Ar', —NR"R", or —R'"—Ar';
- Ar' is selected from aryl or heteroaryl, wherein hydrogen atoms in the aryl or heteroaryl are optionally substituted with one or more substituents, the substituents are each independently selected from halogen, alkyl, haloalkyl, alkoxy, hydroxy, hydroxyalkyl, haloalkoxy, deuterated alkyl, deuterated alkoxy, cyano, amino, nitro, carboxy, formyl, cycloalkyl, heterocyclyl, aryl, or heteroaryl;
- R" is H—, alkyl, or cycloalkyl;
- R'" is alkylene;
- Z is O or S.

Optionally, halogens in the "halogen" "haloalkyl" and "haloalkoxy" are each independently selected from F, Cl, Br, or I;

- optionally, alkyls in the "alkyl" "deuterated alkyl" "deuterated alkoxy" "hydroxyalkyl" "haloalkyl", "haloalkoxy" "alkoxy" and "mono- or di-alkyl substituted amino" are each independently $C_1$-$C_{10}$ linear or branched alkyl; optionally each independently $C_1$-$C_7$ linear or branched alkyl; optionally each independently $C_1$-$C_4$ linear or branched alkyl; and optionally selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl;
- optionally, "alkylenes" are each independently $C_1$-$C_{10}$ linear or branched alkylene; optionally each $C_1$-$C_7$ linear or branched alkylene; optionally each $C_1$-$C_5$ linear or branched alkylene; and optionally each selected from methylene, ethylene, n-propylene, isopropylene, n-butylene, iso-butylene, tert-butylene, sec-butylene, n-pentylene, 1-methylbutylene, 2-methylbutylene, 3-methylbutylene, isopentylene, 1-ethylpropylene, neopentylene, n-hexylene, 1-methylpentylene, 2-methylpentylene, 3-methylpentylene, isohexylene, 1,1-dimethylbutylene, 2,2-dimethylbutylene, 3,3-dimethylbutylene, 1,2-dimethylbutylene, 1,3-dimethylbutylene, 2,3-dimethylbutylene, 2-ethylbutylene, n-heptylene, 2-methylhexylene, 3-methylhexylene, 2,2-dimethylpentylene, 3,3-dimethylpentylene, 2,3-dimethylpentylene, 2,4-dimethylpentylene, 3-ethylpentylene, or 2,2,3-trimethylbutylene;
- optionally, "cycloalkyl" is $C_3$-$C_{10}$ monocyclic or bicyclic cycloalkyl, optionally $C_3$-$C_7$ monocyclic cycloalkyl, and optionally cyclopropyl, cyclobutyl, cyclopentyl, cyclohexyl, or cycloheptyl;
- optionally, "heterocyclyl" is 3- to 10-membered non-aromatic heterocycle having in the ring 1, 2, or 3 heteroatoms selected from N, O, and S; optionally 3- to 10-membered non-aromatic ring having in the ring 1 or 2 heteroatoms selected from N and O; optionally 3- to 6-membered non-aromatic ring having in the ring 1 or 2 heteroatoms selected from N and O; optionally 3- to 10-membered non-aromatic ring having in the ring 1 or 2 heteroatoms selected from N and S; and optionally 3- to 6-membered non-aromatic ring having in the ring 1 or 2 heteroatoms selected from N and S;

optionally, "aryl" is 6- to 10-membered aryl; optionally phenyl or naphthyl, and optionally phenyl, 1-naphthyl, or 2-naphthyl;

optionally, "arylene" is 6- to 10-membered arylene; and optionally phenylene or naphthylene;

optionally, "heteroaryl" is 5- to 10-membered heteroaryl ring having in the ring 1-3 heteroatoms selected from N, O, and S; optionally 5- to 10-membered heteroaryl ring having in the ring 1-2 heteroatoms selected from N, O, and S; optionally the heteroaryl ring is selected from pyridine ring, pyrrole ring, pyrazole ring, pyrimidine ring, pyrazine ring, pyridazine ring, thiophene ring, and furan ring; optionally selected from pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, pyrazin-3-yl, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinoxalinyl, thieno[2,3-b]furanyl, furo[3,2-b]-pyranyl, pyrido[2,3-d]oxazinyl, pyrazolo[4,3-d]oxazolyl, imidazo[4,5-d]thiazolyl, pyrazino[2,3-d]pyridazinyl, imidazo[2,1-b]thiazolyl, imidazo[1,2-b][1,2,4]triazinyl, benzothienyl, benzoxazolyl, benzimidazolyl, benzothiazolyl, benzoxepinyl, benzoxazinyl, benzofuranyl, benzotriazolyl, pyrrolo[2,3-b]pyridyl, pyrrolo[3,2-c]pyridinyl, pyrrolo[3,2-b]pyridyl, imidazo[4,5-b]pyridyl, imidazo[4,5-c]pyridyl, pyrazolo[4,3-d]pyridyl, pyrazolo[4,3-c]pyridyl, pyrazolo[3,4-c]pyridinyl, pyrazolo[3,4-d]pyridyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazolo[2,3-b]pyrazinyl, or pyrimido[4,5-d]pyrimidinyl; and is optionally selected from pyridin-2-yl, pyridin-3-yl, pyridin-4-yl, pyrimidin-2-yl, pyrimidin-4-yl, or pyrimidin-5-yl;

optionally, "heteroarylene" is 5- to 10-membered heteroarylene ring having in the ring 1-3 heteroatoms selected from N, O, and S; optionally 5- to 10-membered heteroaromatic ring having in the ring 1-2 heteroatoms selected from N, O, and S; and optionally the heteroarylene ring is selected from pyridinylene ring, pyrrolylene ring, pyrazolylene ring, pyrimidinylene ring, pyrazine ring, pyridazine ring, thiophene ring, or furanylene ring.

Optionally, the compound of Formula (I) is in the form of a tautomer, meso isomer, racemate, enantiomer, diastereomer, or mixture thereof.

Optionally, $n_1$, $n_2$, and $n_3$ are each independently 0, 1, or 2.

Optionally, $n_1$ is 1.

Optionally, $n_2$ is 1.

Optionally, $n_3$ is 1.

Optionally, $R_1$ and $R_2$ are each independently selected from —H, fluorine, chlorine, bromine, iodine, hydroxyl, hydroxyalkyl, cyano, $C_1$-$C_7$ alkyl (such as methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), $C_1$-$C_3$ deuteroalkyl (such as —$CD_3$, —$C_2D_5$, or —$C_3D_7$), $C_1$-$C_3$ deuteroalkoxy (such as —$OCD_3$, —$OC_2D_5$, or —$OC_3D_7$), $C_1$-$C_3$ haloalkyl (such as —$CF_3$, —$CHF_2$, —$CH_2F$, —$C_2F_5$, or —$C_3F_7$), $C_1$-$C_7$ haloalkoxy, $C_1$-$C_7$ alkoxy, cyclopropanyl, cyclobutanyl, cyclopentanyl, or cyclohexanyl; optionally, $R_1$ is —H; and optionally, $R_2$ is —H;

optionally, $X_1$ and $X_2$ are each independently selected from $C_1$-$C_7$ alkylene, —O—, —S—, or —NR'—; optionally, $X_1$ is $C_1$-$C_7$ alkylene (optionally, —$CH_2$—, ethylene, n-propylene, isopropylene, n-butylene, or isobutylene), —O—, or —S—; optionally, $X_1$ is $C_1$-$C_7$ alkylene or —O—; optionally, $X_1$ is —$CH_2$— or —O—; optionally, $X_2$ is —O— or —S—; and optionally, $X_2$ is —O—;

optionally, R' is selected from —H, $C_1$-$C_7$ alkyl (optionally, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), deuterated alkyl (optionally, —$CD_3$, —$C_2D_5$, or —$C_3D_7$), or $C_3$-$C_6$ cycloalkyl (optionally, cyclopropanyl, cyclobutanyl, cyclopentanyl, or cyclohexanyl);

optionally, Ar is phenylene or pyridyl, wherein hydrogen atoms in the phenylene or pyridyl are optionally substituted with 1, 2, or 3 substituents, the substituents are each independently selected from F, Cl, Br, I, —CN, -Me, —$CF_3$, —$CHF_2$, —$C_2H_5$, —$C_3H_7$, cyclopropyl, cyclobutyl, cyclopentyl, cyclohexyl, —$CD_3$, —$OCD_3$, —Ome, —$OCF_3$, or —$OCHF_2$;

optionally, Ar is arylene; and optionally, Ar is phenylene, wherein hydrogens in the phenylene are optionally substituted with one or two substituents, the substituents are halogen, and optionally F;

optionally, Y is —H, —F, —Cl, —Br, —I, methyl, ethyl, n-propyl, isopropyl, —$CD_3$, —$OCD_3$, —$CF_3$, —$CHF_2$, —$CH_2F$, —$CH_2CF_3$, —$OCF_3$, —$OCHF_2$, —$OCH_2F$, cyclopropyl, cyclobutyl, cyclopentyl, cyclohexyl, —$OCH_3$, —$OC_2H_5$, —$OC_3H_7$, or —OAr';

optionally, Y is H, halogen, or —OAr'; and optionally, Y is H, —F, or —OAr';

optionally, Ar' is selected from phenyl, pyridyl, pyrimidinyl, thienyl, pyrrolyl, pyrazolyl, or quinolinyl, wherein hydrogen atoms in the phenyl, pyridyl, pyrimidinyl, thienyl, pyrrolyl, pyrazolyl, or quinolinyl ring are each independently optionally substituted with 1, 2, or 3 substituents, the substituents are each independently selected from F, Cl, Br, —CN, $C_1$-$C_7$ alkyl (optionally, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl), —$CD_3$, —$OCD_3$, $C_1$-$C_6$ haloalkyl, —$OCH_3$, —$OC_2H_7$, —$OC_3H_7$, $C_1$-$C_6$ haloalkoxy, hydroxyl, hydroxyalkyl, cyano, or $C_3$-$C_6$ cycloalkyl (optionally, cyclopropanyl, cyclobutanyl, cyclopentanyl, or cyclohexanyl);

optionally, Ar' is selected from phenyl, pyridin-3-yl, pyridin-4-yl, or pyrimidin-5-yl, and is optionally substituted with 1 or 2 substituents, the substituents are selected from halogen, alkyl, haloalkyl, or haloalkoxy, and optionally selected from F, Cl, $—CH_3$, $—CF_3$, or $—OCF_3$;

optionally, Z is O or S; and optionally, Z is O.

Optionally, of a compound of Formula (I) or a pharmaceutically acceptable salt thereof, the compound of Formula (I) is selected from the following compounds:

1

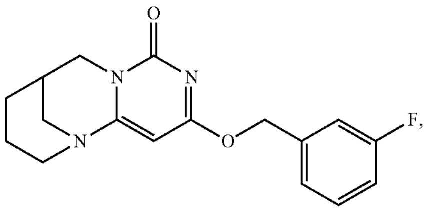

2

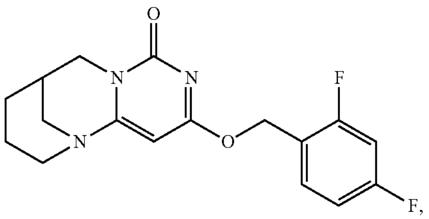

3

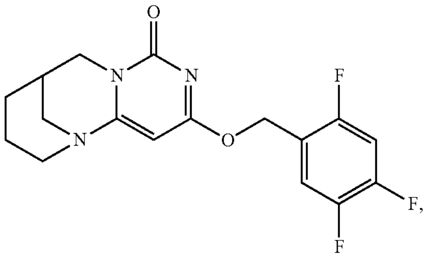

4

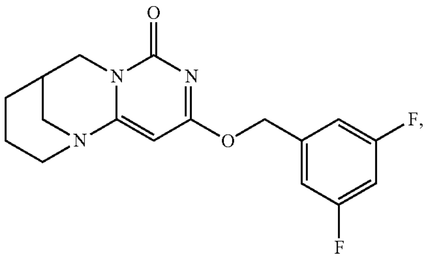

5

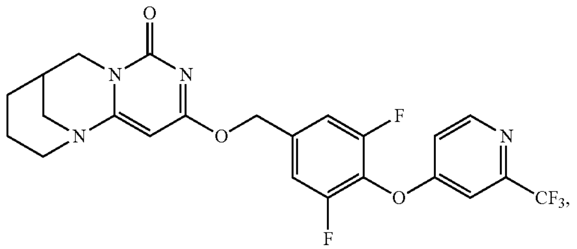

-continued

6

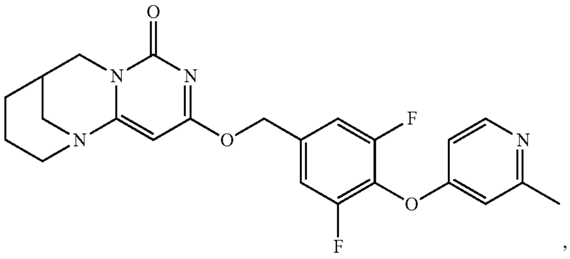

7

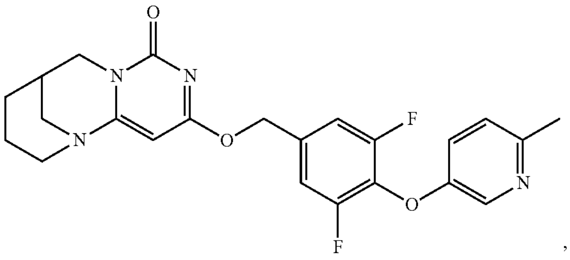

8

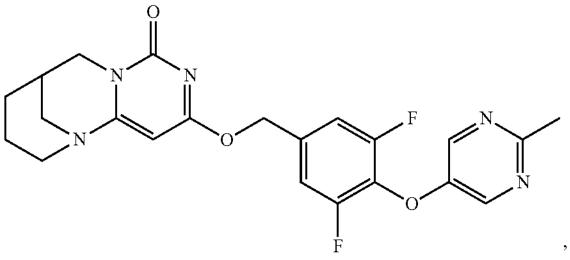

9

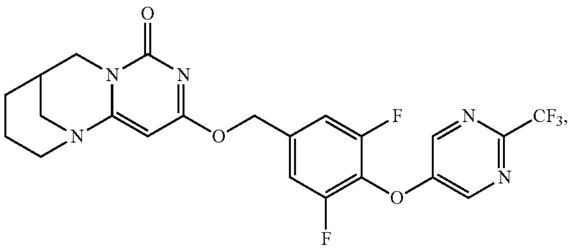

10

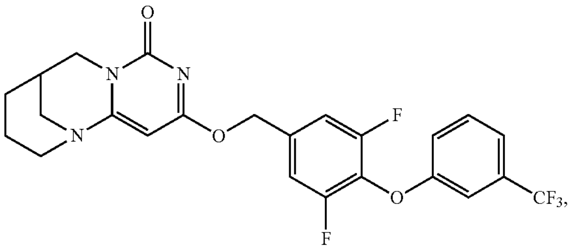

-continued
11
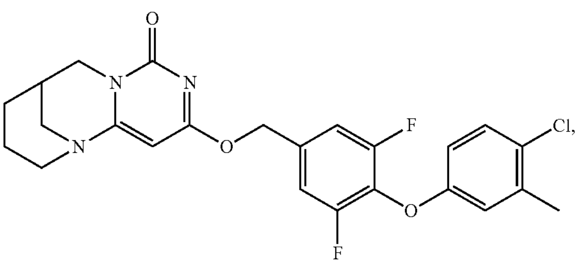
12
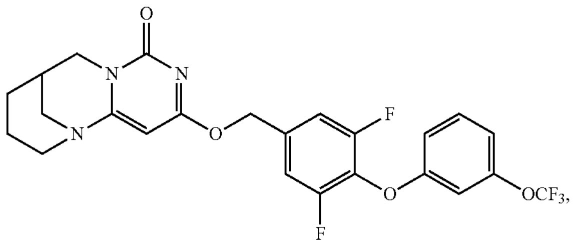
13
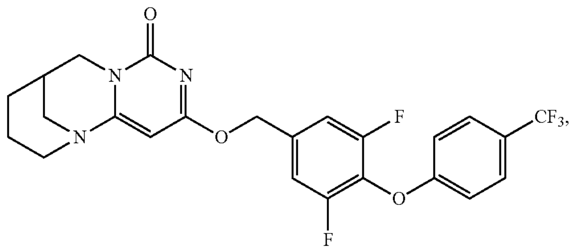
14
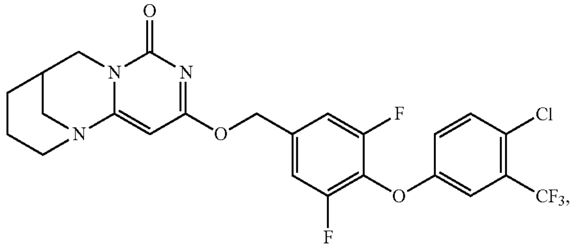
15
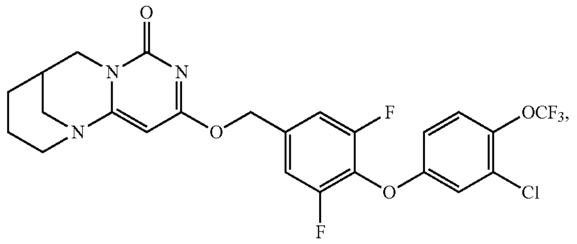
16
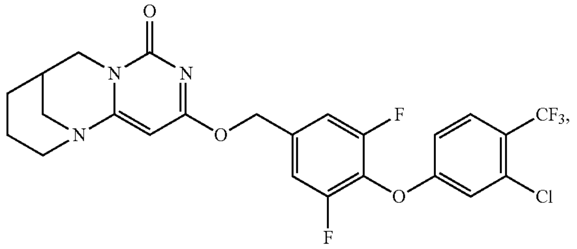
-continued
17
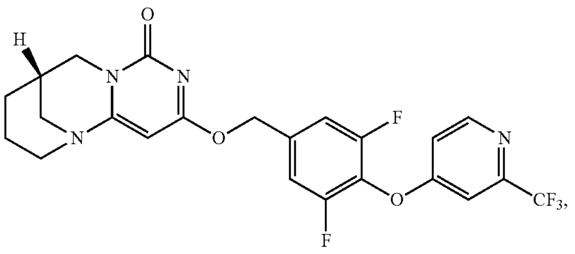
18
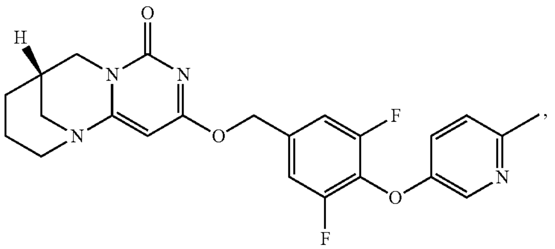
19
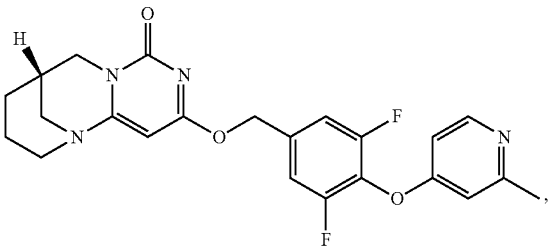
20
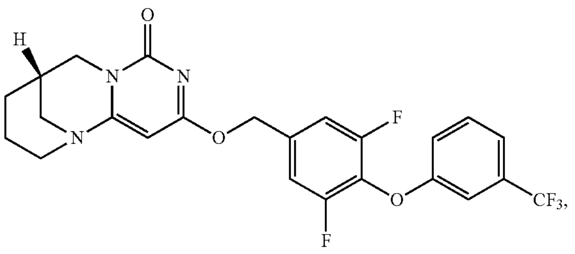
21
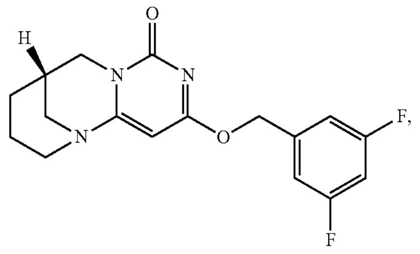
22
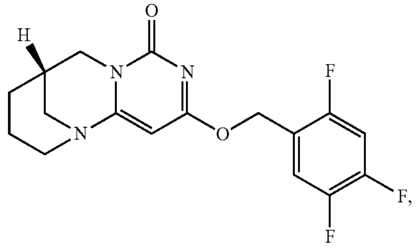

23
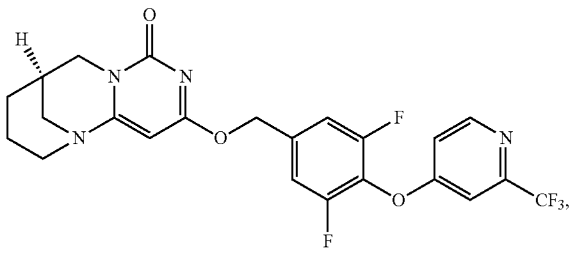
24
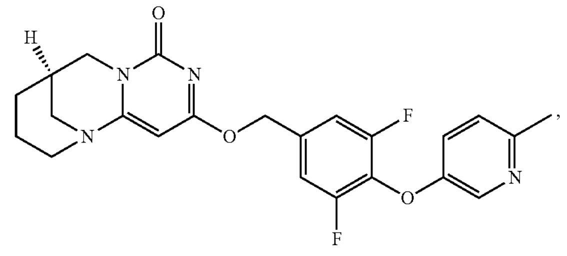
25
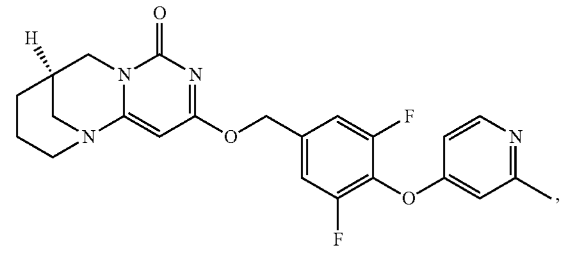
26
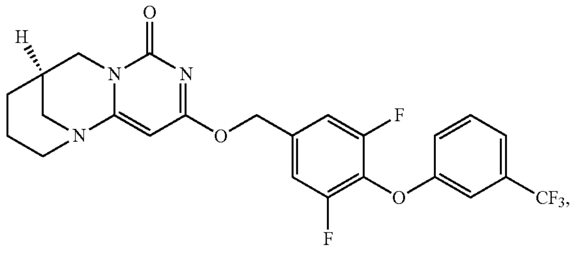
27
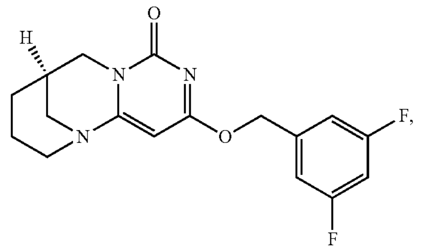
28
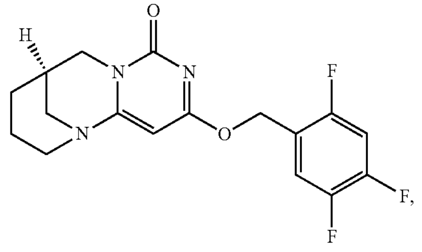
29
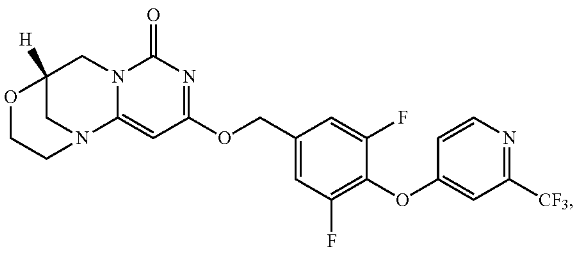
30
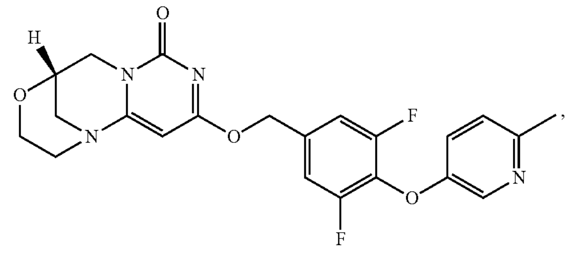
31
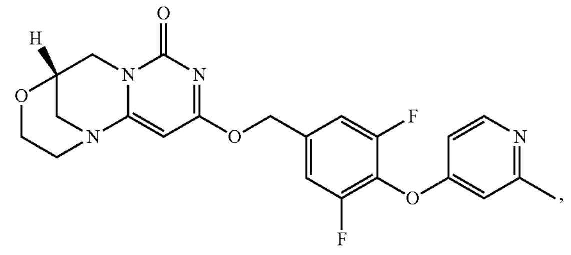
32
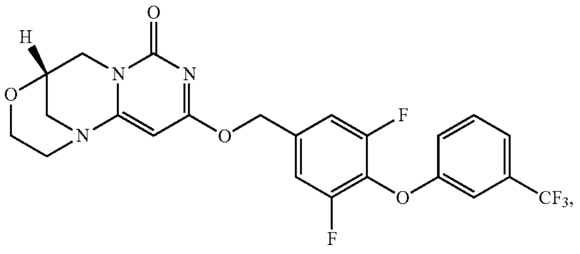
33
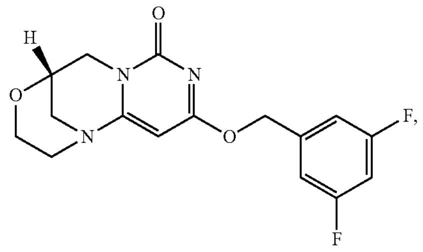
34
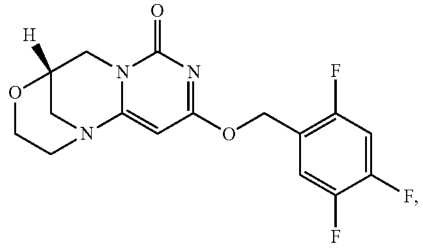

-continued

35

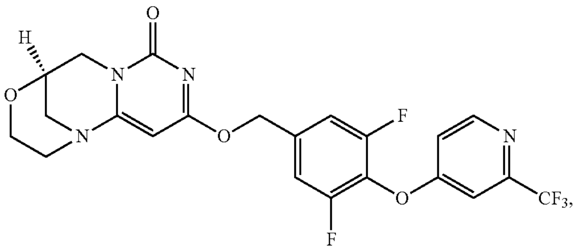

36

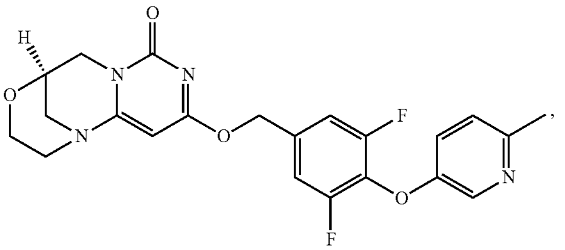

37

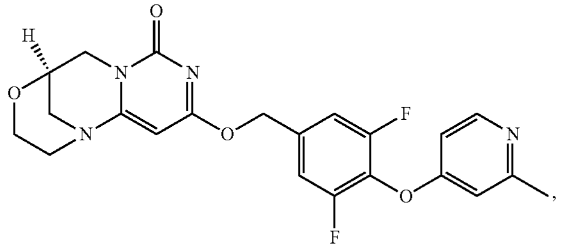

38

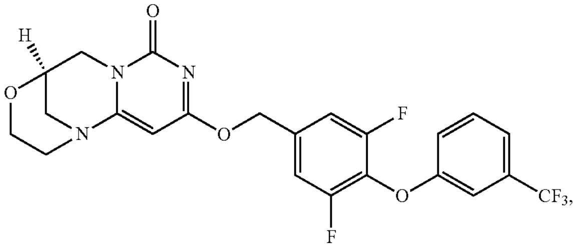

39

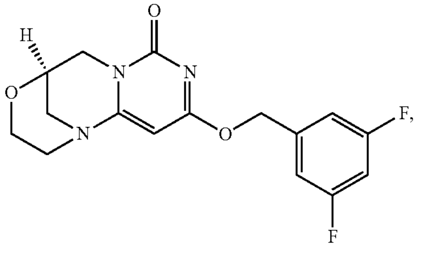

40

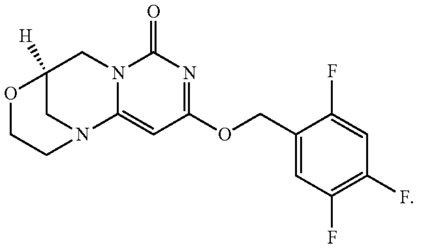

Optionally, of the compound of Formula (I) or a pharmaceutically acceptable salt thereof, the pharmaceutically acceptable salt includes an anionic salt or cationic salt of the compound of Formula (I);

optionally, the pharmaceutically acceptable salt includes alkali metal salt, alkaline earth metal salt, or ammonium salt of the compound of Formula (I); optionally, the alkali metal includes sodium, potassium, lithium, or cesium, and the alkaline earth metal includes magnesium, calcium, or strontium;

optionally, the pharmaceutically acceptable salt includes salt formed by the compound of Formula (I) and an organic base;

optionally, the organic base includes trialkylamine, pyridine, quinoline, piperidine, imidazole, picoline, dimethylaminopyridine, dimethylaniline, N-alkylmorpholine, 1,5-diazabicyclo[4.3.0]nonene-5, 1,8-diazabicyclo[5.4.0]undecene-7, 1,4-diazabicyclo[2.2.2] octane; optionally, the trialkylamine includes trimethylamine, triethylamine, or N-ethyldiisopropylamine; and optionally, the N-alkyl morpholine includes N-methylmorpholine;

optionally, the pharmaceutically acceptable salt includes a salt formed by the compound of Formula (I) and an acid;

optionally, the acid includes inorganic acid, or organic acid; optionally, the inorganic acid includes hydrochloric acid, hydrobromic acid, hydroiodic acid, sulfuric acid, nitric acid, phosphoric acid, or carbonic acid; optionally, the organic acid includes formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, or pamoic acid.

In another aspect, there is provided a preparation method of a compound of Formula (I) or a pharmaceutically acceptable salt thereof, comprising the step of reacting a compound of Formula (II) with a compound of Formula (III) to produce the compound of Formula (I):

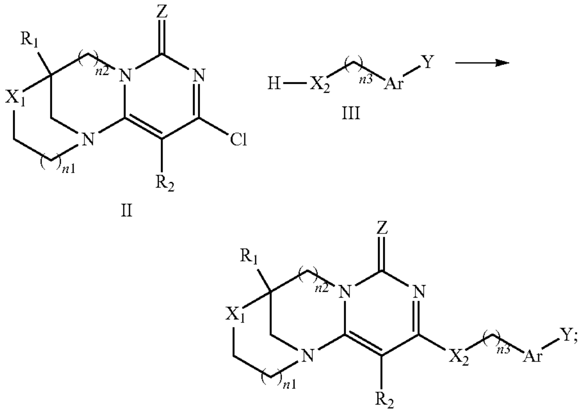

II

III

I optionally, the preparation method comprises the step of reacting a compound of Formula (IV) with phosphorus oxychloride to produce the compound of Formula (II):

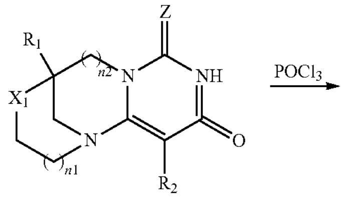

IV

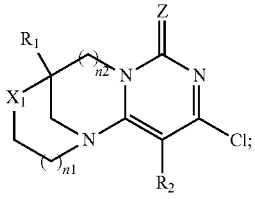

II optionally, the preparation method comprises the step of subjecting a compound of Formula (V) to cyclization reaction to produce the compound of Formula (IV):

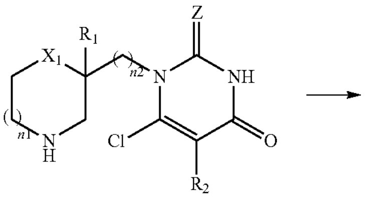

V

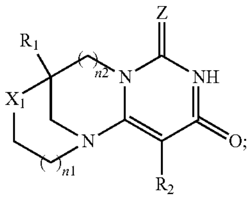

IV optionally, the preparation method comprises the step of reacting a compound of Formula (VII) with a compound of Formula (VIII) to produce a compound of Formula (VI), and further removing the protective group from the compound of Formula (VI) to produce the compound of Formula (V):

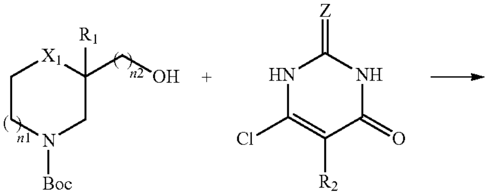

VII

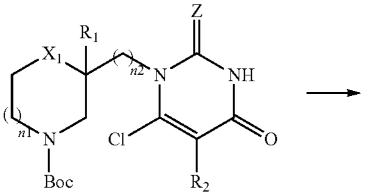

VI

-continued

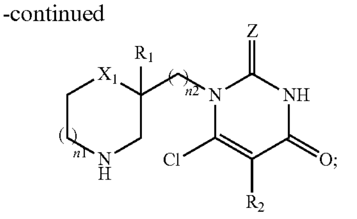

VI optionally, the preparation method includes the following reaction scheme:

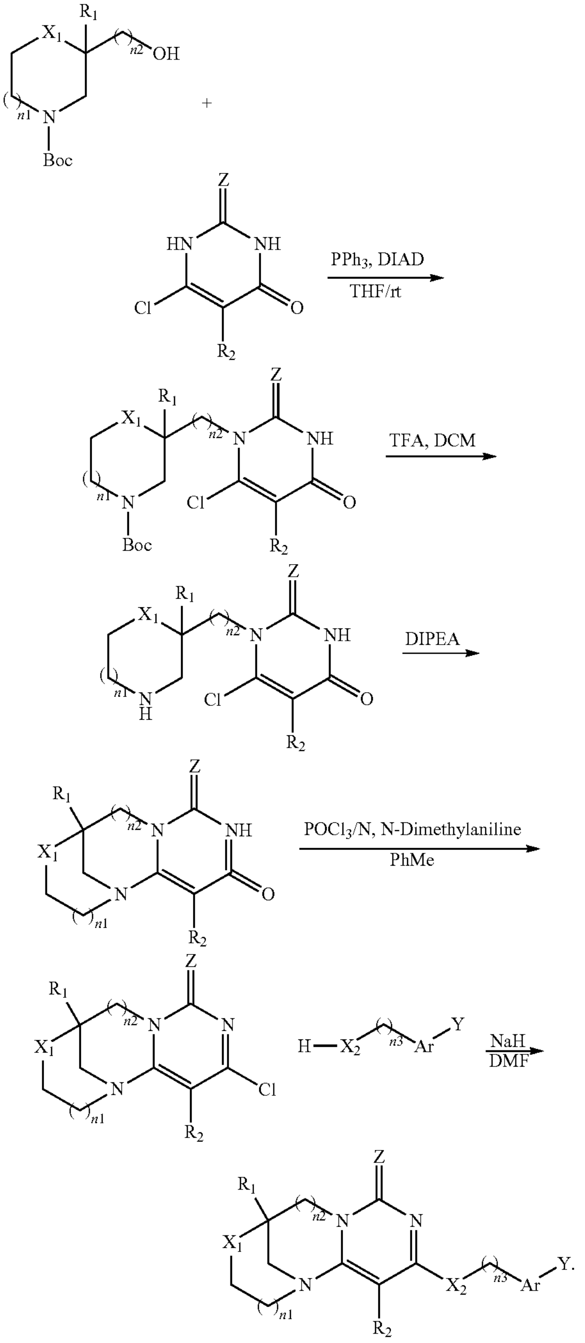

In each of the formulas in the preparation method described above, $n_1$, $n_2$, $n_3$, $R_1$, $R_2$, $X_1$, $X_2$, Z, Ar, and Y are defined as above.

No particular limitation is necessary for conditions under which each of the reactions described above is carried out, and they can be carried out under conventional conditions or by following conventional steps.

In another aspect, there is provided a pharmaceutical composition, comprising a therapeutically effective amount of one or more of the compound of Formula (I) or a pharmaceutically acceptable salt thereof, and optionally, a pharmaceutically acceptable excipient(s).

Optionally, the dosage form of the pharmaceutical composition includes oral, rectal, or parenteral formulation;

optionally, the oral formulation includes solid or liquid formulation;

optionally, the solid formulation includes tablet, powder, granule, or capsule;

optionally, the liquid formulation includes aqueous or oily suspension, or syrup;

optionally, the parenteral formulation includes solution for injection, or aqueous or oily suspension.

In another aspect, there is provided use of the compound of Formula (I) or a pharmaceutically acceptable salt thereof, or the pharmaceutical composition, in the preparation of an Lp-PLA2 inhibitor.

In another aspect, there is provided use of the compound of Formula (I) or a pharmaceutically acceptable salt thereof, or the pharmaceutical composition, in the preparation of a medicament for treatment of neurodegeneration-related diseases;

optionally, the neurodegeneration-related diseases include Alzheimer's disease (AD), glaucoma, and age-related macular degeneration (AMD).

In another aspect, there is provided use of the compound of Formula (I) or a pharmaceutically acceptable salt thereof, or the pharmaceutical composition, in the preparation of a medicament for the treatment of cardiovascular diseases, diabetic macular edema (DME), or prostate diseases;

optionally, the cardiovascular diseases include atherosclerosis.

Beneficial effects of the present disclosure are as follows:

The compound of Formula (I) or a pharmaceutically acceptable salt thereof is an endocyclic pyrimidinone compound as well as an entirely novel Lp-PLA2 inhibitor. It is useful in treating neurodegeneration-related diseases such as Alzheimer's disease (AD), glaucoma and age-related macular degeneration (AMD), or cardiovascular diseases including atherosclerosis and the like, diabetic macular edema (DME), or prostate diseases and the like.

DETAILED DESCRIPTION

The present disclosure is further illustrated by means of examples that will be described later. It should be appreciated that the examples are for illustrative purposes only and not intended to limit the scope of the present invention in any way.

The starting materials of the present invention can be synthesized by a method known in the art, or be purchased from ABCR GmbH & Co. KG, Acros Organics, Aldrich Chemical Company, Accela ChemBio Inc., and Darry Chemicals, among other companies.

Unless otherwise specified, the solution in the examples refers to an aqueous solution.

Unless otherwise specified, the temperature in the examples at which the reaction is carried out is room temperature, e.g., 20° C. to 30° C.

Example 1 Preparation of Compound 1

1

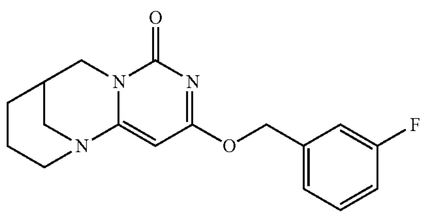

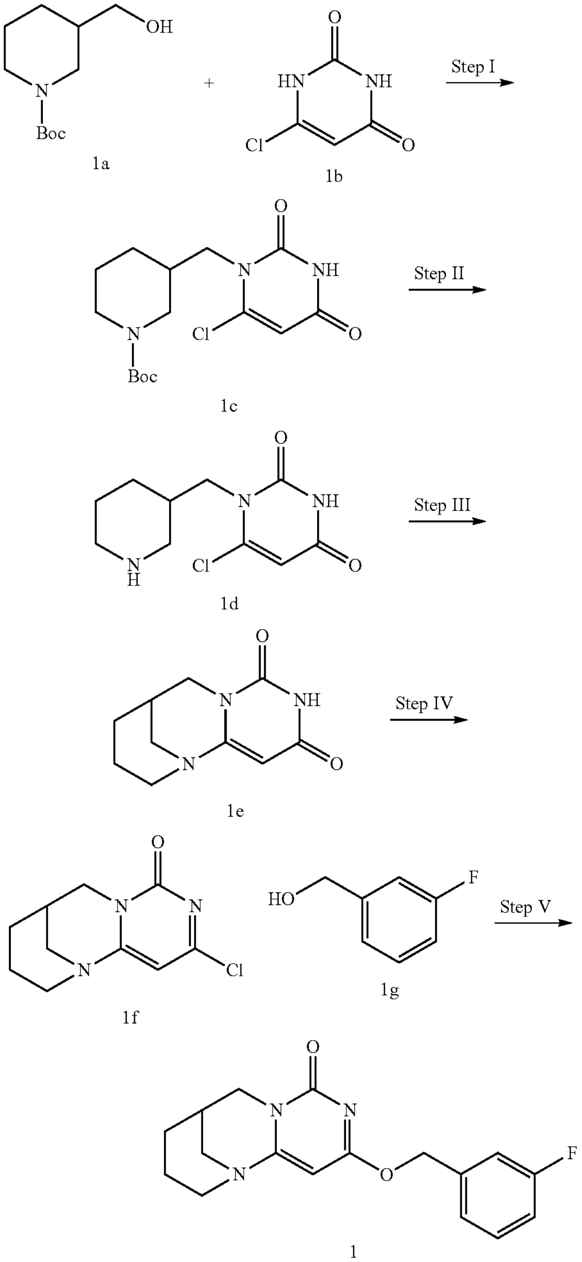

Step I: Preparation of Compound 1c

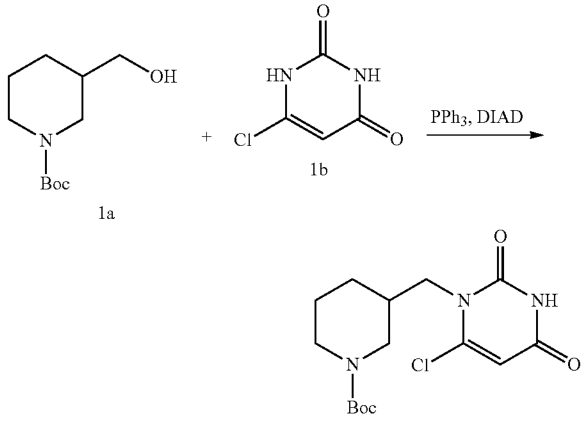

1a 1b 1c

To a solution of 6-chlorouracil 1b (8.5 g, 58.0 mmol), tert-butyl 3-(hydroxymethyl)piperidine-1-carboxylate 1a (15 g, 69.6 mmol) and triphenylphosphine (22.8 g, 86.9 mmol) dissolved in a mixed solvent of anhydrous tetrahydrofuran (250 mL) and N,N-dimethylformamide (25 mL) at room temperature, was added dropwise diisopropyl azodicarboxylate (23 ml, 115.8 mmol) under nitrogen at 0° C. The reaction mixture was stirred at 0° C. for 2 h, then warmed to room temperature and stirred overnight. The reaction mixture was filtered and extracted with ethyl acetate (50 mL×3). The combined organic phases were dried over anhydrous sodium sulfate, the desiccant was filtered out and the filtrate was concentrated under reduced pressure. Purification on a silica gel column with $CH_2Cl_2/CH_3OH$ (20/1) afforded the title compound 1c (8.34 g, yield: 41.8%) as a colorless oil.

Steps II and III: Preparation of Compound 1e

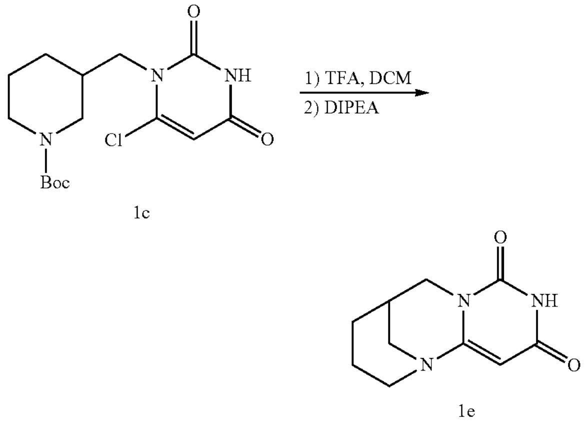

1c 1e

To a solution of tert-butyl 3-((6-chloro-2,4-dioxo-3,4-dihydropyrimidin-1(2H)-yl)methyl)piperidine-1-carboxylate 1c (8.34 g, 24.3 mmol) dissolved in dichloromethane (80 mL) at room temperature, was added trifluoroacetic acid (20 mL) at 0° C. The reaction mixture was stirred at room temperature for 2 h, and concentrated under reduced pressure. The afforded residue was used directly in the next step, and was dissolved in acetonitrile (100 mL), then diisopropylethylamine (9.3 g, 72.9 mmol) was added at room temperature. The reaction mixture was stirred for 4 h, and concentrated under reduced pressure, followed by purification on a silica gel column $CH_2Cl_2/CH_3OH$ (20/1) to afford the title compound 1e (4.7 g, 93.3%) as a white solid.

$^1H$ NMR (400 MHz, DMSO) δ 11.01 (s, 1H), 5.09 (s, 1H), 3.84 (m, 1H), 3.51 (m, 1H), 3.30 (m, 1H), 3.16 (m, 1H), 3.04 (m, 1H), 2.94 (m, 1H), 2.25 (m, 1H), 1.89-1.68 (m, 2H), 1.61-1.46 (m, 1H), 1.36 (m, 1H).

Step IV: Preparation of Compound 1f

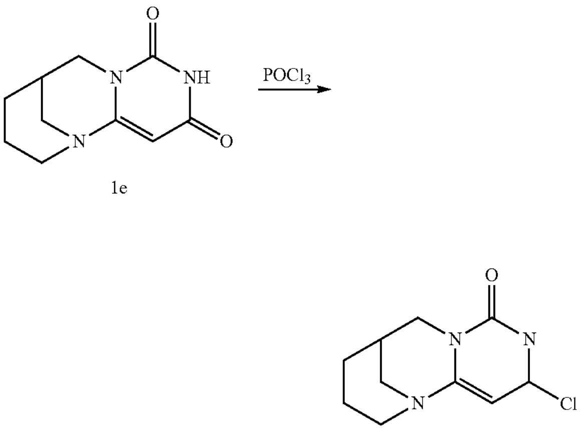

1e 1f

To a solution of compound 1e (2.0 g, 9.7 mmol) and dimethylaniline (2.34 g, 19.3 mmol) in toluene, was added phosphorous oxychloride (1.48 g, 9.7 mmol) dropwise at room temperature. The reaction mixture was heated to reflux for 4 h, quenched with ice water, and concentrated under reduced pressure. The residue was extracted with ethyl acetate (60 mL×3). The combined organic phases were washed with a saturated aqueous solution of sodium chloride, dried over anhydrous sodium sulfate, the desiccant was filtered out and the filtrate was concentrated under reduced pressure. Purification on a silica gel column with $CH_2Cl_2/CH_3OH$ (20/1) afforded the title compound 1f (0.89 g, 40.7%) as a white solid.

$^1H$ NMR (400 MHz, $CDCl_3$) δ 6.06 (s, 1H), 4.06 (m, 1H), 3.77 (m, 1H), 3.52 (m, 1H), 3.29 (m, 1H), 3.22-3.15 (m, 1H), 3.02 (m, 1H), 2.52 (m, 1H), 2.01-1.85 (m, 2H), 1.62-1.44 (m, 2H).

Step V: Preparation of Compound 1

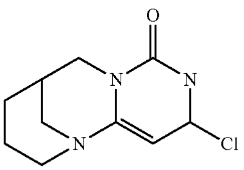

1f

-continued

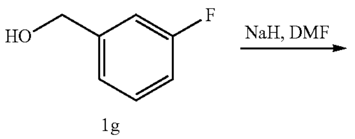

1g

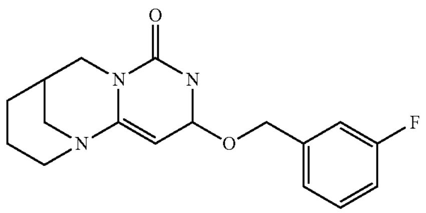

1

To a solution of (3-fluorophenyl)methanol 1g (30 mg, 0.24 mmol) in dry N,N-dimethylformamide (5 mL) was added sodium hydride (60% in mineral oil, 18 mg, 0.44 mmol) at 0° C., and stirred at room temperature for 5 min. Then compound 1f (50 mg, 0.22 mmol) was added, and stirred for 1 h, quenched with a small amount of water. Purification on a silica gel column with $CH_2Cl_2/CH_3OH$ (20/1) afforded the title compound 1 (8 mg, 11.5%) as a white solid.

$^{1}$H NMR (400 MHz, $CDCl_3$) δ 7.32 (m, 1H), 7.15 (m, 2H), 7.04-6.97 (m, 1H), 5.60 (s, 1H), 5.40 (s, 2H), 4.06 (m, 1H), 3.80 (m, 1H), 3.44 (m, 1H), 3.29-3.19 (m, 1H), 3.13 (m, 1H), 3.03 (m, 1H), 2.41 (m, 1H), 2.00-1.82 (m, 2H), 1.58-1.45 (m, 2H).

Example 2 Preparation of Compound 2

2

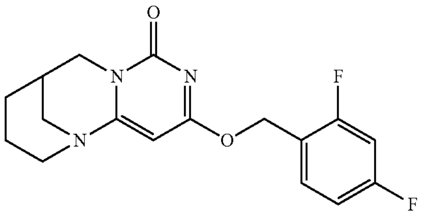

To a solution of (2,4-Difluorophenyl)methanol (35 mg, 0.24 mmol) in dry N,N-dimethylformamide (5 mL), was added sodium hydride (60% in mineral oil, 18 mg, 0.44 mmol) at 0° C., and stirred at room temperature for 5 min. Then compound 1f (50 mg, 0.22 mmol) was added, and stirred for 1 h, quenched with a small amount of water. Purification on a silica gel column with $CH_2Cl_2/CH_3OH$ (20/1) afforded the title compound 2 (10 mg, 13.6%) as a white solid.

$^{1}$H NMR (400 MHz, $CDCl_3$) δ 7.49 (m, 1H), 6.94-6.80 (m, 2H), 5.58 (s, 1H), 5.44 (s, 2H), 4.09 (m, 1H), 3.82 (m, 1H), 3.45 (m, 1H), 3.29-3.20 (m, 1H), 3.16 (m, 1H), 3.05 (mm, 1H), 2.44 (m, 1H), 2.02-1.83 (m, 2H), 1.57-1.47 (m, 2H).

Example 3 Preparation of Compound 3

3

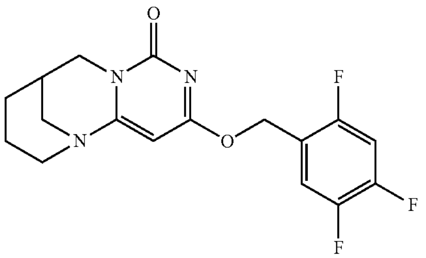

To a solution of (2,4,5-Trifluorophenyl)methanol (39 mg, 0.24 mmol) in dry N,N-dimethylformamide (5 mL), was added sodium hydride (60% in mineral oil, 18 mg, 0.44 mmol) at 0° C., and stirred at room temperature for 5 min. Then compound 1f (50 mg, 0.22 mmol) was added, and stirred for 1 h, quenched with a small amount of water. Purification on a silica gel column with $CH_2Cl_2/CH_3OH$ (20/1) afforded the title compound 3 (12 mg, 15.5%) as a white solid.

$^{1}$H NMR (400 MHz, $CDCl_3$) δ 7.32 (m, 1H), 6.93 (m, 1H), 5.57 (s, 1H), 5.40 (s, 2H), 4.06 (m, 1H), 3.79 (m, 1H), 3.43 (m, 1H), 3.28-3.21 (m, 1H), 3.13 (m, 1H), 3.02 (m, 1H), 2.42 (m, 1H), 1.93 (m, 2H), 1.50 (m, 2H). MS (ESI): m/z 352.1 $[M+H]^+$.

Example 4 Preparation of Compound 4

4

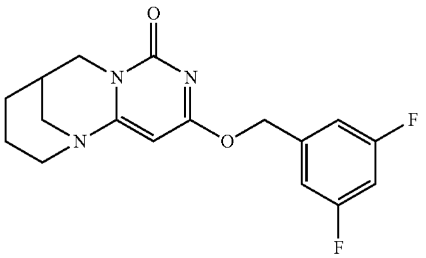

To a solution of (3,5-Difluorophenyl)methanol (35 mg, 0.24 mmol) in dry N,N-dimethylformamide (5 mL), was added sodium hydride (60% in mineral oil, 18 mg, 0.44 mmol) at 0° C., and stirred at room temperature for 5 min. Then compound 1f (50 mg, 0.22 mmol) was added, and stirred for 1 h, quenched with a small amount of water. Purification on a silica gel column with $CH_2Cl_2/CH_3OH$ (20/1) afforded the title compound 4 (6 mg, 8.2%) as a white solid.

$^{1}$H NMR (400 MHz, $CDCl_3$) δ 6.99-6.93 (m, 2H), 6.81-6.72 (m, 1H), 5.63 (s, 1H), 5.41 (s, 2H), 4.09 (m, 1H), 3.82 (m, 1H), 3.53-3.43 (m, 1H), 3.33-3.20 (m, 1H), 3.17 (m, 1H), 3.06 (m, 1H), 2.45 (m, 1H), 1.96 (m, 2H), 1.54 (m, 2H).

Example 5 Preparation of Compound 5

5

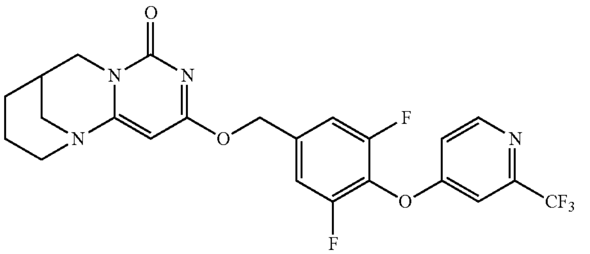

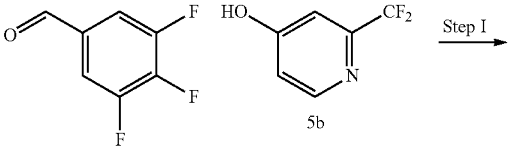

5b

5a

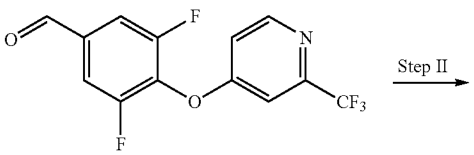

5c

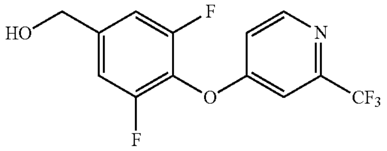

5d

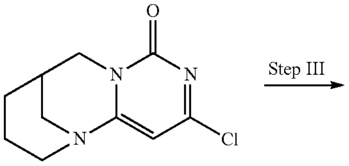

1f

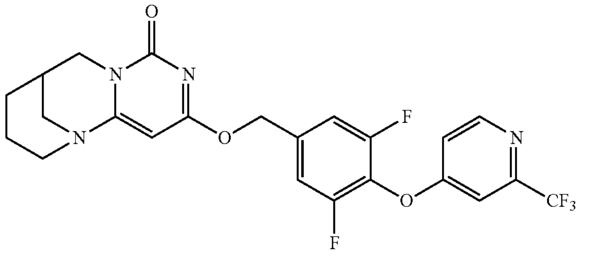

5

Step I: Preparation of Compound 5c 3,4,5-trifluorobenzaldehyde 5a (1 g, 6.2 mmol), 2-(trifluoromethyl)pyridin-4-ol 5b (1 g, 6.2 mmol) and potassium carbonate (0.93 g, 6.76 mmol) were dissolved in N,N-dimethylformamide (DMF) (30 mL) at room temperature. The reaction mixture was stirred at 90° C. for 1 h. After cooled to room temperature ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated. Purification on a silica gel column with PE/EtOAc (5/1) afforded the title compound 5c (1.47 g, 93.2%) as a yellow solid.

$^1$H NMR (400 MHz, $CDCl_3$) δ 9.97 (s, 1H), 8.65 (m, 1H), 7.63 (m, 2H), 7.27 (m, 1H), 7.01 (m, 1H).

Step II: Preparation of Compound 5d

To a solution of 3,5-difluoro-4-((2-(trifluoromethyl)pyridin-4-yl)oxy)benzaldehyde 5c (1.47 g, 4.85 mmol) dissolved in ethanol (50 mL) at room temperature, was added NaBH4 (184 mg, 4.85 mmol) at 0° C. The reaction mixture was stirred at room temperature for 0.5 h, concentrated under reduced pressure. Water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (2/1) afforded the title compound 5d (1.04 g, yield: 70.3%) as a white solid.

$^1$H NMR (400 MHz, $CDCl_3$) δ 8.59 (m, 1H), 7.24 (m, 1H), 7.11 (m, 2H), 6.99 (m, 1H), 4.75 (m, 2H), 2.19 (m, 1H).

Step III: Preparation of Compound 5

To a solution of (3,5-difluoro-4-((2-(trifluoromethyl)pyridin-4-yl)oxy)phenyl)methanol 5d (67 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 5 (13 mg, 12%) as a white solid.

$^1$H NMR (400 MHz, $CDCl_3$) δ 8.60 (m, 1H), 7.26 (s, 1H), 7.15 (m, 2H), 6.99 (m, 1H), 5.64 (s, 1H), 5.43 (s, 2H), 4.08 (m, 1H), 3.80 (m, 1H), 3.47 (m, 1H), 3.27 (m, 1H), 3.16 (m, 1H), 3.04 (m, 1H), 2.44 (m, 1H), 1.91 (m, 2H), 1.53 (m, 2H). MS (ESI): m/z 494.9 [M+H]$^+$.

Example 6 Preparation of Compound 6

6

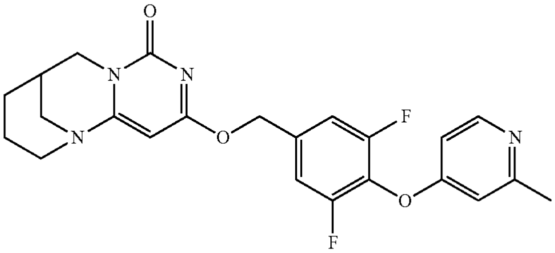

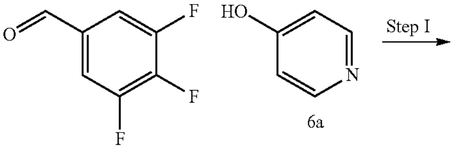

6a

5a

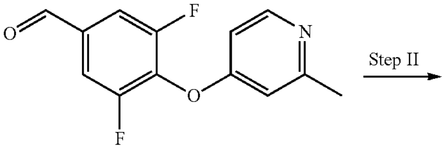

6b

-continued

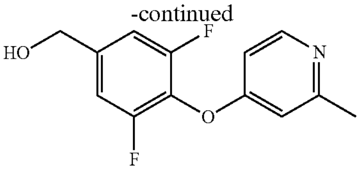

6c

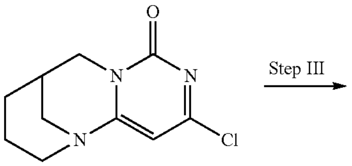

1f

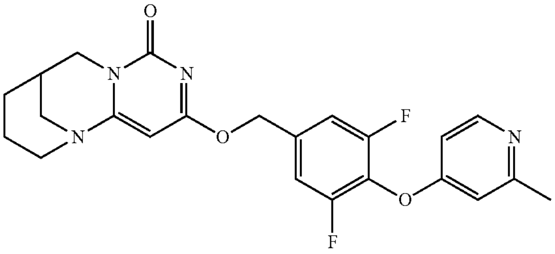

6

Step I: Preparation of Compound 6b 3,4,5-trifluorobenzaldehyde 5a (0.88 g, 5.5 mmol), 2-methylpyridin-4-ol 6a (0.5 g, 4.6 mmol), and potassium carbonate (0.93 g, 6.76 mmol) were dissolved in N,N-dimethylformamide (DMF) (30 mL) at room temperature. The reaction mixture was stirred at 90° C. for 2 h. After cooled to room temperature ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 6b (0.4 g, 34.9%) as a yellow solid.

$^1$H NMR (400 MHz, $CDCl_3$) δ 9.94 (s, 1H), 8.39 (m, 1H), 7.62-7.56 (m, 2H), 6.70-6.66 (m, 2H), 2.52 (s, 3H).

Step II: Preparation of Compound 6c

To a solution of 3,5-difluoro-4-((2-methylpyridin-4-yl)oxy)benzaldehyde 6b (0.4 g, 1.6 mmol) dissolved in methanol (50 mL) at room temperature, was added NaBH4 (71 mg, 1.86 mmol) at 0° C. The reaction mixture was stirred at room temperature for 0.5 h, concentrated under reduced pressure. Water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 6c (0.4 g, yield: 99%) as a colorless oil.

$^1$H NMR (400 MHz, $CDCl_3$) δ 8.29 (m, 1H), 7.07 (m, 2H), 6.70-6.64 (m, 2H), 4.73 (s, 2H), 3.20 (m, 1H), 2.50 (s, 3H).

Step III: Preparation of Compound 6

To a solution of (3,5-Difluoro-4-((2-methyl)pyridin-4-yl)oxy)phenyl)methanol 6c (55 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 6 (8 mg, 8.2%) as a white solid.

$^1$H NMR (400 MHz, $CDCl_3$) δ 8.36 (m, 1H), 7.10 (m, 2H), 6.70-6.66 (m, 2H), 5.63 (s, 1H), 5.42 (s, 2H), 4.08 (m, 1H), 3.81 (m, 1H), 3.47 (m, 1H), 3.30-3.22 (m, 1H), 3.16 (m, 1H), 3.05 (m, 1H), 2.51 (s, 3H), 2.44 (m, 1H), 1.91 (m, 2H), 1.53 (m, 2H). MS (ESI): m/z 441.0 $[M+H]^+$.

Example 7 Preparation of Compound 7

7

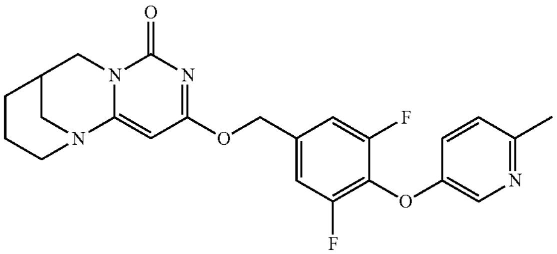

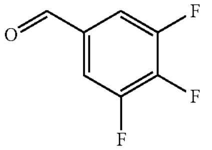

5a

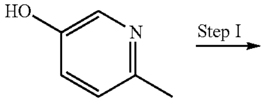

7a

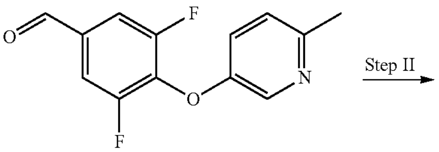

7b

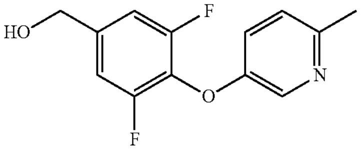

7c

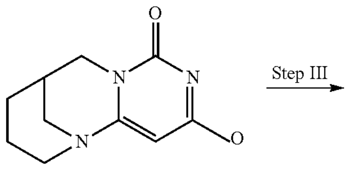

1f

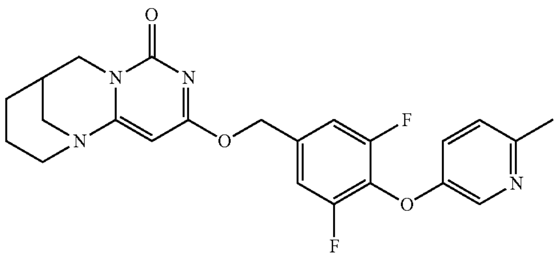

7

Step I: Preparation of Compound 7b 3,4,5-trifluorobenzaldehyde 5a (1 g, 6.2 mmol), 6-methylpyridin-3-ol 7a (0.57 g, 5.2 mmol) and potassium carbonate (0.93 g, 6.76 mmol) were dissolved in N,N-dimethylformamide (DMF) (30 mL) at room temperature. The reaction mixture was stirred at 90° C. for 1 h. After cooled to room temperature ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated. Purification on a silica gel column with PE/EtOAc (10/1) afforded the title compound 7b (0.91 g, 69.2%) as a yellow solid.

$^1$H NMR (400 MHz, $CDCl_3$) δ 9.92 (s, 1H), 8.28 (s, 1H), 7.62-7.49 (m, 2H), 7.18-7.10 (m, 2H), 2.54 (s, 3H).

Step II: Preparation of Compound 7c

To a solution of 3,5-difluoro-4-((6-methylpyridin-3-yl)oxy)benzaldehyde 7b (0.91 g, 3.6 mmol) in methanol (50 mL) was added $NaBH_4$ (161 mg, 4.3 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 7c (0.89 g, yield: 98.4%) as a colorless oil.

$^1$H NMR (400 MHz, $CDCl_3$) δ 8.20 (m, 1H), 7.16-6.98 (m, 4H), 4.69 (m, 2H), 2.88 (m, 1H), 2.50 (s, 3H).

Step III: Preparation of Compound 7

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 7 (17 mg, 17.5%) as a white solid.

$^1$H NMR (400 MHz, $CDCl_3$) δ 8.27 (m, 1H), 7.10 (m, 4H), 5.62 (s, 1H), 5.39 (s, 2H), 4.07 (m, 7.3 Hz, 1H), 3.80 (m, 1H), 3.46 (m, 1H), 3.29-3.21 (m, 1H), 3.15 (m, 1H), 3.04 (m, 1H), 2.50 (s, 3H), 2.43 (m, 1H), 1.97-1.86 (m, 2H), 1.51 (m, 2H). MS (ESI): m/z 441.0 [M+H]$^+$.

Example 8 Preparation of Compound 8

8

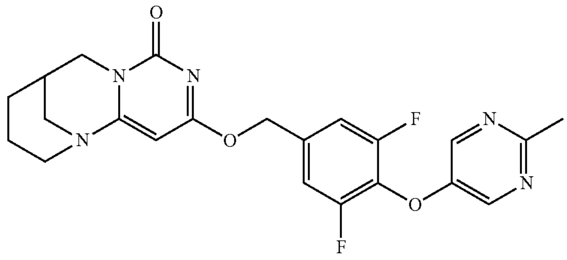

-continued

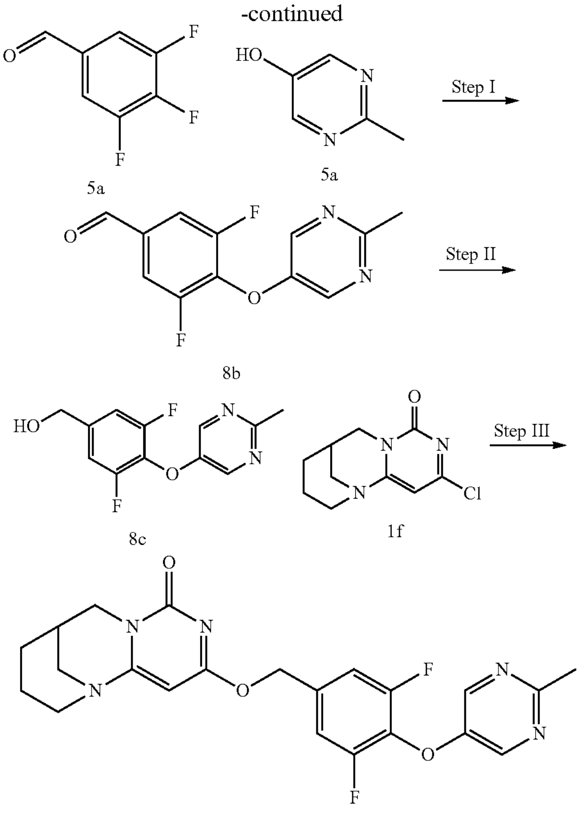

5a 5a 8b 8c 1f 8

Step I: Preparation of Compound 8b 3,4,5-trifluorobenzaldehyde 5a (0.44 g, 2.8 mmol), 2-methylpyrimidin-5-ol 8a (0.25 g, 2.3 mmol), and potassium carbonate (0.41 g, 2.9 mmol) were dissolved in N,N-dimethylformamide (DMF) (30 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 8b (0.24 g, 41.7%) as a yellow solid.

$^1$H NMR (400 MHz, $CDCl_3$) δ 9.93 (s, 1H), 8.39 (s, 2H), 7.64-7.54 (m, 2H), 2.72 (s, 3H).

Step II: Preparation of Compound 8c

To a solution of 3,5-difluoro-4-((2-methylpyrimidin-5-yl)oxy)benzaldehyde 8b (0.24 g, 0.96 mmol) dissolved in methanol (50 mL) at room temperature, was added $NaBH_4$ (30 mg, 0.79 mmol) at 0° C. The reaction mixture was stirred at room temperature for 0.5 h, concentrated under reduced pressure, water was added thereto and extracted with ethyl acetate (100 mL×2). The combined organic phases were washed with sodium chloride solution and dried over anhydrous sodium sulfate, the desiccant was filtered out and the filtrate was concentrated under reduced pressure. Purification on a silica gel column with PE/EtOAc (4/1) afforded the title compound 8c (0.17 g, yield: 70.2%) as a colorless oil.

$^1$H NMR (400 MHz, $CDCl_3$) δ 8.33 (s, 2H), 7.04 (m, 2H), 4.71 (m, 2H), 2.70 (s, 3H).

Step III: Preparation of Compound 8

To a solution of (3,5-Difluoro-4-((2-methylpyrimidin-5-yl)oxy)phenyl)methanol 8c (56 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 8 (10 mg, 10.3%) as a white solid.

$^1$H NMR (400 MHz, $CDCl_3$) δ 8.35 (s, 2H), 7.11 (m, 2H), 5.62 (s, 1H), 5.40 (s, 2H), 4.06 (s, 1H), 3.80 (m, 1H), 3.47 (m, 1H), 3.25 (s, 1H), 3.15 (m, 1H), 3.04 (m, 1H), 2.71 (s, 3H), 2.44 (m, 1H), 1.91 (m, 2H), 1.52 (m, 2H). MS (ESI): m/z 442.0 $[M+H]^+$.

Example 9 Preparation of Compound 9

9

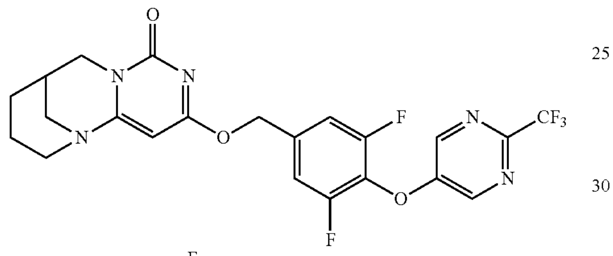

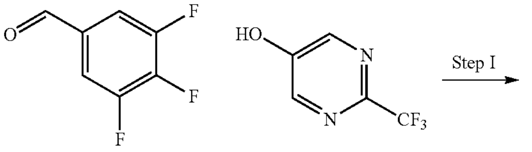

5a 9a

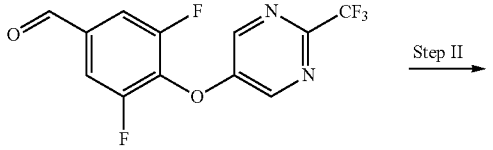

9b

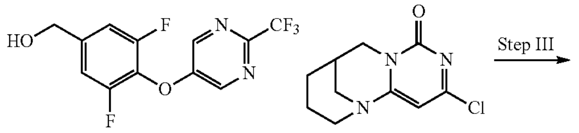

9c 1f

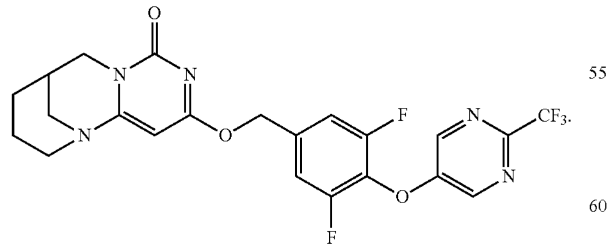

9

Step I: Preparation of Compound 9b 3,4,5-trifluorobenzaldehyde 5a (0.29 g, 1.81 mmol), 2-(trifluoromethyl)pyrimidin-5-ol 9a (0.25 g, 1.52 mmol), and potassium carbonate (0.27 g, 1.98 mmol) were dissolved in N,N-dimethylformamide (DMF) (20 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 9b (0.24 g, 51.9%) as a yellow solid.

$^1$H NMR (400 MHz, $CDCl_3$) δ 9.97 (s, 1H), 8.59 (s, 2H), 7.69-7.54 (m, 2H).

Step II: Preparation of Compound 9c

To a solution of 3,5-difluoro-4-((2-(trifluoromethyl)pyrimidin-5-yl)oxy)benzaldehyde 9b (0.24 g, 0.79 mmol) dissolved in methanol (50 mL) at room temperature, was added $NaBH_4$ (30 mg, 0.79 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 9c (0.12 g, yield: 49.6%) as a colorless oil.

$^1$H NMR (400 MHz, $CDCl_3$) δ 8.54 (s, 2H), 7.12 (m, 2H), 4.74 (m, 2H), 2.23 (m, 1H).

Step III: Preparation of Compound 9

To a solution of (3,5-Difluoro-4-((2-(trifluoromethyl)pyrimidin-5-yl)oxy)phenyl)methanol 9c (73 mg, 0.24 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 9 (8 mg, 7.3%) as a white solid.

$^1$H NMR (400 MHz, $CDCl_3$) δ 8.58 (s, 2H), 7.19 (m, 2H), 5.66 (s, 1H), 5.45 (s, 2H), 4.10 (m, 7.4 Hz, 1H), 3.82 (m, 1H), 3.49 (m, 1H), 3.34-3.23 (m, 1H), 3.18 (m, 1H), 3.07 (m, 1H), 2.47 (m, 1H), 1.97 (m, 2H), 1.60-1.50 (m, 2H). MS (ESI): m/z 496.1 $[M+H]^+$.

Example 10 Preparation of Compound 10

10

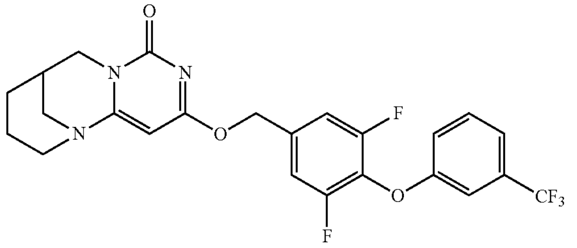

-continued

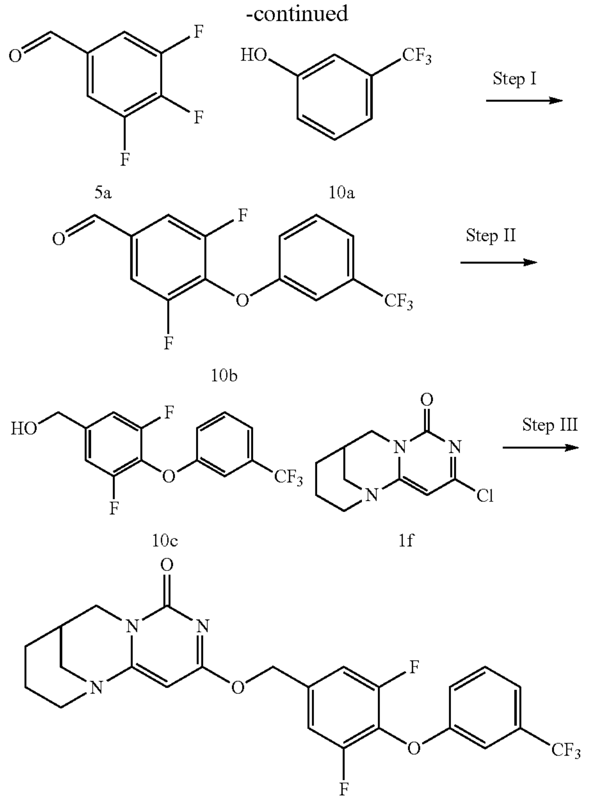

5a 10a 10b 10c 1f 10

Step I: Preparation of Compound 10b 3,4,5-trifluorobenzaldehyde 5a (1.09 g, 6.8 mmol), 3-(trifluoromethyl) phenol 10a (1 g, 6.2 mmol), and potassium carbonate (1.1 g, 8.02 mmol) were dissolved in N,N-dimethylformamide (DMF) (30 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 10b (1.7 g, 90.7%) as a yellow solid.

$^1$H NMR (400 MHz, $CDCl_3$) δ 9.94 (s, 1H), 7.63-7.55 (m, 2H), 7.46 (m, 1H), 7.39 (m, 1H), 7.21 (s, 1H), 7.13 (m, 1H).

Step II: Preparation of Compound 10c

To a solution of 3,5-difluoro-4-(3-(trifluoromethyl) phenoxy)benzaldehyde 10b (1.7 g, 5.6 mmol) dissolved in methanol (50 mL) at room temperature, was added $NaBH_4$ (213 mg, 5.6 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 10c (1.27 g, yield: 74.5%) as a colorless oil.

Step III: Preparation of Compound 10

To a solution of (3,5-Difluoro-4-(3-(trifluoromethyl) phenoxy)phenyl)methanol 10c (73 mg, 0.24 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 10 (6 mg, 5.5%) as a white solid.

$^1$H NMR (400 MHz, $CDCl_3$) δ 7.42 (m, 1H), 7.33 (m, 1H), 7.20 (s, 1H), 7.10 (m, 3H), 5.63 (s, 1H), 5.41 (s, 2H), 4.11-4.02 (m, 1H), 3.80 (m, 1H), 3.47 (m, 1H), 3.26 (m, 1H), 3.15 (m, 1H), 3.04 (m, 1H), 2.43 (m, 1H), 2.00-1.85 (m, 2H), 1.55-1.48 (m, 2H). MS (ESI): m/z 494.0 $[M+H]^+$.

Example 11 Preparation of Compound 11

11

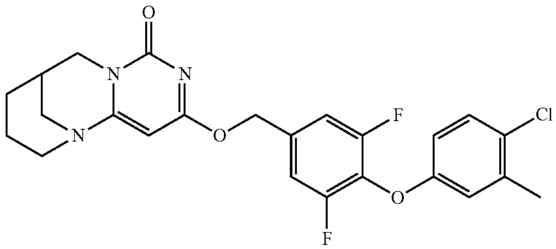

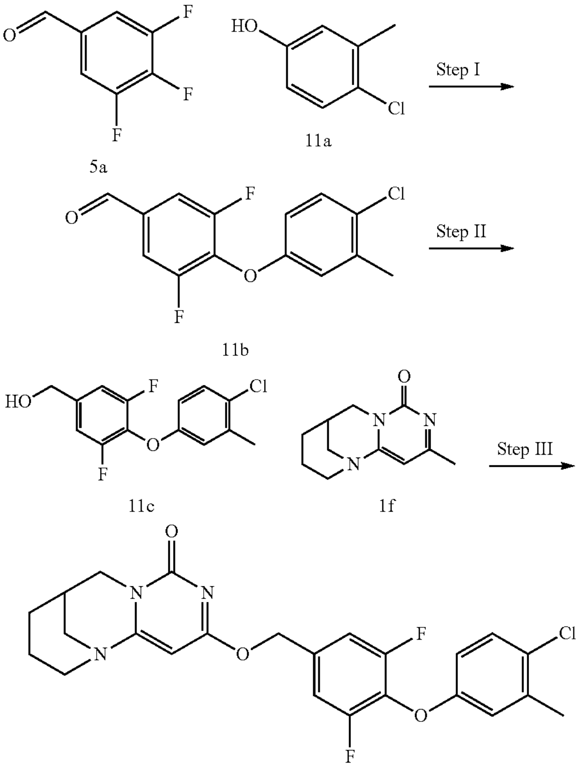

5a 11a 11b 11c 1f 11

Step I: Preparation of Compound 11b 3,4,5-trifluorobenzaldehyde 5a (1.2 g, 7.5 mmol), 4-chloro-3-methylphenol 11a (1 g, 7.0 mmol) and potassium carbonate (1.1 g, 8.02 mmol) were dissolved in N,N-dimethylformamide (DMF) (30 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 11b (1.2 g, 60.6%) as a yellow solid.

$^1H$ NMR (400 MHz, $CDCl_3$) δ 9.92 (s, 1H), 7.61-7.51 (m, 2H), 7.30-7.23 (m, 1H), 6.85 (m, 1H), 6.73 (m, 1H), 2.34 (s, 3H).

Step II: Preparation of Compound 11c

To a solution of 4-(4-chloro-3-methylphenoxy)-3,5-difluorobenzaldehyde 11b (1.2 g, 4.2 mmol) dissolved in methanol (50 mL) at room temperature, was added $NaBH_4$ (161 mg, 4.2 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 11c (0.89 g, yield: 74.4%) as a colorless oil.

Step III: Preparation of Compound 11

To a solution of 4-(4-Chloro-3-methylphenoxy)-3,5-difluorobenzyl alcohol 11c (77 mg, 0.27 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 11 (9 mg, 8.6%) as a white solid.

$^1H$ NMR (400 MHz, $CDCl_3$) δ 7.27 (m, 1H), 7.12 (m, 2H), 6.86 (m, 1H), 6.74 (m, 1H), 5.66 (s, 1H), 5.43 (s, 2H), 4.11 (m, 1H), 3.84 (m, 1H), 3.50 (m, 1H), 3.34-3.25 (m, 1H), 3.19 (m, 1H), 3.08 (m, 1H), 2.47 (m, 1H), 2.36 (s, 3H), 1.98 (m, 2H), 1.61-1.51 (m, 2H).

Example 12 Preparation of Compound 12

12

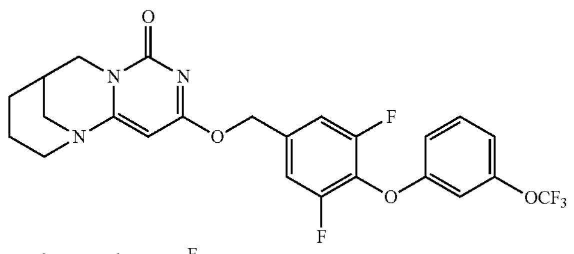

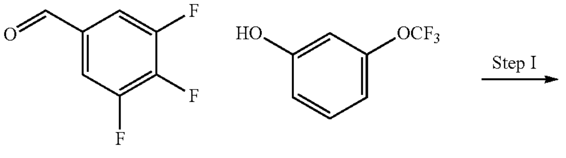

5a 12a

-continued

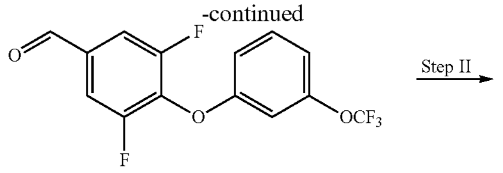

12b

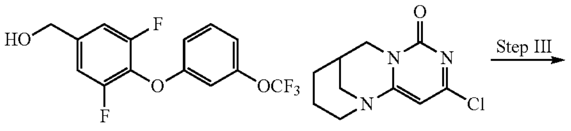

12c 1f

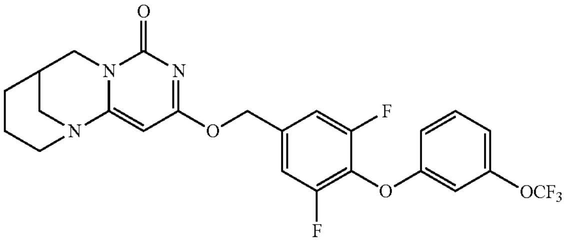

12

Step I: Preparation of Compound 12b 3,4,5-trifluorobenzaldehyde 5a (0.5 g, 2.8 mmol), 3-(trifluoromethoxy) phenol 12a (0.5 g, 2.8 mmol), and potassium carbonate (0.5 g, 3.6 mmol) were dissolved in N,N-dimethylformamide (DMF) (30 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 12b (0.73 g, 91.8%) as a yellow solid.

$^1H$ NMR (400 MHz, $CDCl_3$) δ 9.94 (s, 1H), 7.64-7.54 (m, 2H), 7.34 (m, 1H), 7.00 (m, 1H), 6.87 (m, 2H).

Step II: Preparation of Compound 12c

To a solution of 4-(3-(trifluoromethoxy) phenoxy)-3,5-difluorobenzaldehyde 12b (0.73 g, 2.3 mmol) dissolved in methanol (50 mL) at room temperature, was added $NaBH_4$ (86 mg, 2.28 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 12c (0.57 g, yield: 77.4%) as a colorless oil.

$^1H$ NMR (400 MHz, $CDCl_3$) δ 7.30 (m, 1H), 7.06 (m, 2H), 6.94 (m, 1H), 6.85 (m, 1H), 6.81 (s, 1H), 4.72 (m, 2H), 1.94 (m, 1H).

Step III: Preparation of Compound 12

To a solution of (4-(3-(Trifluoromethoxy) phenoxy)-3,5-difluorophenyl)methanol 12c (70 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 12 (6 mg, 5.4%) as a white solid.

$^1H$ NMR (400 MHz, $CDCl_3$) δ 7.29 (m, 1H), 7.08 (m, 2H), 6.93 (m, 1H), 6.88-6.77 (m, 2H), 5.62 (s, 1H), 5.39 (s, 2H), 4.06 (m, 1H), 3.81 (m, 1H), 3.46 (m, 1H), 3.31-3.20 (m, 1H), 3.13 (m, 1H), 3.04 (m, 1H), 2.43 (m, 1H), 1.89 (m, 2H), 1.51 (m, 2H). MS (ESI): m/z 510.0 $[M+H]^+$.

Example 13 Preparation of Compound 13

13

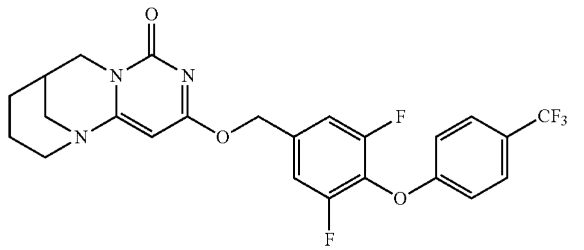

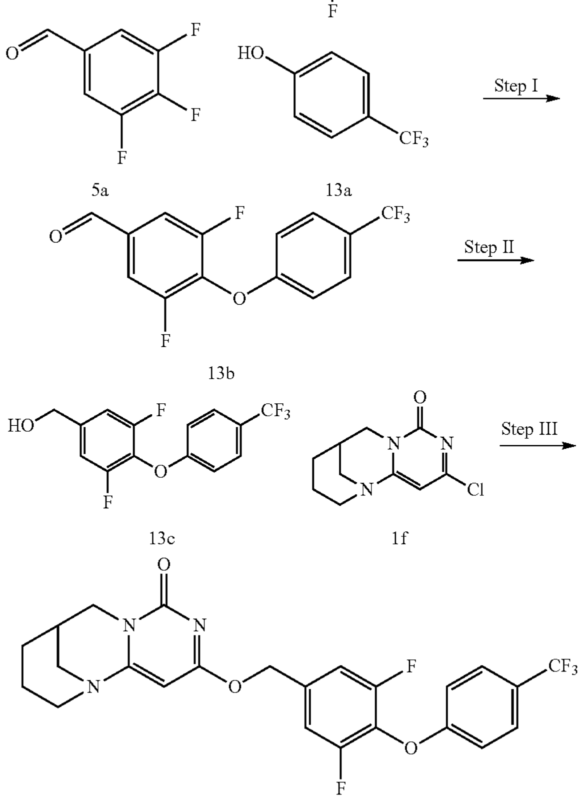

5a

13a

13b

13c

1f

13

Step I: Preparation of Compound 13b 3,4,5-trifluorobenzaldehyde 5a (1 g, 6.2 mmol), 4-(trifluoromethyl) phenol 13a (0.84 g, 5.2 mmol), and potassium carbonate (0.93 g, 6.76 mmol) were dissolved in N,N-dimethylformamide (DMF) (30 mL) at room temperature. The reaction mixture was stirred at 90° C. for 1 h. After cooled to room temperature ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (5/1) afforded the title compound 13b (1.33 g, 84.6%) as a yellow solid.

$^1H$ NMR (400 MHz, $CDCl_3$) δ 9.94 (m, 1H), 7.59 (m, 4H), 7.04 (m, 2H).

Step II: Preparation of Compound 13c

To a solution of 3,5-difluoro-4-(4-(trifluoromethyl) phenoxy)benzaldehyde 13b (1.33 g, 4.4 mmol) dissolved in methanol (50 mL) at room temperature, was added $NaBH_4$ (166 mg, 4.4 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (2/1) afforded the title compound 13c (0.85 g, yield: 63.5%) as a colorless oil.

$^1H$ NMR (400 MHz, $CDCl_3$) δ 7.57 (m, 2H), 7.09-7.00 (m, 4H), 4.72 (m, 2H), 2.03 (m, 1H).

Step III: Preparation of Compound 13

To a solution of 3,5-Difluoro-4-(4-(trifluoromethyl) phenoxy)phenyl)methanol 13c (67 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 13 (11 mg, 10.1%) as a white solid.

$^1H$ NMR (400 MHz, $CDCl_3$) δ 7.57 (m, 2H), 7.10 (m, 2H), 7.01 (m, 2H), 5.63 (s, 1H), 5.41 (s, 2H), 4.11-4.04 (m, 1H), 3.80 (m, 1H), 3.47 (m, 1H), 3.30-3.21 (m, 1H), 3.16 (m, 1H), 3.04 (m, 1H), 2.44 (m, 1H), 1.99-1.85 (m, 2H), 1.57-1.48 (m, 2H). MS (ESI): m/z 494.0 $[M+H]^+$.

Example 14 Preparation of Compound 14

14

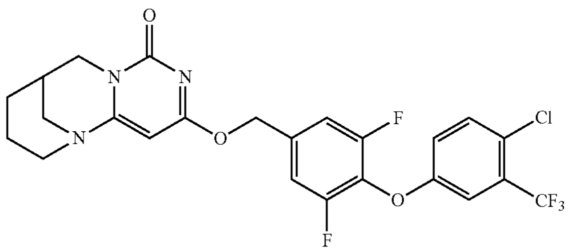

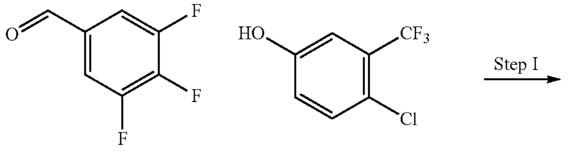

5a

14a

-continued

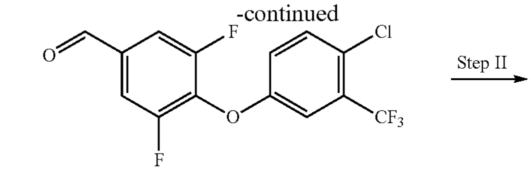

14b

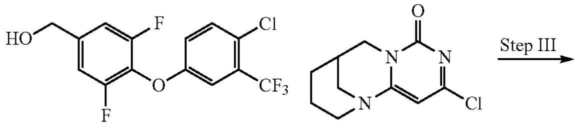

14c 1f

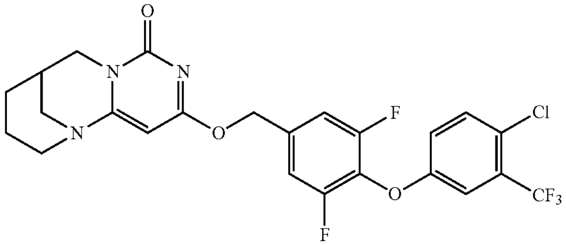

14

Step I: Preparation of Compound 14b 3,4,5-trifluorobenzaldehyde 5a (0.45 g, 2.8 mmol), 4-chloro-3-(trifluoromethyl) phenol 14a (0.5 g, 2.5 mmol), and potassium carbonate (0.46 g, 3.3 mmol) were dissolved in N,N-dimethylformamide (DMF) (30 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 14b (0.6 g, 71.3%) as a yellow solid.

$^1$H NMR (400 MHz, $CDCl_3$) δ 9.94 (s, 1H), 7.64-7.55 (m, 2H), 7.45 (m, 1H), 7.31 (m, 1H), 7.05 (m, 1H).

Step II: Preparation of Compound 14c

To a solution of 4-(4-chloro-3-(trifluoromethyl) phenoxy)-3,5-difluorobenzaldehyde 14b (0.6 g, 1.78 mmol) dissolved in methanol (50 mL) at room temperature, was added $NaBH_4$ (67 mg, 1.78 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduce pressure. Purification on a silica gel column with PE/EtOAc (4/1) afforded the title compound 14c (0.28 g, yield: 46.4%) as a white solid.

$^1$H NMR (400 MHz, $CDCl_3$) δ 7.41 (m, 1H), 7.28 (m, 1H), 7.08-7.00 (m, 3H), 4.73 (m, 2H), 1.94 (m, 1H).

Step III: Preparation of Compound 14

To a solution of (4-(4-Chloro-3-(trifluoromethyl) phenoxy)-3,5-difluorophenyl)methanol 14c (74 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 14 (22 mg, 18.9%) as a white solid.

$^1$H NMR (400 MHz, $CDCl_3$) § 7.41 (m, 1H), 7.30 (m, 1H), 7.11 (m, 2H), 7.01 (m, 1H), 5.63 (s, 1H), 5.41 (s, 2H), 4.07 (m, 1H), 3.80 (m, 1H), 3.47 (m, 1H), 3.30-3.21 (m, 1H), 3.15 (m, 1H), 3.04 (m, 1H), 2.44 (m, 1H), 1.95 (m, 2H), 1.57-1.47 (m, 2H).

Example 15 Preparation of Compound 15

15

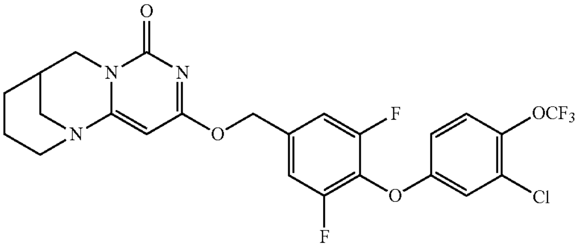

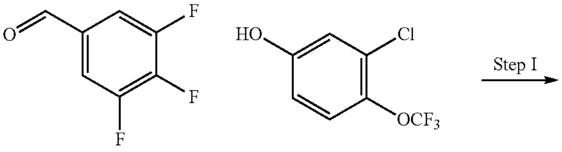

5a 15a

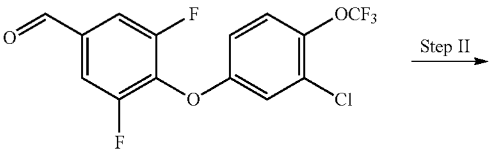

15b

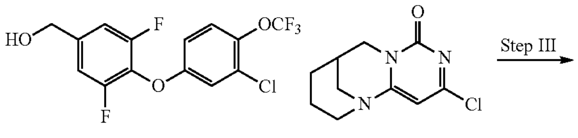

15c 1f

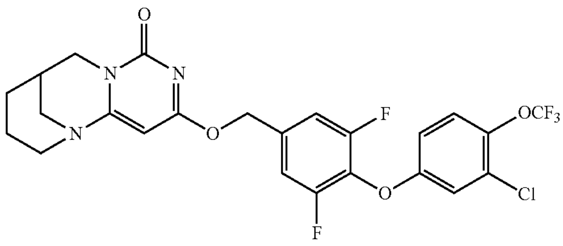

15

Step I: Preparation of Compound 15b 3,4,5-trifluorobenzaldehyde 5a (0.41 g, 2.6 mmol), 3-chloro-4-(trifluoromethoxy) phenol 15a (0.5 g, 2.4 mmol), and potassium carbonate (0.42 g, 3.04 mmol) were dissolved in N,N-dimethylformamide (DMF) (20 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduce pressure. Purification on a silica gel column with PE/EtOAc (10/1) afforded the title compound 15b (0.62 g, 73.2%) as a yellow solid.

$^1$H NMR (400 MHz, $CDCl_3$) δ 9.94 (s, 1H), 7.63-7.54 (m, 2H), 7.29 (m, 1H), 7.07 (m, 1H), 6.90 (m, 1H).

Step II: Preparation of Compound 15c

To a solution of 4-(3-chloro-4-(trifluoromethoxy) phenoxy)-3,5-difluorobenzaldehyde 15b (0.62 g, 1.8 mmol) dissolved in methanol (50 mL), was added $NaBH_4$ (62 mg, 1.9 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 15c (0.53 g, yield: 83.0%) as a colorless oil.

$^1$H NMR (400 MHz, $CDCl_3$) δ 7.25 (m, 1H), 7.06 (m, 2H), 7.01 (m, 1H), 6.87 (m, 1H), 4.72 (s, 2H), 2.04 (m, 1H).

Step III: Preparation of Compound 15

To a solution of (4-(3-Chloro-4-(trifluoromethoxy) phenoxy)-3,5-difluorophenyl)methanol 15c (79 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 15 (7 mg, 5.8%) as a white solid.

$^1$H NMR (400 MHz, $CDCl_3$) δ 7.24 (m, 1H), 7.10 (m, 2H), 7.03 (m, 1H), 6.87 (m, 1H), 5.63 (s, 1H), 5.41 (s, 2H), 4.10-4.03 (m, 1H), 3.80 (m, 1H), 3.47 (m, 1H), 3.30-3.21 (m, 1H), 3.16 (m, 1H), 3.04 (m, 1H), 2.44 (m, 1H), 1.95 (m, 2H), 1.56-1.49 (m, 2H).

Example 16 Preparation of Compound 16

16

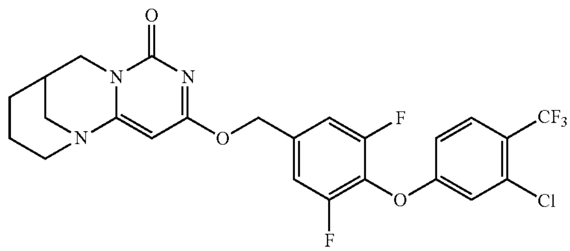

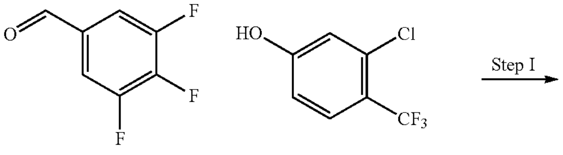

5a 16a

-continued

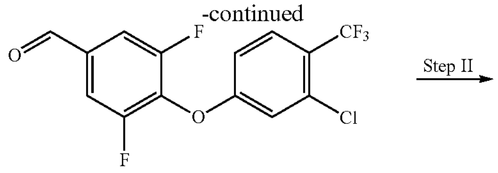

16b

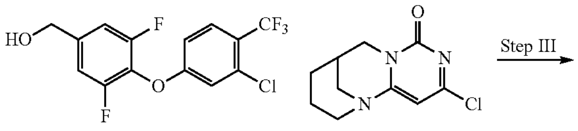

16c 1f

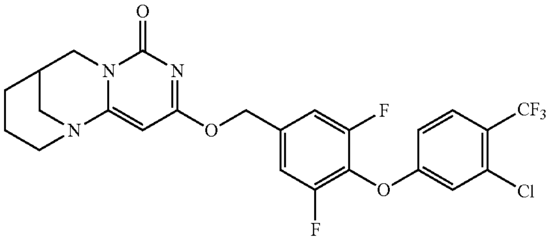

16

Step I: Preparation of Compound 16b 3,4,5-trifluorobenzaldehyde 5a (0.22 g, 1.4 mmol), 3-chloro-4-(trifluoromethyl) phenol 16a (0.25 g, 1.23 mmol) and potassium carbonate (0.23 g, 1.65 mmol) were dissolved in N,N-dimethylformamide (DMF) (20 mL) at room temperature. The reaction mixture was stirred at 90° C. for 2 h. After cooled down ice water (100 mL) was added thereto. The reaction mixture was extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (10/1) afforded the title compound 16b (0.32 g, 77.3%) as a yellow solid.

$^1$H NMR (400 MHz, $CDCl_3$) δ 9.95 (s, 1H), 7.69-7.56 (m, 3H), 7.10 (m, 1H), 6.92 (m, 1H).

Step II: Preparation of Compound 16c

To a solution of 4-(3-chloro-4-(trifluoromethyl) phenoxy)-3,5-difluorobenzaldehyde 16b (0.32 g, 0.95 mmol) dissolved in methanol (50 mL) at room temperature, was added $NaBH_4$ (36 mg, 0.94 mmol) at 0° C. The reaction mixture was stirred at room temperature for 0.5 h, concentrated under reduced pressure, water was added thereto and extracted with ethyl acetate (100 mL×2). The combined organic phases were washed with a saturated aqueous solution of sodium chloride and dried over anhydrous sodium sulfate, the desiccant was filtered out and the filtrate was concentrated under reduced pressure. Purification on a silica gel column with PE/EtOAc (4/1) afforded the title compound 16c (0.15 g, yield: 46.6%) as a while solid.

$^1$H NMR (400 MHz, $CDCl_3$) δ 7.62 (m, 1H), 7.13-7.00 (m, 3H), 6.90 (m, 1H), 4.74 (m, 2H), 1.88 (m, 1H).

Step III: Preparation of Compound 16

To a solution of (4-(3-Chloro-4-(trifluoromethyl) phenoxy)-3,5-difluorophenyl)methanol 16c (74.5 mg, 0.22 mmol) in dry N,N-dimethylformamide (5 mL) was added sodium hydride (60% in mineral oil, 18 mg, 0.44 mmol) at 0° C., and stirred for 5 min at room temperature, followed by addition of compound 1f (50 mg, 0.22 mmol). The reaction mixture was stirred for 1 h, quenched with a small amount of water. Purification on a silica gel column with dichloromethane/methanol (20/1) afforded the title compound 16 (13 mg, 11.2%) as a white solid.

$^1$H NMR (400 MHz, $CDCl_3$) δ 7.62 (m, 1H), 7.12 (m, 2H), 7.07 (m, 1H), 6.90 (m, 1H), 5.63 (s, 1H), 5.42 (s, 2H), 4.12-4.03 (m, 1H), 3.81 (m, 1H), 3.45 (m, 1H), 3.32-3.21 (m, 1H), 3.16 (m, 1H), 3.05 (m, 1H), 2.44 (m, 1H), 1.91 (m, 2H), 1.56-1.49 (m, 2H).

Example 17 Preparation of Compound 17

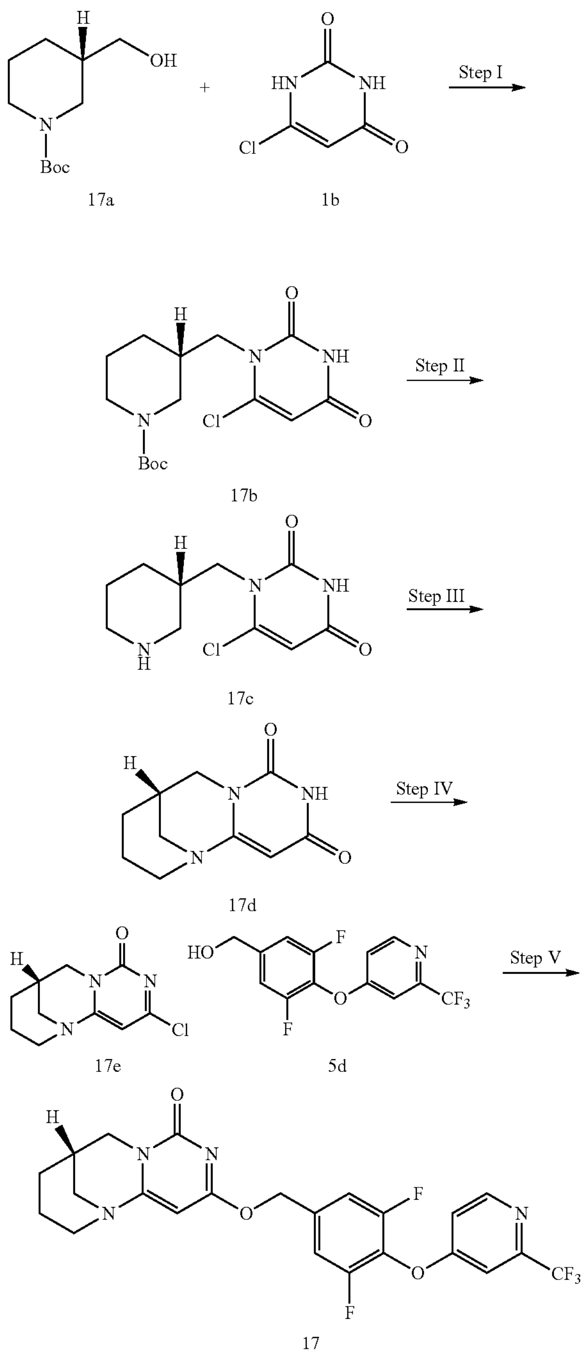

17a 1b 17b 17c 17d 17e 5d 17

Step I: Preparation of Compound 17b

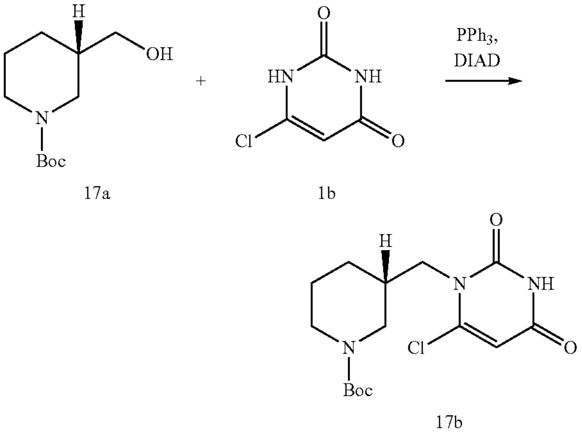

17a 1b 17b

To a solution of 6-chlorouracil 1b (8.2 g, 55.9 mmol), tert-butyl (S)-3-(hydroxymethyl)piperidine-1-carboxylate 17a (12 g, 55.7 mmol) and triphenylphosphine (20 g, 76.2 mmol) dissolved in a mixed solvent of anhydrous tetrahydrofuran (250 mL) and N,N-dimethylformamide (50 mL) at room temperature, was added dropwise diisopropyl azodicarboxylate (20 ml, 111.6 mmol) under nitrogen at 0° C. The reaction mixture was stirred at 0° C. for 2 h, then warmed to room temperature and stirred overnight. The reaction mixture was filtered and extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with $CH_2Cl_2/CH_3OH$ (20/1) afforded the title compound 17b (7.8 g, yield: 40.6%) as a colorless oil.

Steps II and III: Preparation of Compound 17d

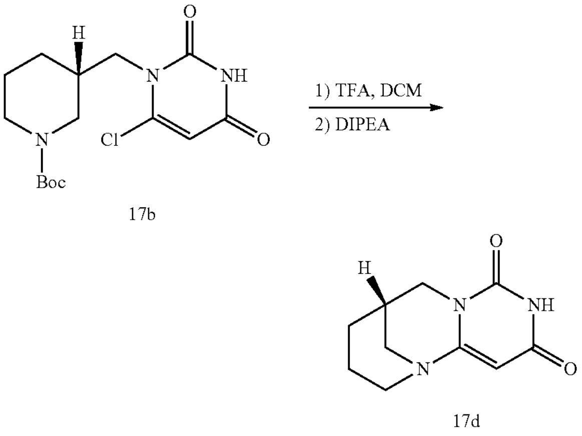

17b 17d

To a solution of tert-butyl (S)-3-((6-chloro-2,4-dioxo-3,4-dihydropyrimidin-1(2H)-yl)methyl)piperidine-1-carboxylate) 17b (7.8 g, 22.7 mmol) dissolved in dichloromethane (80 mL) at room temperature, was added trifluoroacetic acid (10 mL) at 0° C. The reaction mixture was stirred at room temperature for 2 h, and concentrated under reduced pressure. The afforded residue was used directly in the next step, and dissolved in acetonitrile (80 mL), then diisopropylethylamine (8.8 g, 68.1 mmol) was added at room temperature. The reaction mixture was stirred for 4 h, and concentrated under reduced pressure, followed by purification on a silica gel column $CH_2Cl/CH_3OH$ (20/1) to afford the title compound 17d (1.5 g, 31.9%) as a white solid.

$^1$H NMR (400 MHz, $CDCl_3$) δ 9.51 (s, 1H), 5.35 (s, 1H), 4.03 (m, 1H), 3.78-3.64 (m, 1H), 3.43 (m, 1H), 3.24 (m, 1H), 3.18-2.96 (m, 2H), 2.37 (m, 1H), 2.00-1.83 (m, 2H), 1.72-1.49 (m, 2H).

Step IV: Preparation of Compound 17e

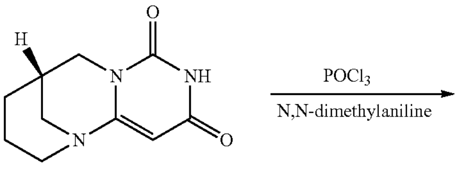

17d

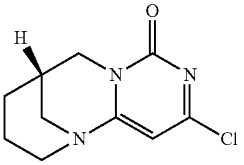

17e

To a solution of compound 17d (0.51 g, 2.46 mmol) and dimethylaniline (0.3 g, 2.47 mmol) in toluene, was added phosphorous oxychloride (0.76 g, 4.96 mmol) dropwise at room temperature. The reaction mixture was heated to reflux for 4 h, quenched with ice water, and concentrated under reduced pressure. The residue was extracted with ethyl acetate (60 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with $CH_2Cl_2$/$CH_3OH$ (20/1) afforded the title compound 17e (0.24 g, 43.2%) as a white solid.

$^1$H NMR (400 MHz, $CDCl_3$) δ 6.05 (s, 1H), 4.04 (m, 1H), 3.74 (m, 1H), 3.51 (m, 1H), 3.28 (m, 1H), 3.20-3.14 (m, 1H), 3.01 (m, 1H), 2.51 (m, 1H), 1.92 (m, 2H), 1.59-1.41 (m, 2H).

Step V: Preparation of Compound 17

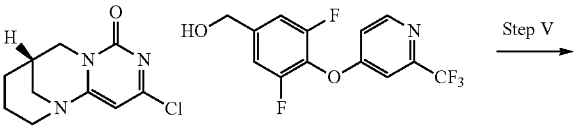

17e 5d

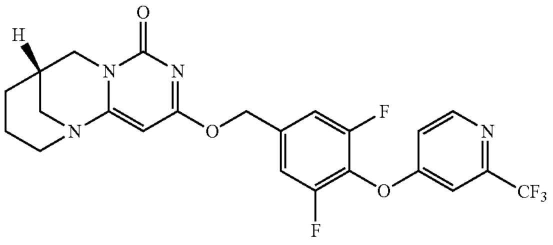

17

To a solution of (3,5-Difluoro-4-((2-(trifluoromethylpyridin-4-yl)oxy)phenyl)methanol 5d (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 17e (50 mg, 0.22 mmol). The reaction mixture was stirred for 1 h, quenched with a small amount of water. Purification on a silica gel column with dichloromethane/methanol (20/1) afforded the title compound 17 (28 mg, 25.7%) as a white solid.

$^1$H NMR (400 MHz, $CDCl_3$) δ 8.59 (m, 1H), 7.25 (s, 1H), 7.15 (m, 2H), 6.98 (m, 1H), 5.63 (s, 1H), 5.42 (s, 2H), 4.07 (m, 1H), 3.80 (m, 1H), 3.46 (m, 1H), 3.27 (m, 1H), 3.16 (m, 1H), 3.03 (m, 1H), 2.44 (m, 1H), 1.90 (m, 2H), 1.52 (m, 2H). MS (ESI): m/z 495.1 $[M+H]^+$.

Example 18 Preparation of Compound 18

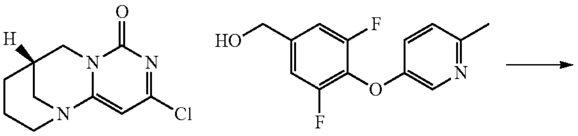

17e 7c

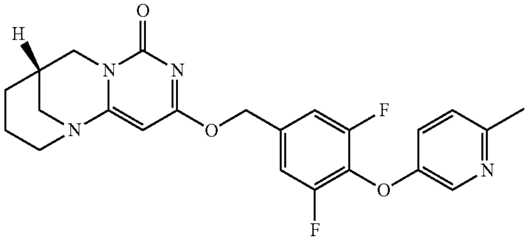

18

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 17e (50 mg, 0.22 mmol). The reaction mixture was stirred for 1 h, quenched with a small amount of water. Purification on a silica gel column with dichloromethane/methanol (20/1) afforded the title compound 18 (22 mg, 22.7%) as a white solid.

$^1$H NMR (400 MHz, $CDCl_3$) δ 8.27 (m, 1H), 7.10 (m, 4H), 5.62 (s, 1H), 5.39 (s, 2H), 4.07 (m, 1H), 3.80 (m, 1H), 3.46 (m, 1H), 3.29-3.21 (m, 1H), 3.15 (m, 1H), 3.04 (m, 1H), 2.51 (s, 3H), 2.44 (m, 1H), 1.99-1.84 (m, 2H), 1.51 (m, 2H). MS (ESI): m/z 441.2 $[M+H]^+$.

Example 19 Preparation of Compound 19

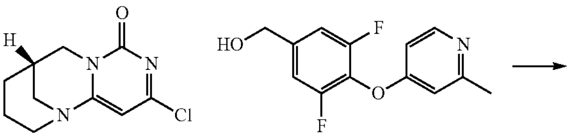

17e 6c

-continued

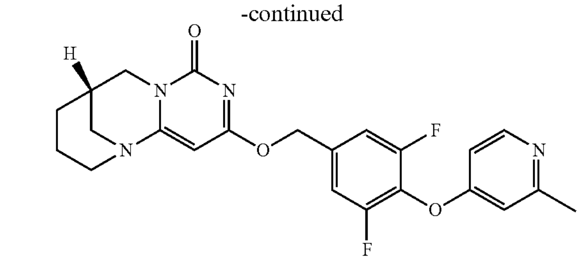

19

To a solution of (3,5-Difluoro-4-((2-methyl)pyridin-4-yl)oxy)phenyl)methanol 6c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 17e (50 mg, 0.22 mmol). The reaction mixture was stirred for 1 h, quenched with a small amount of water. Purification on a silica gel column with dichloromethane/methanol (20/1) afforded the title compound 19 (58 mg, 59.8%) as a white solid.

$^1$H NMR (400 MHz, $CDCl_3$) δ 8.35 (m, 1H), 7.10 (m, 2H), 6.67 (m, 2H), 5.62 (s, 1H), 5.41 (s, 2H), 4.07 (m, 1H), 3.79 (m, 1H), 3.46 (m, 1H), 3.30-3.18 (m, 1H), 3.15 (m, 1H), 3.04 (m, 1H), 2.50 (s, 3H), 2.43 (m, 1H), 1.91 (m, 2H), 1.55-1.46 (m, 2H). MS (ESI): m/z 441.2 $[M+H]^+$.

Example 20 Preparation of Compound 20

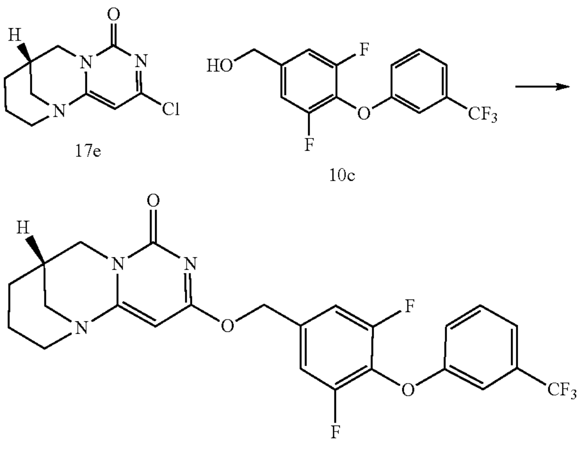

17e

10c

20

To a solution of (3,5-Difluoro-4-(3-(trifluoromethyl) phenoxy)phenyl)methanol 10c (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 17e (50 mg, 0.22 mmol). The reaction mixture was stirred for 1 h, quenched with a small amount of water. Purification on a silica gel column with dichloromethane/methanol (20/1) afforded the title compound 20 (46 mg, 42.4%) as a white solid.

$^1$H NMR (400 MHz, $CDCl_3$) δ 7.41 (m, 1H), 7.32 (m, 1H), 7.19 (s, 1H), 7.09 (m, 3H), 5.62 (s, 1H), 5.40 (s, 2H), 4.06 (m, 1H), 3.79 (m, 1H), 3.46 (m, 1H), 3.30-3.19 (m, 1H), 3.14 (m, 1H), 3.03 (m, 1H), 2.43 (m, 1H), 1.98-1.84 (m, 2H), 1.57-1.46 (m, 2H). MS (ESI): m/z 494.1 $[M+H]^+$.

Example 21 Preparation of Compound 21

21

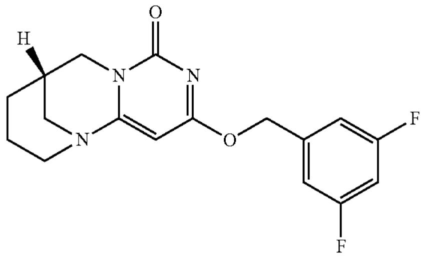

To a solution of 3,5-Difluorobenzyl alcohol (32 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 17e (50 mg, 0.22 mmol). The reaction mixture was stirred for 1 h, quenched with a small amount of water. Purification on a silica gel column with dichloromethane/methanol (20/1) afforded the title compound 21 (17 mg, 23.2%) as a white solid.

$^1$H NMR (400 MHz, $CDCl_3$) δ 6.96-6.87 (m, 2H), 6.74 (m, 1H), 5.60 (s, 1H), 5.37 (s, 2H), 4.06 (m, 1H), 3.79 (m, 1H), 3.45 (m, 1H), 3.23 (m, 1H), 3.14 (m, 1H), 3.03 (m, 1H), 2.42 (m, 1H), 1.99-1.83 (m, 2H), 1.57-1.46 (m, 2H). MS (ESI): m/z 334.1 $[M+H]^+$.

Example 22 Preparation of Compound 22

22

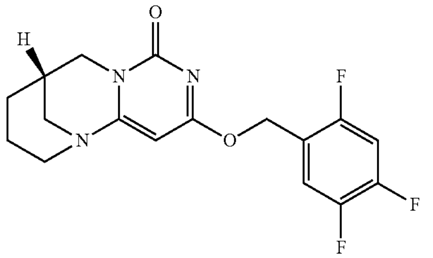

To a solution of 2,4,5-Trifluorobenzyl alcohol (36 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 17e (50 mg, 0.22 mmol). The reaction mixture was stirred for 1 h, quenched with a small amount of water. Purification on a silica gel column with dichloromethane/methanol (20/1) afforded the title compound 22 (36 mg, 46.6%) as a white solid.

$^1$H NMR (400 MHz, $CDCl_3$) δ 7.32 (m, 1H), 6.94 (m, 1H), 5.57 (s, 1H), 5.40 (s, 2H), 4.06 (m, 1H), 3.79 (m, 1H), 3.44 (m, 1H), 3.29-3.17 (m, 1H), 3.14 (m, 1H), 3.03 (m, 1H), 2.42 (m, 1H), 1.99-1.83 (m, 2H), 1.55-1.45 (m, 2H). MS (ESI): m/z 352.1 $[M+H]^+$.

Example 23 Preparation of Compound 23

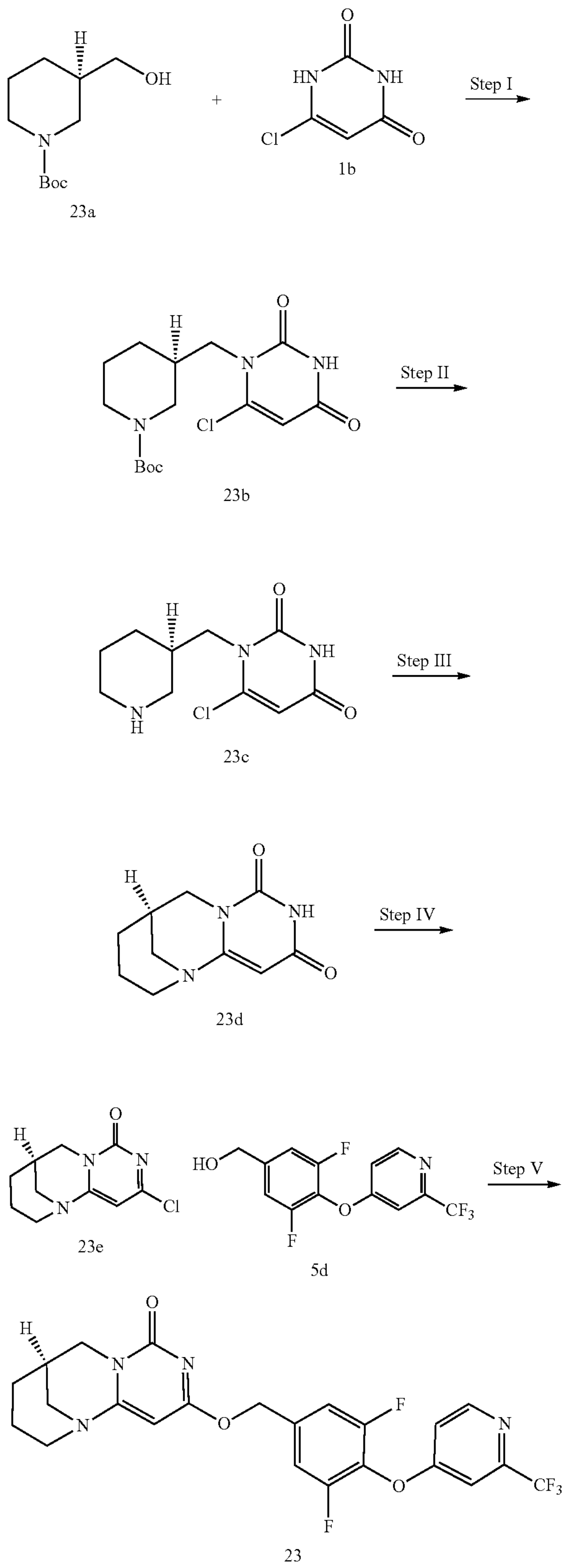

23a 1b 23b 23c 23d 23e 5d 23

Step I: Preparation of Compound 23b

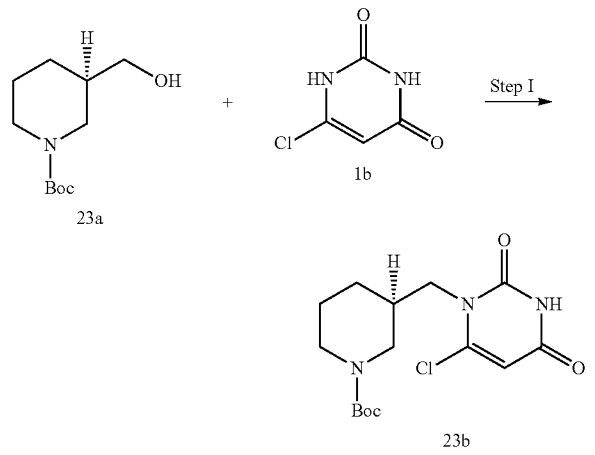

23a 1b 23b

To a solution of 6-chlorouracil 1b (6.1 g, 41.6 mmol), tert-butyl (R)-3-(hydroxymethyl)piperidine-1-carboxylate 23a (9 g, 41.8 mmol) and triphenylphosphine (16.3 g, 62.1 mmol) dissolved in a mixed solvent of anhydrous tetrahydrofuran (250 mL) and N,N-dimethylformamide (50 mL) at room temperature, was added dropwise diisopropyl azodicarboxylate (16 ml, 83 mmol) under nitrogen at 0° C. The reaction mixture was stirred at 0° C. for 2 h, then warmed to room temperature and stirred overnight. The reaction mixture was filtered and extracted with ethyl acetate (50 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with $CH_2Cl_2/CH_3OH$ (20/1) afforded the title compound 23b (8.3 g, yield: 58%) as a colorless oil.

Steps II and III: Preparation of Compound 23d

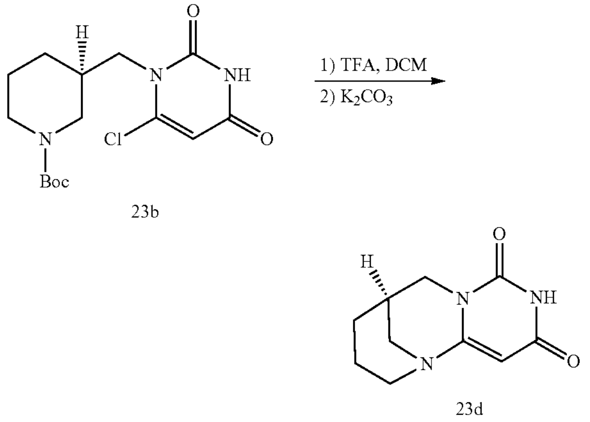

23b 23d

To a of tert-butyl solution (R)-3-((6-chloro-2,4-dioxo-3,4-dihydropyrimidin-1(2H)-yl)methyl)piperidine-1-carboxylate) 23b (8.3 g, 24.1 mmol) dissolved in dichloromethane (80 mL) at room temperature, was added trifluoroacetic acid (10 mL) at 0° C. The reaction mixture was stirred at room temperature for 2 h, and concentrated under reduced pressure. The afforded residue was used directly in the next step, and dissolved in acetonitrile (80 mL), then potassium carbonate (7.0 g, 50.9 mmol) was added at room temperature. The reaction mixture was heated to reflux overnight, and filtrated, and the filter cake was washed with acetonitrile and methanol, respectively. The filtrate was concentrated under reduced pressure, followed by purification on a silica gel column $CH_2Cl_2/CH_3OH$ (20/1) to afford the title compound 23d (1.5 g, 29.9%) as a white solid.

$^1H$ NMR (400 MHz, $CDCl_3$) δ 8.85 (s, 1H), 5.33 (s, 1H), 4.01 (m, 1H), 3.70 (m, 1H), 3.42 (m, 1H), 3.23 (m, 1H), 3.11 (m, 1H), 3.03 (m, 1H), 2.35 (m, 1H), 1.99-1.82 (m, 2H), 1.67-1.47 (m, 2H).

Step IV: Preparation of Compound 23e

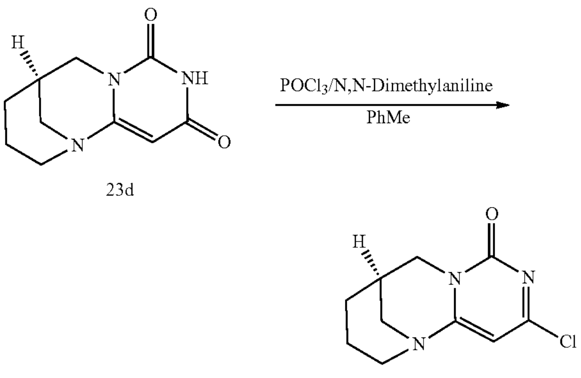

23d

23e

To a solution of compound 23d (0.5 g, 2.4 mmol) and dimethylaniline (0.29 g, 2.4 mmol) in toluene, was added phosphorous oxychloride (0.74 g, 4.8 mmol) dropwise at room temperature. The reaction mixture was heated to reflux for 4 h, quenched with ice water, and concentrated under reduced pressure. The residue was extracted with ethyl acetate (60 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with $CH_2Cl_2/CH_3OH$ (20/1) afforded the title compound 23e (0.31 g, 57.2%) as a white solid.

$^1H$ NMR (400 MHz, $CDCl_3$) δ 6.05 (s, 1H), 4.05 (m, 1H), 3.76 (m, 1H), 3.51 (m, 1H), 3.28 (m, 1H), 3.22-3.13 (m, 1H), 3.02 (m, 1H), 2.52 (m, 1H), 2.01-1.82 (m, 2H), 1.61-1.39 (m, 2H).

Step V: Preparation of Compound 23

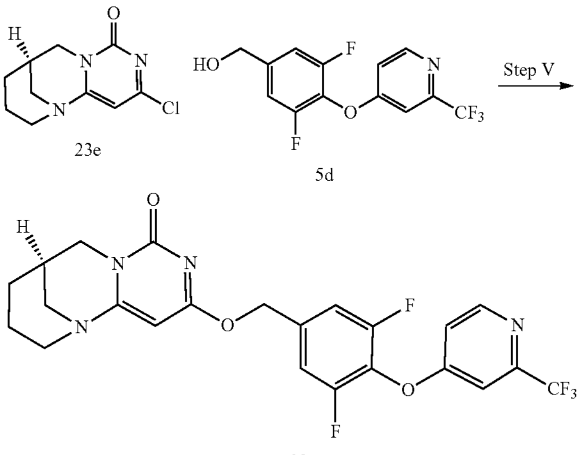

23e

5d

23

To a solution of (3,5-Difluoro-4-((2-(trifluoromethylpyridin-4-yl)oxy)phenyl)methanol 5d (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 23e (50 mg, 0.22 mmol). The reaction mixture was stirred for 1 h, quenched with a small amount of water. Purification on a silica gel column with dichloromethane/methanol (20/1) afforded the title compound 23 (25 mg, 23.0%) as a white solid.

$^1H$ NMR (400 MHz, $CDCl_3$) δ 8.59 (m, 1H), 7.25 (s, 1H), 7.14 (m, 2H), 6.98 (m, 1H), 5.63 (s, 1H), 5.42 (s, 2H), 4.07 (m, 1H), 3.79 (m, 1H), 3.46 (m, 1H), 3.26 (m, 1H), 3.15 (m, 1H), 3.04 (m, 1H), 2.44 (m, 1H), 2.00-1.84 (m, 2H), 1.56-1.46 (m, 2H). MS (ESI): m/z 495.1 $[M+H]^+$.

Example 24 Preparation of Compound 24

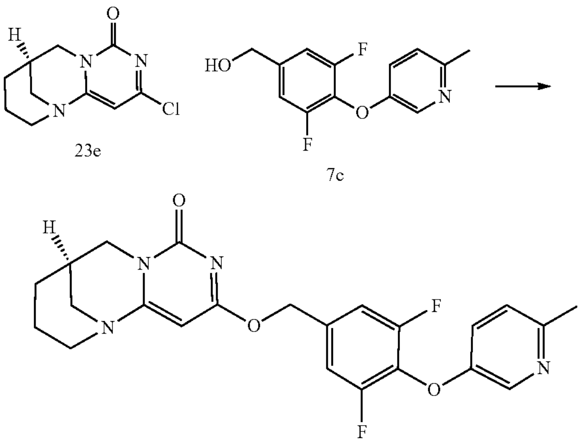
23e

7c

24

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 23e (50 mg, 0.22 mmol). The reaction mixture was stirred for 1 h, quenched with a small amount of water. Purification on a silica gel column with dichloromethane/methanol (20/1) afforded the title compound 24 (52 mg, 53.7%) as a white solid.

$^1H$ NMR (400 MHz, $CDCl_3$) δ 8.27 (m, 1H), 7.09 (m, 4H), 5.61 (s, 1H), 5.38 (s, 2H), 4.06 (m, 1H), 3.80 (m, 1H), 3.46 (m, 1H), 3.28-3.20 (m, 1H), 3.15 (m, 1H), 3.04 (m, 1H), 2.51 (s, 3H), 2.43 (m, 1H), 1.92 (m, 2H), 1.57-1.45 (m, 2H). MS (ESI): m/z 441.2 $[M+H]^+$.

Example 25 Preparation of Compound 25

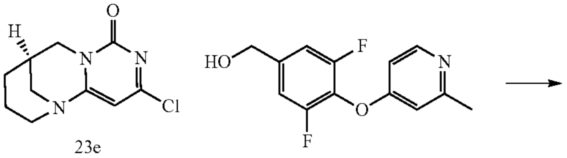
23e

6c

-continued

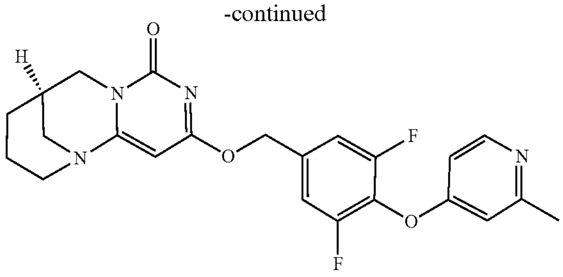

25

To a solution of (3,5-Difluoro-4-((2-methyl)pyridin-4-yl)oxy)phenyl)methanol 6c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 23e (50 mg, 0.22 mmol). The reaction mixture was stirred for 1 h, quenched with a small amount of water. Purification on a silica gel column with dichloromethane/methanol (20/1) afforded the title compound 25 (38 mg, 39.2%) as a white solid.

$^1$H NMR (400 MHz, $CDCl_3$) δ 8.36 (m, 1H), 7.11 (m, 2H), 6.67 (m, 2H), 5.63 (s, 1H), 5.41 (s, 2H), 4.07 (m, 1H), 3.80 (m, 1H), 3.47 (m, 1H), 3.32-3.21 (m, 1H), 3.15 (m, 1H), 3.04 (m, 1H), 2.51 (s, 3H), 2.44 (m, 1H), 2.00-1.83 (m, 2H), 1.59-1.46 (m, 2H). MS (ESI): m/z 441.2 $[M+H]^+$.

Example 26 Preparation of Compound 26

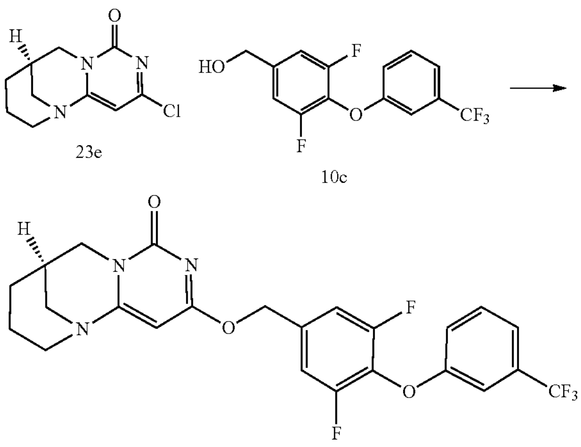

23e

10c

26

To a solution of (3,5-Difluoro-4-(3-(trifluoromethyl) phenoxy)phenyl)methanol 10c (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 23e (50 mg, 0.22 mmol). The reaction mixture was stirred for 1 h, quenched with a small amount of water. Purification on a silica gel column with dichloromethane/methanol (20/1) afforded the title compound 26 (58 mg, 53.4%) as a white solid.

$^1$H NMR (400 MHz, $CDCl_3$) δ 7.42 (m, 1H), 7.33 (m, 1H), 7.20 (s, 1H), 7.11 (m, 3H), 5.63 (s, 1H), 5.41 (s, 2H), 4.07 (m, 1H), 3.80 (m, 1H), 3.47 (m, 1H), 3.30-3.20 (m, 1H), 3.15 (m, 1H), 3.04 (m, 1H), 2.43 (m, 1H), 1.98-1.84 (m, 2H), 1.56-1.48 (m, 2H). MS (ESI): m/z 494.1 $[M+H]^+$.

Example 27 Preparation of Compound 27

27

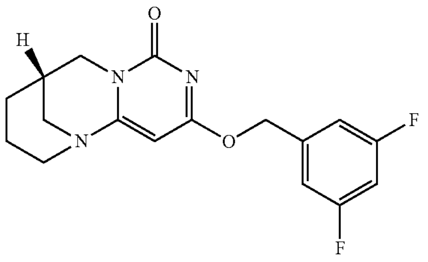

To a solution of 3,5-Difluorobenzyl alcohol (32 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 23e (50 mg, 0.22 mmol). The reaction mixture was stirred for 1 h, quenched with a small amount of water. Purification on a silica gel column with dichloromethane/methanol (20/1) afforded the title compound 27 (19 mg, 25.9%) as a white solid.

$^1$H NMR (400 MHz, $CDCl_3$) δ 6.96-6.87 (m, 2H), 6.73 (m, 1H), 5.58 (s, 1H), 5.37 (s, 2H), 4.05 (m, 1H), 3.79 (m, 1H), 3.45 (m, 1H), 3.29-3.19 (m, 1H), 3.14 (m, 1H), 3.03 (m, 1H), 2.41 (m, 1H), 1.98-1.82 (m, 2H), 1.55-1.46 (m, 2H). MS (ESI): m/z 334.1 $[M+H]^+$.

Example 28 Preparation of Compound 28

28

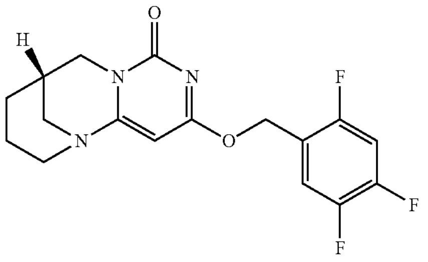

To a solution of 2,4,5-Trifluorobenzyl alcohol (36 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 23e (50 mg, 0.22 mmol). The reaction mixture was stirred for 1 h, quenched with a small amount of water. Purification on a silica gel column with dichloromethane/methanol (20/1) afforded the title compound 28 (18 mg, 23.3%) as a white solid.

$^1$H NMR (400 MHz, $CDCl_3$) δ 7.32 (m, 1H), 6.95 (m, 1H), 5.58 (s, 1H), 5.40 (s, 2H), 4.06 (m, 1H), 3.79 (m, 1H), 3.44 (m, 1H), 3.29-3.19 (m, 1H), 3.14 (m, 1H), 3.03 (m, 1H), 2.43 (m, 1H), 1.93 (m, 2H), 1.55-1.46 (m, 2H). MS (ESI): m/z 352.1 $[M+H]^+$.

Example 29 Preparation of Compound 29

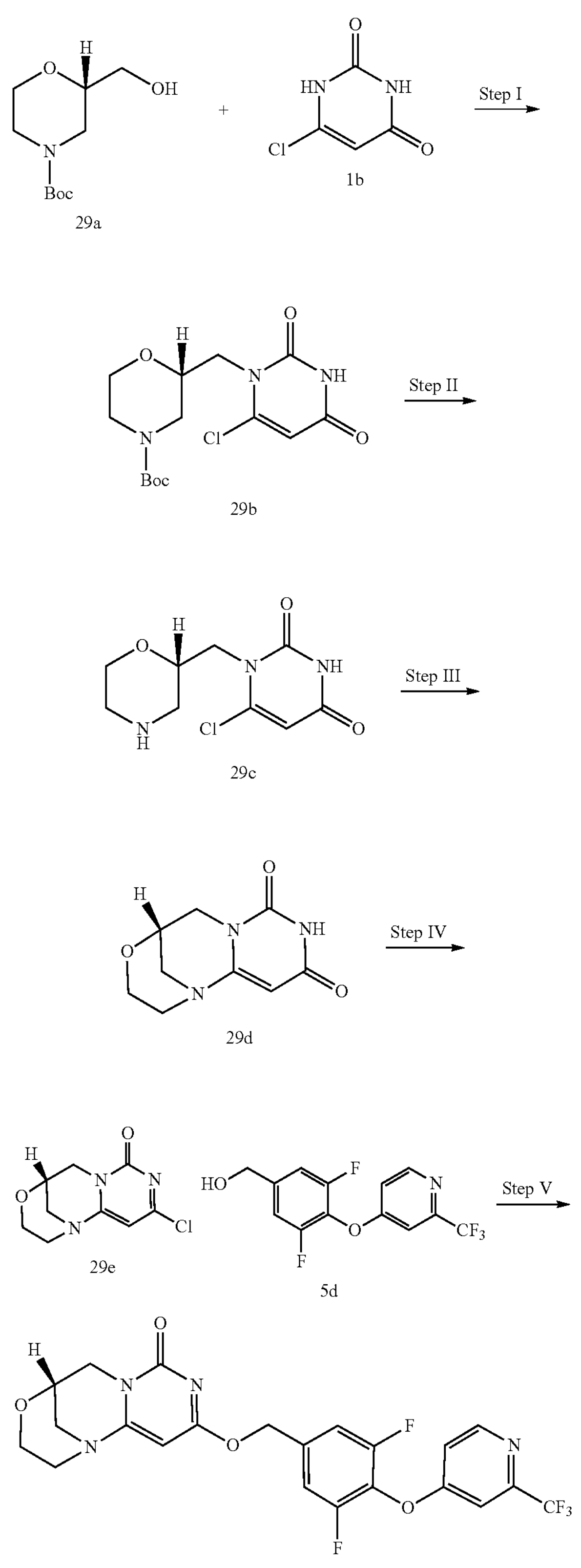

29a, 1b, 29b, 29c, 29d, 29e, 5d, 29

Step I: Preparation of Compound 29b

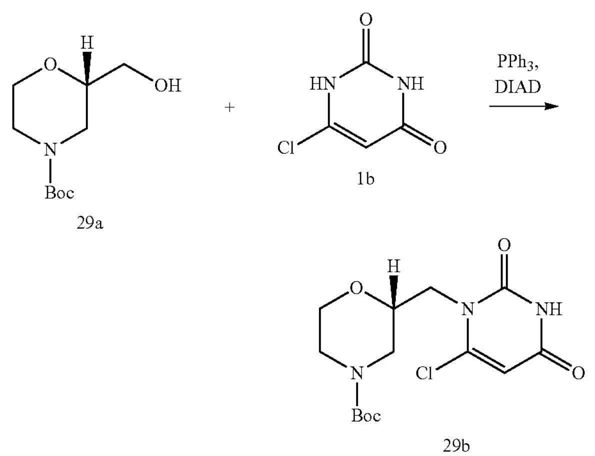

29a, 1b, 29b

To a solution of 6-chlorouracil 1b (10 g, 69 mmol), tert-butyl (S)-2-(hydroxymethyl) morpholine-4-carboxylate 29a (15 g, 69 mmol) and triphenylphosphine (27 g, 102.9 mmol) dissolved in a mixed solvent of anhydrous tetrahydrofuran (250 mL) and N,N-dimethylformamide (50 mL) at room temperature, was added dropwise diisopropyl azodicarboxylate (27 ml, 138 mmol) under nitrogen at 0° C. The reaction mixture was stirred at 0° C. for 2 h, then warmed to room temperature and stirred overnight. The reaction mixture was filtered and extracted with ethyl acetate (50 mL×3). The combined organic phases were washed with a saturated aqueous solution of sodium chloride, dried over anhydrous sodium sulfate, and concentrated under reduced pressure. Then the mixed solvent PE/EA=3/1 (100 ml) was added to the residue, and a large amount of a white solid precipitated. Filtered, and the filtrate was concentrated under reduced pressure. Purification on a silica gel column with $CH_2Cl_2$/$CH_3OH$ (20/1) afforded the title compound 29b (11.5 g, yield: 48.2%) as a colorless oil.

Steps II and III: Preparation of Compound 29d

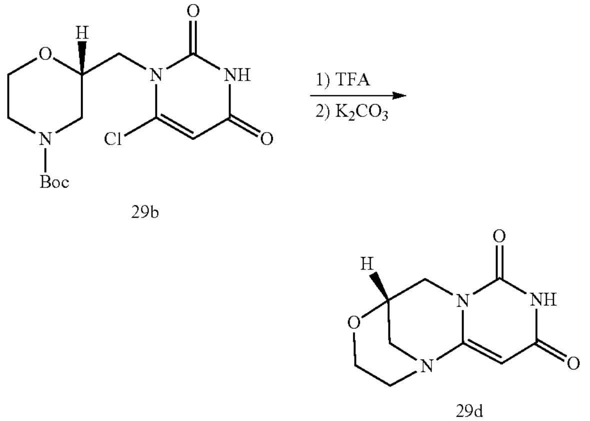

29b, 29d

To a solution of Tert-butyl (S)-2-((6-chloro-2,4-dioxo-3,4-dihydropyrimidin-1(2H)-yl)methyl) morpholine-4 carboxylate 29b (11.5 g, 33.2 mmol) dissolved in dichloromethane (80 mL) at room temperature, was added trifluoroacetic acid (10 mL) at 0° C. The reaction mixture was stirred at room temperature for 2 h, and concentrated under reduced pressure. The afforded residue was used directly in the next step, and dissolved in acetonitrile (80 mL), then potassium carbonate (9.2 g, 67 mmol) was added at room temperature. The reaction mixture was heated to reflux overnight, and filtrated, the filter cake was washed with acetonitrile and methanol, respectively. The filtrate was concentrated under reduced pressure, followed by purification on a silica gel column $CH_2Cl_2/CH_3OH$ (20/1) to afford the title compound 29d (1.9 g, 27.4%) as a white solid.

$^1H$ NMR (400 MHz, $CDCl_3$) δ 9.39 (s, 1H), 5.41 (s, 1H), 4.36-4.28 (m, 1H), 4.05 (m, 1H), 3.95 (m, 1H), 3.78 (m, 1H), 3.69-3.55 (m, 2H), 3.44-3.37 (m, 1H), 3.24 (m, 1H), 2.96 (m, 1H).

Step IV: Preparation of Compound 29e

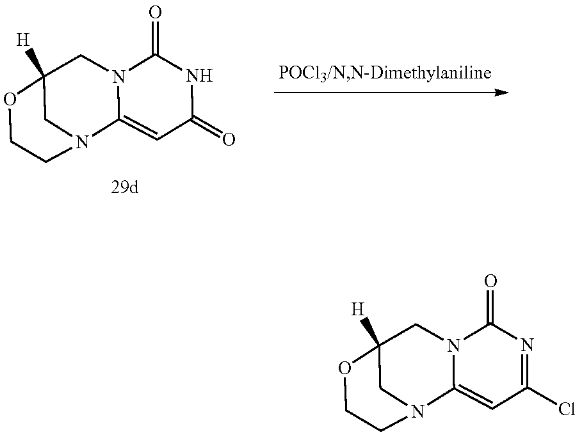

29d

29e

To a solution of compound 29d (0.5 g, 2.4 mmol) and dimethylaniline (0.29 g, 2.4 mmol) in toluene, was added phosphorous oxychloride (0.73 g, 4.8 mmol) dropwise at room temperature. The reaction mixture was heated to reflux for 4 h, quenched with ice water, and concentrated under reduced pressure. The residue was extracted with ethyl acetate (60 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with $CH_2Cl_2/CH_3OH$ (20/1) afforded the title compound 29e (0.3 g, 54.9%) as a white solid.

$^1H$ NMR (400 MHz, $CDCl_3$) δ 6.12 (s, 1H), 4.49 (m, 1H), 4.08 (m, 1H), 3.99 (m, 1H), 3.72-3.61 (m, 3H), 3.48 (m, 1H), 3.37 (m, 1H), 2.96 (m, 1H).

Step V: Preparation of Compound 29

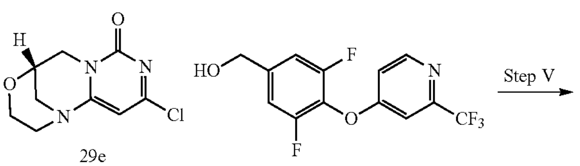

29e

5d

-continued

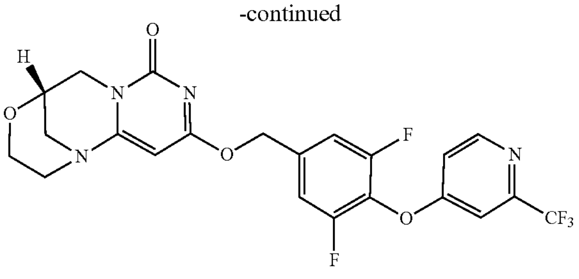

29

To a solution of (3,5-Difluoro-4-((2-(trifluoromethylpyridin-4-yl)oxy)phenyl)methanol 5d (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 29e (50 mg, 0.22 mmol). The reaction mixture was stirred for 1 h, quenched with a small amount of water. Purification on a silica gel column with dichloromethane/methanol (20/1) afforded the title compound 29 (31 mg, 28.4%) as a white solid.

$^1H$ NMR (400 MHz, $CDCl_3$) δ 8.59 (m, 1H), 7.25 (s, 1H), 7.14 (m, 2H), 6.98 (m, 1H), 5.69 (s, 1H), 5.43 (s, 2H), 4.40 (m, 1H), 4.12 (m, 1H), 4.03 (m, 1H), 3.70-3.57 (m, 3H), 3.44 (m, 1H), 3.27 (m, 1H), 2.95 (m, 1H). MS (ESI): m/z 497.1 $[M+H]^+$,

Example 30 Preparation of Compound 30

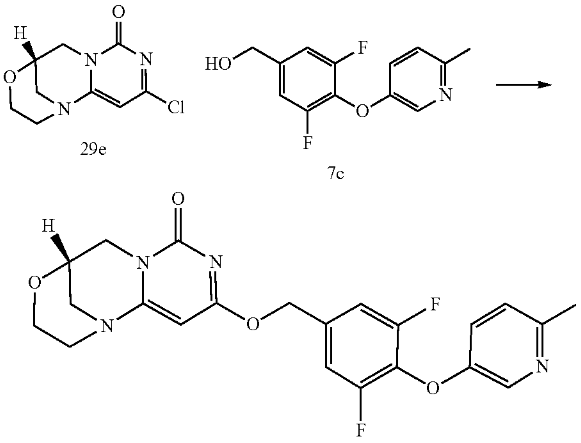

29e

7c

30

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 29e (50 mg, 0.22 mmol). The reaction mixture was stirred for 1 h, quenched with a small amount of water. Purification on a silica gel column with dichloromethane/methanol (20/1) afforded the title compound 30 (49 mg, 50.3%) as a white solid.

$^1H$ NMR (400 MHz, $CDCl_3$) δ 8.26 (m, 1H), 7.16-7.05 (m, 4H), 5.69 (s, 1H), 5.40 (s, 2H), 4.40 (m, 1H), 4.13 (m,

1H), 4.04 (m, 1H), 3.70-3.58 (m, 3H), 3.45 (m, 1H), 3.27 (m, 1H), 2.96 (m, 1H), 2.52 (s, 3H). MS (ESI): m/z 443.1 $[M+H]^+$.

Example 31 Preparation of Compound 31

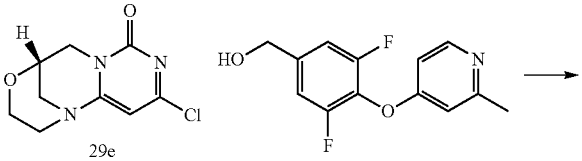

29e

6c

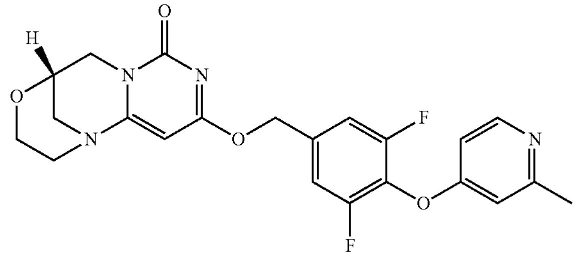

30

To a solution of (3,5-Difluoro-4-((2-methyl)pyridin-4-yl) oxy)phenyl)methanol 6c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 29e (50 mg, 0.22 mmol). The reaction mixture was stirred for 1 h, quenched with a small amount of water. Purification on a silica gel column with dichloromethane/methanol (20/1) afforded the title compound 31 (38 mg, 39.0%) as a white solid.

$^1H$ NMR (400 MHz, $CDCl_3$) δ 8.35 (m, 1H), 7.11 (m, 2H), 6.72-6.63 (m, 2H), 5.70 (s, 1H), 5.42 (s, 2H), 4.39 (m, 1H), 4.17-4.08 (m, 1H), 4.03 (m, 1H), 3.71-3.57 (m, 3H), 3.50-3.40 (m, 1H), 3.27 (m, 1H), 2.95 (m, 1H), 2.50 (s, 3H). MS (ESI): m/z 443.1 $[M+H]^+$.

Example 32 Preparation of Compound 32

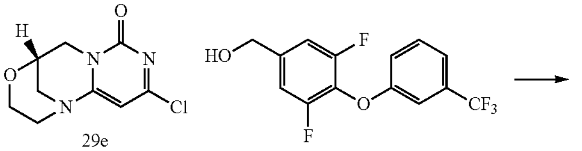

29e

10c

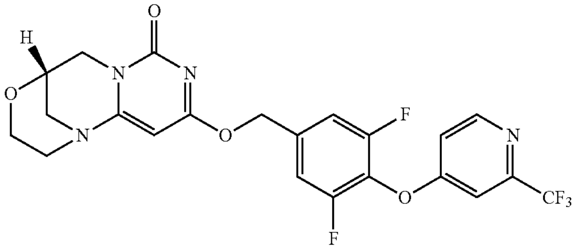

32

To a solution of (3,5-Difluoro-4-(3-(trifluoromethyl) phenoxy)phenyl)methanol 10c (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 29e (50 mg, 0.22 mmol). The reaction mixture was stirred for 1 h, quenched with a small amount of water. Purification on a silica gel column with dichloromethane/methanol (20/1) afforded the title compound 32 (31 mg, 28.4%) as a white solid.

$^1H$ NMR (400 MHz, $CDCl_3$) δ 7.42 (m, 1H), 7.34 (m, 1H), 7.19 (s, 1H), 7.10 (m, 3H), 5.70 (s, 1H), 5.42 (s, 2H), 4.40 (m, 1H), 4.17-4.00 (m, 2H), 3.71-3.57 (m, 3H), 3.45 (m, 1H), 3.28 (m, 1H), 2.96 (m, 1H). MS (ESI): m/z 496.1 $[M+H]^+$.

Example 33 Preparation of Compound 33

33

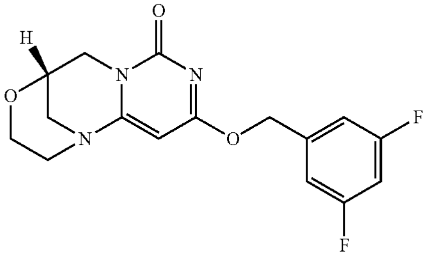

To a solution of 3,5-Difluorobenzyl alcohol (32 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 29e (50 mg, 0.22 mmol). The reaction mixture was stirred for 1 h, quenched with a small amount of water. Purification on a silica gel column with dichloromethane/methanol (20/1) afforded the title compound 33 (21 mg, 28.5%) as a white solid.

$^1H$ NMR (400 MHz, $CDCl_3$) δ 6.98-6.91 (m, 2H), 6.77 (m, 1H), 5.70 (s, 1H), 5.40 (s, 2H), 4.41 (m, 1H), 4.14 (m, 1H), 4.04 (m, 1H), 3.72-3.58 (m, 3H), 3.46 (m, 1H), 3.28 (m, 1H), 2.97 (m, 1H). MS (ESI): m/z 336.1 $[M+H]^+$.

Example 34 Preparation of Compound 34

34

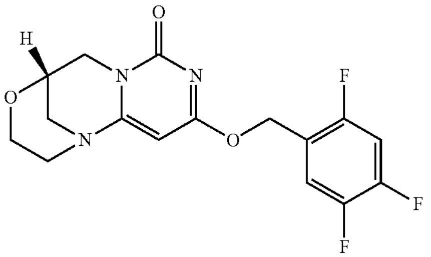

To a solution of 2,4,5-Trifluorobenzyl alcohol (36 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 29e (50 mg, 0.22 mmol).

The reaction mixture was stirred for 1 h, quenched with a small amount of water. Purification on a silica gel column with dichloromethane/methanol (20/1) afforded the title compound 34 (29 mg, 37.3%) as a white solid.

$^1$H NMR (400 MHz, $CDCl_3$) δ 7.36-7.27 (m, 1H), 6.95 (m, 1H), 5.64 (s, 1H), 5.40 (s, 2H), 4.42-4.35 (m, 1H), 4.12 (m, 1H), 4.02 (m, 1H), 3.73-3.55 (m, 3H), 3.43 (m, 1H), 3.24 (m, 1H), 2.95 (m, 1H). MS (ESI): m/z 354.1 [M+H]$^+$.

Example 35 Preparation of Compound 35

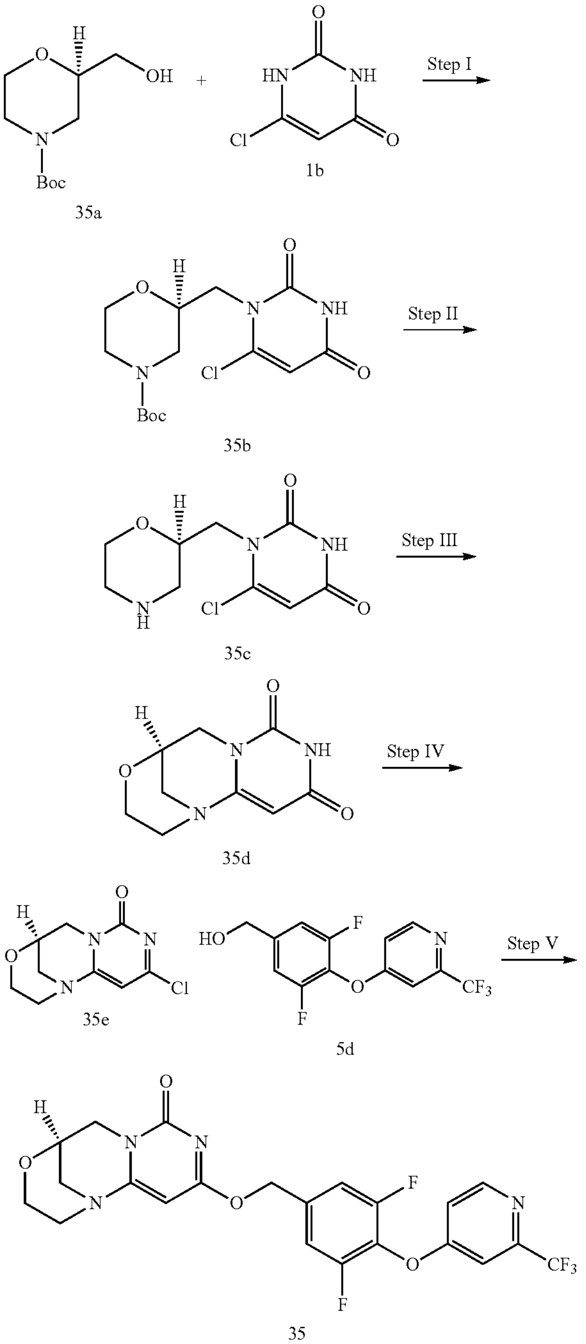

35a 1b 35b 35c 35d 35e 5d 35

Step I: Preparation of Compound 35b:

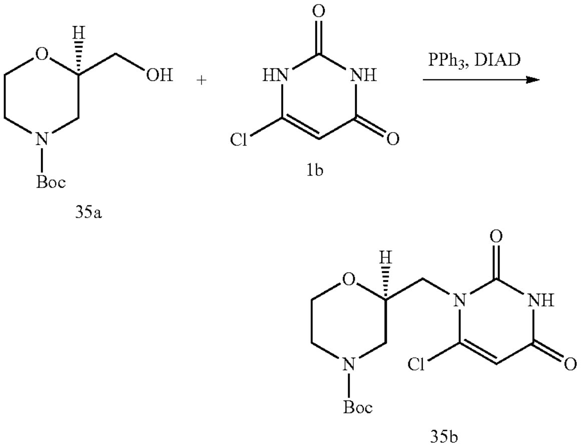

35a 1b 35b

To a solution of 6-chlorouracil 1b (10 g, 69 mmol), tert-butyl (R)-2-(hydroxymethyl) morpholine-4-carboxylate 35a (15 g, 69 mmol) and triphenylphosphine (27 g, 102.9 mmol) dissolved in a mixed solvent of anhydrous tetrahydrofuran (250 mL) and N,N-dimethylformamide (50 mL) at room temperature, was added dropwise diisopropyl azodicarboxylate (27 ml, 138 mmol) under nitrogen at 0° C. The reaction mixture was stirred at 0° C. for 2 h, then warmed to room temperature and stirred overnight. The reaction mixture was filtered and extracted with ethyl acetate (50 mL×3). The combined organic phases were washed with a saturated aqueous solution of sodium chloride, dried over anhydrous sodium sulfate, and concentrated under reduced pressure. Then the mixed solvent PE/EA=3/1 (100 ml) was added to the residue, and a large amount of a white solid precipitated. Filtered and the filtrate was concentrated under reduced pressure. Purification on a silica gel column with $CH_2Cl_2$/$CH_3OH$ (20/1) afforded the title compound 35b (7.2 g, yield: 30.5%) as a colorless oil.

Steps II and III: Preparation of Compound 35d

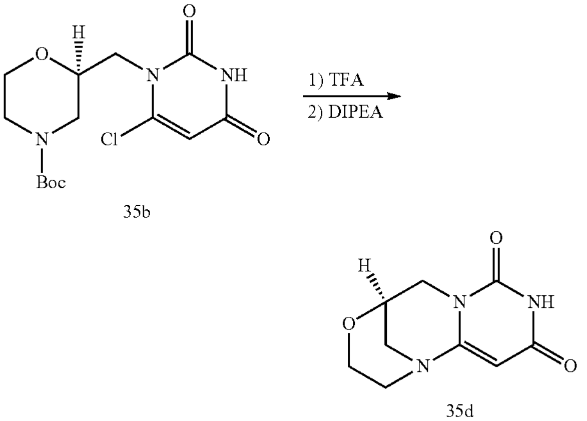

35b 35d

To a solution of Tert-butyl (R)-2-((6-chloro-2,4-dioxo-3,4 dihydropyrimidin-1(2H)-yl)methyl) morpholine-4-carboxylate 35b (7.2 g, 20.8 mmol) dissolved in dichloromethane (80 mL) at room temperature, was added trifluoroacetic acid (10 mL) at 0° C. The reaction mixture was stirred at room temperature for 2 h, and concentrated under reduced pressure. The afforded residue was used directly in the next step, and dissolved in acetonitrile (80 mL), then diisopropylethylamine (8.1 g, 62.7 mmol) was added at room temperature. The reaction mixture was stirred at room temperature for 4 h, and concentrated under reduced pressure, followed by purification on a silica gel column $CH_2Cl_2/CH_3OH$ (20/1) to afford the title compound 35d (2.5 g, 57.4%) as a white solid.

$^1$H NMR (400 MHz, $CDCl_3$) δ 9.32 (s, 1H), 5.42 (s, 1H), 4.35-4.29 (m, 1H), 4.07 (m, 1H), 3.96 (m, 1H), 3.78 (m, 1H), 3.70-3.55 (m, 2H), 3.45-3.36 (m, 1H), 3.24 (m, 1H), 2.96 (m, 1H).

Step IV: Preparation of Compound 35e

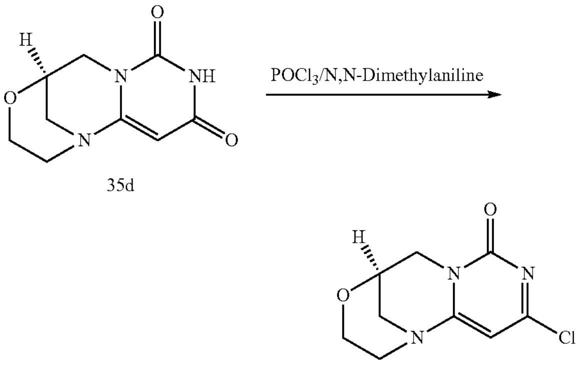

35d

35e

To a solution of compound 35d (0.1 g, 0.48 mmol) and dimethylaniline (0.06 g, 0.48 mmol) in toluene, was added phosphorous oxychloride (0.73 g, 4.8 mmol) dropwise at room temperature. The reaction mixture was heated to reflux for 4 h, quenched with ice water, and concentrated under reduced pressure. The residue was extracted with ethyl acetate (60 mL×3). The combined organic phases were washed with a saturated aqueous solution of sodium chloride and dried over anhydrous sodium sulfate, the desiccant was filtered out and the filtrate was concentrated under reduced pressure. Purification on a silica gel column with $CH_2Cl_2$/$CH_3OH$ (20/1) afforded the title compound 35e (0.04 g, 36.4%) as a white solid.

$^1$H NMR (400 MHz, $CDCl_3$) δ 6.12 (s, 1H), 4.48 (m, 1H), 4.06 (m, 1H), 3.99 (m, 1H), 3.73-3.61 (m, 3H), 3.47 (m, 1H), 3.42-3.32 (m, 1H), 2.96 (m, 1H).

Step V: Preparation of Compound 35

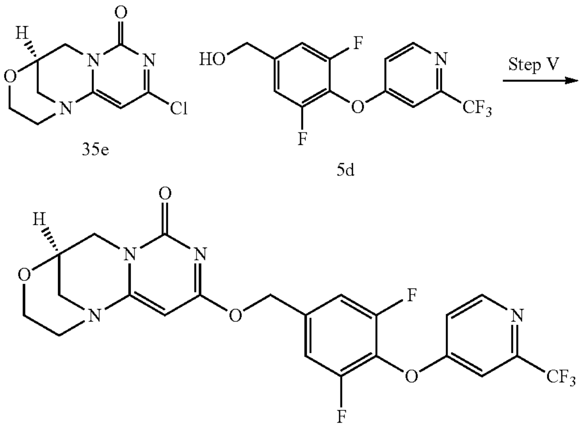

35e

5d

35

To a solution of (3,5-Difluoro-4-((2-(trifluoromethylpyridin-4-yl)oxy)phenyl)methanol 5d (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 35e (50 mg, 0.22 mmol). The reaction mixture was stirred for 1 h, quenched with a small amount of water. Purification on a silica gel column with dichloromethane/methanol (20/1) afforded the title compound 35 (41 mg, 37.5%) as a white solid.

$^1$H NMR (400 MHz, $CDCl_3$) δ 8.60 (m, 1H), 7.25 (s, 1H), 7.15 (m, 2H), 6.99 (m, 1H), 5.70 (s, 1H), 5.44 (s, 2H), 4.40 (m, 1H), 4.13 (m, 1H), 4.04 (m, 1H), 3.70-3.58 (m, 3H), 3.44 (m, 1H), 3.28 (m, 1H), 2.96 (m, 1H). MS (ESI): m/z 497.1 $[M+H]^+$.

Example 36 Preparation of Compound 36

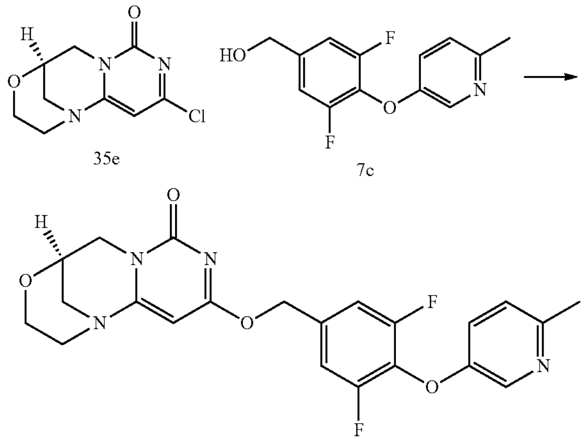

35e

7c

36

To a solution of (3,5-Difluoro-4-((6-methylpyridin-3-yl)oxy)phenyl)methanol 7c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 35e (50 mg, 0.22 mmol). The reaction mixture was stirred for 1 h, quenched with a small amount of water. Purification on a silica gel column with dichloromethane/methanol (20/1) afforded the title compound 36 (42 mg, 43.2%) as a white solid.

$^1$H NMR (400 MHz, $CDCl_3$) δ 8.21 (m, 1H), 7.06 (m, 4H), 5.65 (s, 1H), 5.37 (s, 2H), 4.36 (m, 1H), 4.13-4.03 (m, 1H), 3.98 (m, 1H), 3.66-3.53 (m, 3H), 3.40 (m, 1H), 3.23 (m, 1H), 2.93 (m, 1H), 2.47 (s, 3H). MS (ESI): m/z 443.1 $[M+H]^+$.

Example 37 Preparation of Compound 37

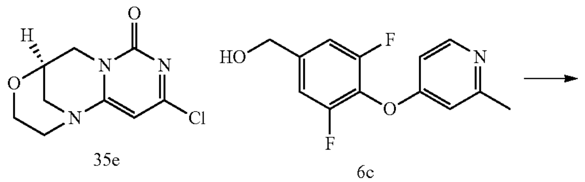

35e

6c

-continued

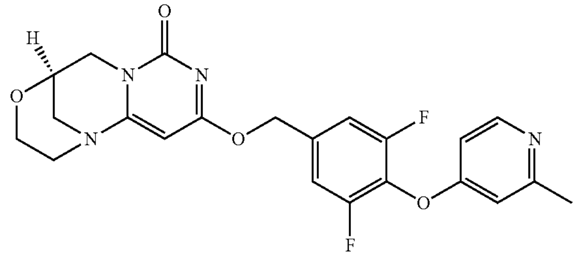

37

To a solution of (3,5-Difluoro-4-((2-methyl)pyridin-4-yl)oxy)phenyl)methanol 6c (56 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 35e (50 mg, 0.22 mmol). The reaction mixture was stirred for 1 h, quenched with a small amount of water. Purification on a silica gel column with dichloromethane/methanol (20/1) afforded the title compound 37 (18 mg, 18.5%) as a white solid.

$^1$H NMR (400 MHz, $CDCl_3$) δ 8.36 (m, 1H), 7.09 (m, 2H), 6.70-6.65 (m, 2H), 5.70 (s, 1H), 5.43 (s, 2H), 4.41 (m, 1H), 4.13 (m, 1H), 4.04 (m, 1H), 3.72-3.58 (m, 3H), 3.46 (m, 1H), 3.28 (m, 1H), 2.96 (m, 1H), 2.51 (s, 3H). MS (ESI): m/z 443.1 $[M+H]^+$.

Example 38 Preparation of Compound 38

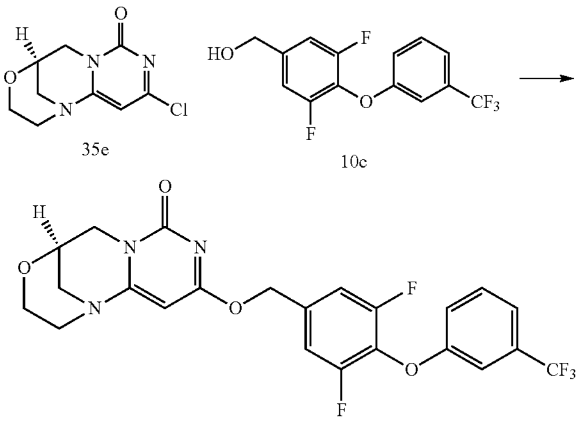

35e

10c

38

To a solution of (3,5-Difluoro-4-(3-(trifluoromethyl)phenoxy)phenyl)methanol 10c (67 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 35e (50 mg, 0.22 mmol). The reaction mixture was stirred for 1 h, quenched with a small amount of water. Purification on a silica gel column with dichloromethane/methanol (20/1) afforded the title compound 38 (55 mg, 50.5%) as a white solid.

$^1$H NMR (400 MHz, $CDCl_3$) δ 7.41 (m, 1H), 7.33 (m, 1H), 7.18 (s, 1H), 7.10 (m, 3H), 5.70 (s, 1H), 5.41 (s, 2H), 4.40 (m, 1H), 4.15-4.07 (m, 1H), 4.03 (m, 1H), 3.70-3.55 (m, 3H), 3.45 (m, 1H), 3.27 (m, 1H), 2.96 (m, 1H). MS (ESI): m/z 496.1 $[M+H]^+$.

Example 39 Preparation of Compound 39

39

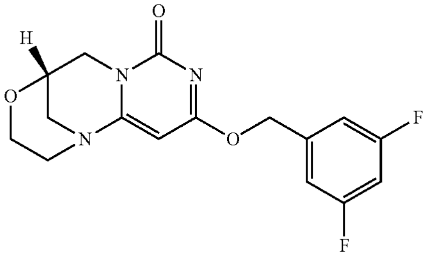

To a solution of 3,5-Difluorobenzyl alcohol (32 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 35e (50 mg, 0.22 mmol). The reaction mixture was stirred for 1 h, quenched with a small amount of water. Purification on a silica gel column with dichloromethane/methanol (20/1) afforded the title compound 39 (37 mg, 50.2%) as a white solid.

$^1$H NMR (400 MHz, $CDCl_3$) δ 6.96-6.89 (m, 2H), 6.75 (m, 1H), 5.68 (s, 1H), 5.39 (s, 2H), 4.40 (m, 1H), 4.12 (m, 1H), 4.03 (m, 1H), 3.70-3.55 (m, 3H), 3.44 (m, 1H), 3.26 (m, 1H), 2.95 (m, 1H). MS (ESI): m/z 336.1 $[M+H]^+$.

Example 40 Preparation of Compound 40

40

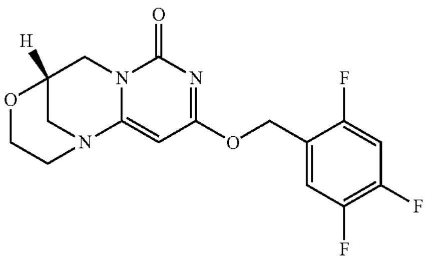

To a solution of 2,4,5-Trifluorobenzyl alcohol (36 mg, 0.22 mmol) in dry N,N-dimethylformamide (5 mL) was added sodium hydride (60% in mineral oil, 11 mg, 0.26 mmol) at 0° C., and stirred for 5 min at room temperature, followed by addition of compound 35e (50 mg, 0.22 mmol). The reaction mixture was stirred for 1 h, quenched with a small amount of water. Purification on a silica gel column with dichloromethane/methanol (20/1) afforded the title compound 40 (39 mg, 50.2%) as a white solid.

$^1$H NMR (400 MHz, $CDCl_3$) δ 7.36-7.28 (m, 1H), 6.95 (m, 1H), 5.65 (s, 1H), 5.41 (s, 2H), 4.42-4.35 (m, 1H), 4.17-4.08 (m, 1H), 4.03 (m, 1H), 3.71-3.55 (m, 3H), 3.44 (m, 1H), 3.25 (m, 1H), 2.95 (m, 1H). MS (ESI): m/z 354.1 $[M+H]^+$.

Biological Evaluation

The bioactivity of a compound could be determined using any suitable assay as well as tissue and in vivo model for determining the activity of a compound as an LpPLA2 inhibitor.

(1) Recombinant Human Lp-PLA2 (rhLp-PLA2) Assay (Also Known as PED6 Assay)

PED6 is a fluorescently labeled phospholipid, which could be purchased directly from Invitogene or Molecular Probes. PED6 has a fluorescence quenching p-nitrophenyl group at the Sn3 position and a Bodipy fluorescein (FL) group at the sn2 position. Once cleaved by an Lp-PLA2 enzyme, it will release the FL group, resulting in enhanced fluorescence. An Lp-PLA2 inhibitor can prevent such cleavage so that no fluorescence enhancement is observed.

Assay Method: The compound to be tested (as shown in Table 1) was mixed with a DMSO solution in a volume ratio of 1:3, and diluted to prepare a source plate of a 384-well microplate. Then 0.01 µl of the compound was transferred via an ECHO liquid dispenser from the source plate to a 384-well Greiner 784076 plate, and 5 µl of a buffer consisting of 50 mM HEPES, pH7.4, 150 mM NaCl, and 1 mM CHAPS (the buffer solution containing a recombinant human Lp-PLA2 enzyme at a concentration of 4 nM or 110 pM) was added to each well of the plate. The plate was centrifuged at 500 rpm for 10 seconds. After a 30-min pre-incubation, 5 µl of the above-mentioned buffer was added to a 384-well Greiner 784076 plate, the plate was centrifuged at 500 rpm for 10 seconds. After the plate was incubated at room temperature for 20 min in a dark place, the fluorescence intensity was read at ex 480/em 540 with a ViewLux microplate imager, and the XL fitting model in Excel was used to perform the curve analysis and QC analysis to calculate pIC50. The results were listed in Table 1.

TABLE 1

| Compound No. | rhLp-PLA2 ($pIC_{50}$) |
|---|---|
| 1 | 8.7 |
| 2 | 8.6 |
| 3 | 7.5 |
| 4 | 8.5 |
| 5 | 10.5 |
| 6 | 10.2 |
| 7 | 10.1 |
| 8 | 9.5 |
| 9 | 10.0 |
| 10 | 9.9 |
| 11 | 10.1 |
| 12 | 9.5 |
| 13 | 10.2 |
| 14 | 10.4 |
| 15 | 9.7 |
| 16 | 10.1 |
| 18 | 10.1 |
| 20 | 10.5 |
| 21 | 8.5 |
| 22 | 7.5 |
| 24 | 10.0 |
| 26 | 10.4 |
| 27 | 8.5 |
| 28 | 7.4 |
| 30 | 9.8 |
| 33 | 8.4 |
| 34 | 7.2 |
| 36 | 9.9 |
| 39 | 8.4 |
| 40 | 7.3 |
| Positive Compound Rilapladib | 8.9 |

(2) Human Plasma Lp-PLA2 Assay (Also Known as Thio-PAF Assay)

The human plasma assay was conducted using the sulphatide analog of PAF (phosphatidylcholine). After hydrolysis, it would generate phospholipids containing free sulfhydryl groups, which would be subjected to Michael addition with CPM to generate fluorescence-enhancing maleimide. Continuous quantitative analysis of thiol could be conducted by detecting the fluorescence intensity. This assay can be used to detect the inhibitory activity of the Lp-PLA2 inhibitor on the Lp-PLA2 enzyme in human plasma.

Assay Method: The compound to be tested (as shown in Table 2) was mixed with a DMSO solution in a volume ratio of (1:3), and diluted to prepare a source plate of a 384-well microplate. Then 0.01 µl of the compound was transferred via an ECHO liquid dispenser from the source plate to a 384-well Greiner 784076 low-volume plate, and 8 µl of pre-aliquoted and frozen mixed human plasma was then added. The plate was centrifuged at 500 rpm for 10 seconds. After a 30-min pre-incubation, 2 µl of a substrate solution, and a buffer containing 2.5 mM 2-thio-PAF (a solution in ethanol), 32 µM CPM (a solution in DMSO) and 3.2 mM N-ethylmaleimide (NEM) (a buffer solution consisting of 50 mM HEPES, pH7.4, 150 mM NaCl, 1 mM CHAPS) was added by a BRAVO liquid handling station to a 384-well Greiner 784076 low-volume plate. Two minutes later, the reaction was quenched with 5 µl of 5% trifluoroacetic acid. After the plate was incubated at room temperature for 40 min in a dark place, the fluorescence intensity was read at ex 380/em 485 with an Envision microplate reader, and the XL fitting model in Excel was used to perform the curve analysis and QC analysis to calculate pIC50. The results are shown in Table 2.

TABLE 2

| Compound No. | Thio-PAF ($pIC_{50}$) |
|---|---|
| 1 | 7.5 |
| 2 | 7.5 |
| 3 | 6.5 |
| 4 | 7.4 |
| 5 | 8.5 |
| 6 | 8.2 |
| 7 | 8.1 |
| 8 | 7.8 |
| 9 | 8.0 |
| 10 | 8.0 |
| 11 | 8.1 |
| 12 | 7.8 |
| 13 | 8.1 |
| 14 | 8.2 |
| 15 | 7.9 |
| 16 | 8.1 |
| 18 | 8.1 |
| 20 | 8.5 |
| 21 | 7.4 |
| 22 | 6.5 |
| 24 | 8.1 |
| 26 | 8.4 |
| 27 | 7.3 |
| 28 | 6.5 |
| 30 | 8.0 |
| 33 | 7.1 |
| 34 | 6.3 |
| 36 | 7.9 |
| 39 | 7.0 |
| 40 | 6.3 |
| Positive compound Rilapladib | 7.8 |

What is claimed is:

1. A compound of Formula (I) or a pharmaceutically acceptable salt thereof, (I)

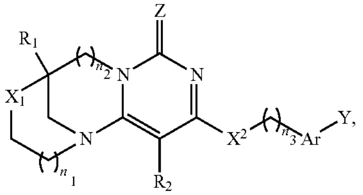

wherein $n_1$, $n_2$, and $n_3$ are each independently 0, 1, or 2;

$R_1$ and $R_2$ are each independently selected from the group consisting of —H, hydroxyl, cyano, halogen, alkyl, deuterated alkyl, deuterated alkoxy, hydroxyalkyl, haloalkyl, haloalkoxy, cycloalkyl, alkoxy, arylene, or heteroarylene;

$X_1$ and $X_2$ are each independently selected from the group consisting of alkylene, —O—, —S—, or —NR'—, R' is selected from the group consisting of —H, alkyl, deuterated alkyl, or cycloalkyl;

Ar is arylene or heteroarylene, wherein hydrogens in the arylene or heteroarylene are each optionally substituted with one or more substituents, and the substituents are each independently selected from the group consisting of halogen, alkyl, deuteroalkyl, haloalkyl, alkoxy, deuteroalkoxy, haloalkoxy, hydroxy, hydroxyalkyl, cyano, amino, monoalkyl- or dialkyl-substituted amino, nitro, carboxy, formyl, cycloalkyl, heterocyclyl, aryl, or heteroaryl;

Y is selected from the group consisting of —H, halogen, alkyl, haloalkyl, haloalkoxy, cycloalkyl, alkoxy, deuterated alkyl, deuterated alkoxy, hydroxy, hydroxyalkyl, cyano, arylene, heteroarylene, —OAr', —SAr', —NR''—Ar', —NR''R'', or —R'''—Ar';

Ar' is aryl or heteroaryl, wherein hydrogens in the aryl or heteroaryl are optionally substituted with one or more substituents, the substituents are each independently selected from the group consisting of halogen, alkyl, haloalkyl, alkoxy, hydroxy, hydroxyalkyl, haloalkoxy, deuterated alkyl, deuterated alkoxy, cyano, amino, nitro, carboxy, formyl, cycloalkyl, heterocyclyl, aryl, or heteroaryl;

R'' is H—, alkyl, or cycloalkyl;

R''' is alkylene;

Z is O or S.

2. The compound or a salt thereof according to claim 1, wherein halogens in the "halogen" "haloalkyl" and "haloalkoxy" are each independently selected from the group consisting of F, Cl, Br, or I;

optionally, alkyls in the "alkyl" "deuterated alkyl" "deuterated alkoxy" "hydroxyalkyl" "haloalkyl", "haloalkoxy" "alkoxy" and "mono- or di-alkyl substituted amino" are each independently $C_1$-$C_{10}$ linear or branched alkyl; optionally each independently $C_1$-$C_7$ linear or branched alkyl; optionally each independently $C_1$-$C_4$ linear or branched alkyl; and optionally selected from the group consisting of methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, or 2,2,3-trimethylbutyl;

optionally, "alkylenes" are each independently $C_1$-$C_{10}$ linear or branched alkylene; optionally each $C_1$-$C_7$ linear or branched alkylene; optionally each $C_1$-$C_5$ linear or branched alkylene; and optionally each selected from the group consisting of methylene, ethylene, n-propylene, iso-propylene, n-butylene, isobutylene, tert-butylene, sec-butylene, n-pentylene, 1-methylbutylene, 2-methylbutylene, 3-methylbutylene, isopentylene, 1-ethylpropylene, neopentylene, n-hexylene, 1-methylpentylene, 2-methylpentylene, 3-methylpentylene, isohexylene, 1,1-dimethylbutylene, 2,2-dimethylbutylene, 3,3-dimethylbutylene, 1,2-dimethylbutylene, 1,3-dimethylbutylene, 2,3-dimethylbutylene, 2-ethylbutylene, n-heptylene, 2-methylhexylene, 3-methylhexylene, 2,2-dimethylpentylene, 3,3-dimethylpentylene, 2,3-dimethylpentylene, 2,4-dimethylpentylene, 3-ethylpentylene, or 2,2,3-trimethylbutylene;

optionally, "cycloalkyl" is $C_3$-$C_{10}$ monocyclic or bicyclic cycloalkyl, optionally $C_3$-$C_7$ monocyclic cycloalkyl, and optionally cyclopropyl, cyclobutyl, cyclopentyl, cyclohexyl, or cycloheptyl;

optionally, "heterocyclyl" is 3- to 10-membered non-aromatic heterocycle having in the ring 1, 2, or 3 heteroatoms selected from the group consisting of N, O, and S; optionally 3- to 10-membered non-aromatic ring having in the ring 1 or 2 heteroatoms selected from the group consisting of N and O; optionally 3- to 6-membered non-aromatic ring having in the ring 1 or 2 heteroatoms selected from the group consisting of N and O; optionally 3- to 10-membered non-aromatic ring having in the ring 1 or 2 heteroatoms selected from the group consisting of N and S; and optionally 3- to 6-membered non-aromatic ring having in the ring 1 or 2 heteroatoms selected from the group consisting of N and S;

optionally, "aryl" is 6- to 10-membered aryl; optionally phenyl or naphthyl, and optionally phenyl, 1-naphthyl, or 2-naphthyl;

optionally, "arylene" is 6- to 10-membered arylene; and optionally phenylene or naphthylene;

optionally, "heteroaryl" is 5- to 10-membered heteroaryl ring having in the ring 1-3 heteroatoms selected from the group consisting of N, O, and S; optionally 5- to 10-membered heteroaryl ring having in the ring 1-2 heteroatoms selected from the group consisting of N, O, and S; optionally the heteroaryl ring is selected from the group consisting of pyridine ring, pyrrole ring, pyrazole ring, pyrimidine ring, pyrazine ring, pyridazine ring, thiophene ring, and furan ring; optionally selected from pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, pyrazin-3-yl, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinoxalinyl, thieno[2,3-b]furanyl, furo[3,2-b]-pyranyl, pyrido[2,3-d]oxazinyl, pyrazolo[4,3-d]oxazolyl, imidazo[4,5-d]thiazolyl, pyrazino[2,3-d]pyridazinyl, imidazo[2,1-b]thiazolyl, imidazo[1,2-b][1,2,4]triazinyl, benzothienyl, benzoxazolyl, benzimidazolyl, benzothiazolyl, benzoxepinyl, benzoxazinyl, benzofuranyl, benzotriazolyl, pyrrolo[2,3-b]pyridyl, pyrrolo[3,2-c]pyridinyl, pyrrolo[3,2-b]pyridyl, imidazo[4,5-b]pyridyl, imidazo[4,5-c]

pyridyl, pyrazolo[4,3-d]pyridyl, pyrazolo[4,3-c]pyridyl, pyrazolo[3,4-c]pyridinyl, pyrazolo[3,4-d]pyridyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazolo[2,3-b]pyrazinyl, or pyrimido[4,5-d]pyrimidinyl; and is optionally selected from pyridin-2-yl, pyridin-3-yl, pyridin-4-yl, pyrimidin-2-yl, pyrimidin-4-yl, or pyrimidin-5-yl;

optionally, "heteroarylene" is 5- to 10-membered heteroarylene ring having in the ring 1-3 heteroatoms selected from the group consisting of N, O, and S; optionally 5- to 10-membered heteroaromatic ring having in the ring 1-2 heteroatoms selected from the group consisting of N, O, and S; and optionally the heteroarylene ring is selected from the group consisting of pyridinylene ring, pyrrolylene ring, pyrazolylene ring, pyrimidinylene ring, pyrazine ring, pyridazine ring, thiophene ring, or furanylene ring;

optionally, the compound of Formula (I) is in the form of a tautomer, meso isomer, racemate, enantiomer, diastereomer, or mixture thereof.

3. The compound or a salt thereof according to claim 1, wherein $n_1$, $n_2$, and $n_3$ are each independently 0, 1, or 2; optionally, $n_1$ is 1; optionally, $n_2$ is 1; optionally, $n_3$ is 1;

optionally, $R_1$ and $R_2$ are each independently selected from the group consisting of —H, fluorine, chlorine, bromine, iodine, hydroxyl, hydroxyalkyl, cyano, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, $—CD_3$, $—C_2D_5$, $—C_3D_7$, $—OCD_3$, $—OC_2D_5$, $—OC_3D_7$, $—CF_3$, $—CHF_2$, $—CH_2F$, $—C_2F_5$, $—C_3F_7$, $C_1$-$C_7$ haloalkoxy, $C_1$-$C_7$ alkoxy, cyclopropanyl, cyclobutanyl, cyclopentanyl, or cyclohexanyl; optionally, $R_1$ is —H; and optionally, $R_2$ is —H;

optionally, $X_1$ and $X_2$ are each independently selected from the group consisting of $C_1$-$C_7$ alkylene, —O—, —S—, or —NR'—; optionally, $X_1$ is $—CH_2—$, ethylene, n-propylene, isopropylene, n-butylene, or isobutylene, —O—, or —S—; optionally, $X_1$ is $C_1$-$C_7$ alkylene or —O—; optionally, $X_1$ is $—CH_2—$ or —O—; optionally, $X_2$ is —O— or —S—; and optionally, $X_2$ is —O—;

optionally, R' is selected from the group consisting of —H, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, $—CD_3$, $—C_2D_5$, $—C_3D_7$, cyclopropanyl, cyclobutanyl, cyclopentanyl, or cyclohexanyl;

optionally, Ar is phenylene or pyridyl, wherein hydrogen atoms in the phenylene or pyridyl are optionally substituted with 1, 2, or 3 substituents, the substituents are each independently selected from the group consisting of F, Cl, Br, I, —CN, -Me, $—CF_3$, $—CHF_2$, $—C_2H_5$, $—C_3H_7$, cyclopropyl, cyclobutyl, cyclopentyl, cyclohexyl, $—CD_3$, $—OCD_3$, —OMe, $—OCF_3$, or $—OCHF_2$;

optionally, Ar is arylene; and optionally, Ar is phenylene, wherein hydrogen atoms in the phenylene are optionally substituted with one or two substituents, the substituents are halogen, and optionally F;

optionally, Y is selected from the group consisting of —H, —F, —Cl, —Br, —I, methyl, ethyl, n-propyl, isopropyl, $—CD_3$, $—OCD_3$, $—CF_3$, $—CHF_2$, $—CH_2F$, $—CH_2CF_3$, $—OCF_3$, $—OCHF_2$, $—OCH_2F$, cyclopropyl, cyclobutyl, cyclopentyl, cyclohexyl, $—OCH_3$, $—OC_2H_5$, $—OC_3H_7$, or —OAr';

optionally, Y is H, halogen, or —OAr'; and optionally, Y is H, —F, or —OAr';

optionally, Ar' is selected from the group consisting of phenyl, pyridyl, pyrimidinyl, thienyl, pyrrolyl, pyrazolyl, or quinolinyl, wherein hydrogen atoms in the phenyl, pyridyl, pyrimidinyl, thienyl, pyrrolyl, pyrazolyl, or quinolinyl ring are each independently optionally substituted with 1, 2, or 3 substituents, the substituents are each independently selected from the group consisting of F, Cl, Br, methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl, 2,2,3-trimethylbutyl, $—CD_3$, $—OCD_3$, $C_1$-$C_6$ haloalkyl, $—OCH_3$, $—OCH_7$, $—OC_3H_7$, $C_1$-$C_6$ haloalkoxy, hydroxyl, hydroxyalkyl, cyano, cyclopropanyl, cyclobutanyl, cyclopentanyl, or cyclohexanyl;

optionally, Ar' is selected from the group consisting of phenyl, pyridin-3-yl, pyridin-4-yl, or pyrimidin-5-yl, and is optionally substituted with 1 or 2 substituents, the substituents is selected from halogen, alkyl, haloalkyl, or haloalkoxy, and optionally selected from F, Cl, $—CH_3$, $—CF_3$, or $—OCF_3$;

optionally, Z is O or S; and optionally, Z is O.

4. The compound of Formula (I) or a pharmaceutically acceptable salt thereof according to claim 1, wherein the compound of Formula (I) is selected from the group consisting of the following compounds:

1

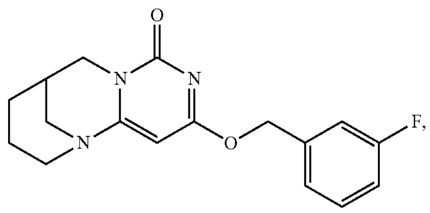

-continued
2
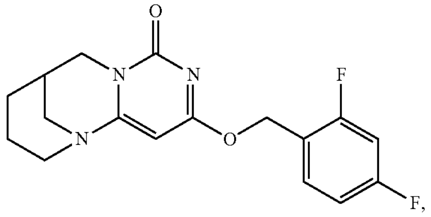
3
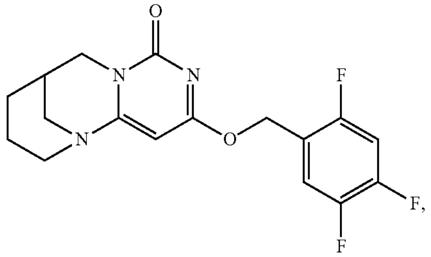
4
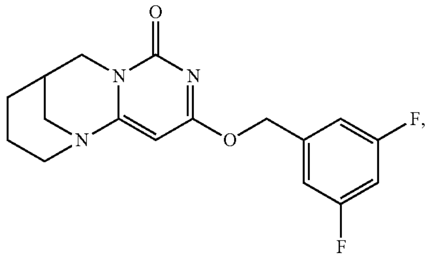
5
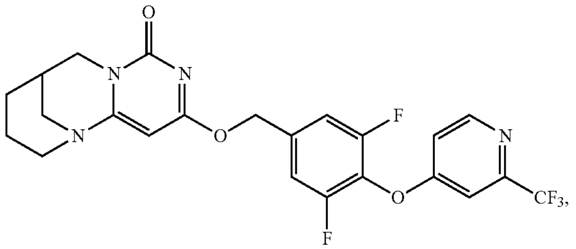
6
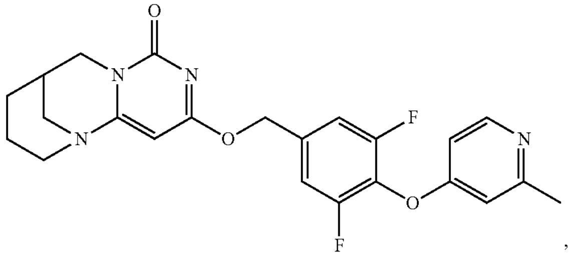
,
7
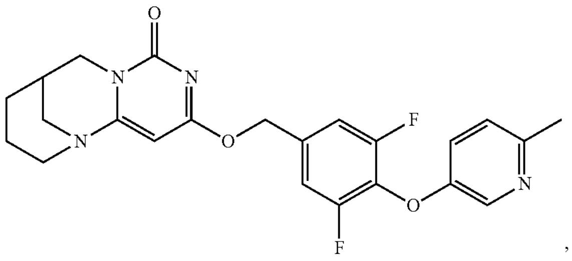
,
-continued
8
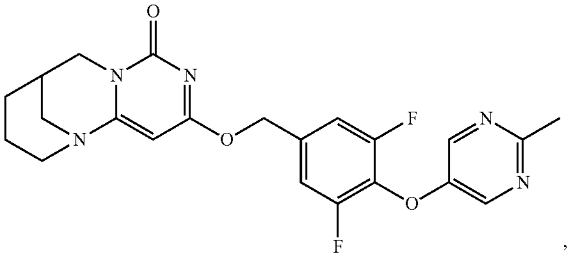
,
9
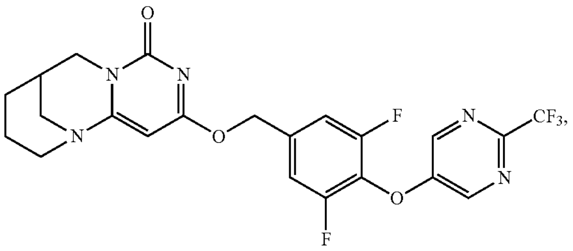
10
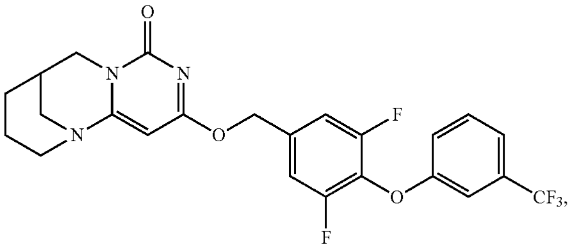
11
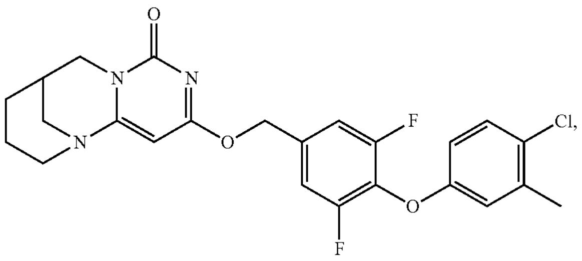
12
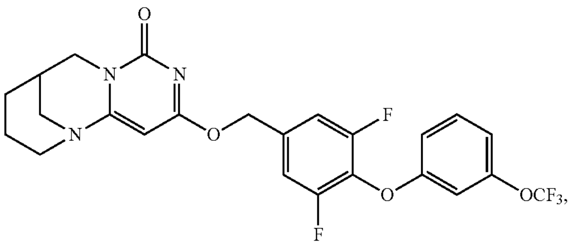

-continued
13
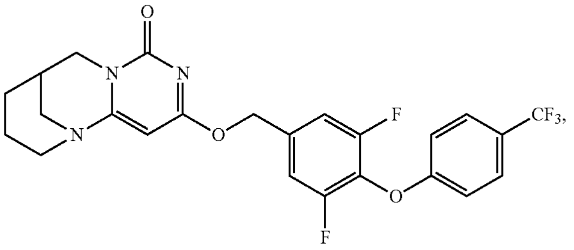
14
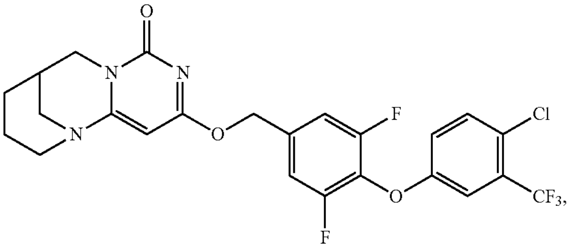
15
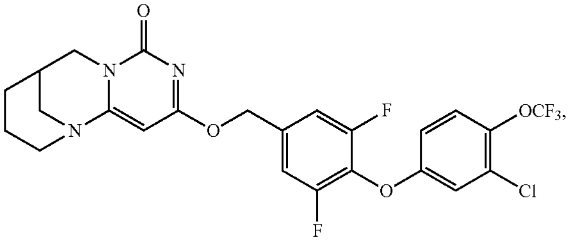
16
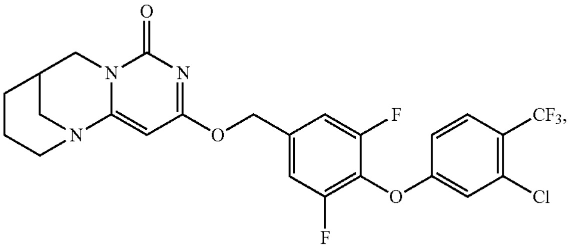
17
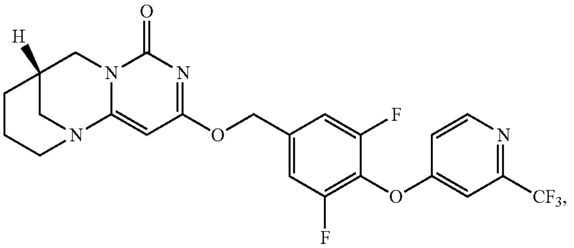
18
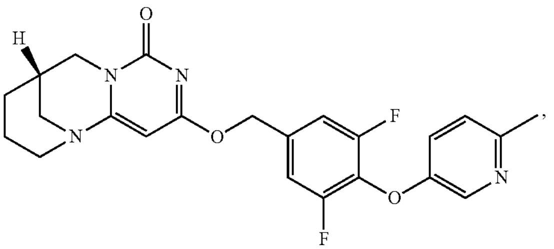
-continued
19
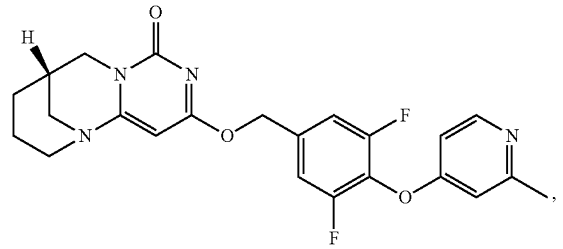
20
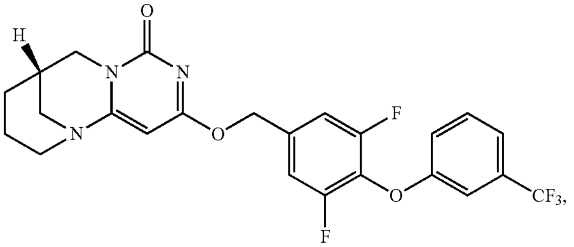
21
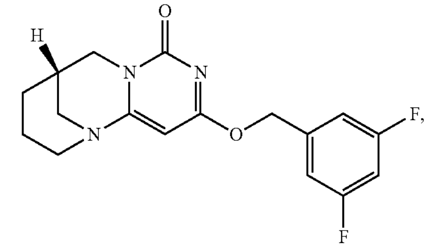
22
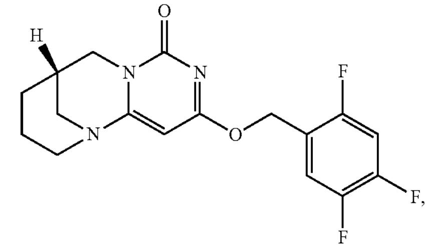
23
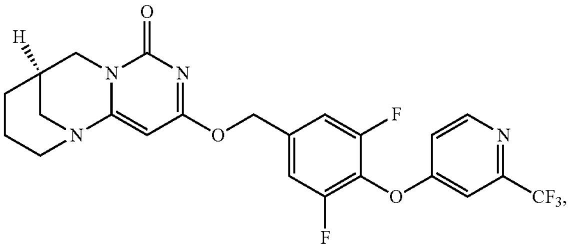
24
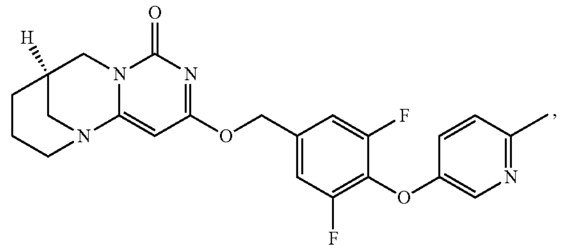

25
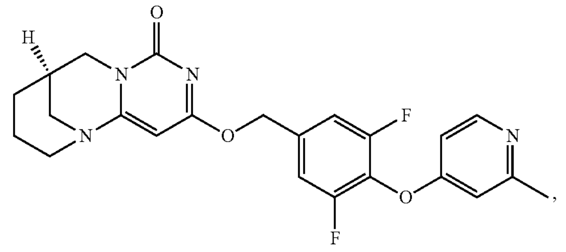
26
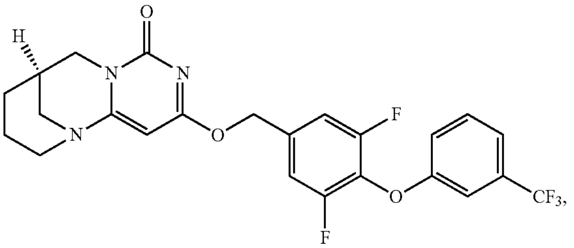
27
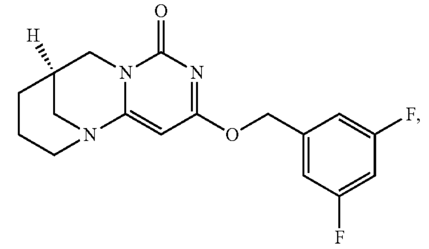
28
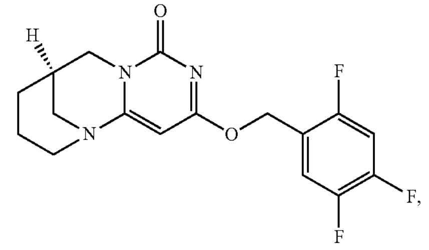
29
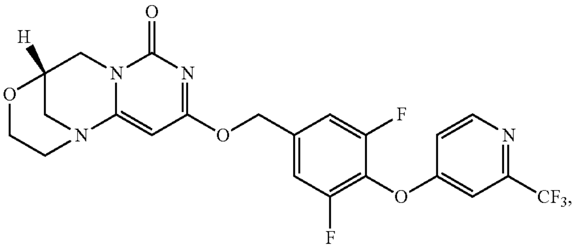
30
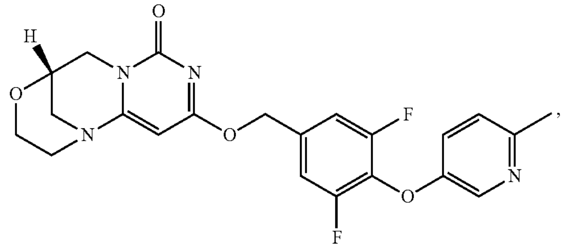
31
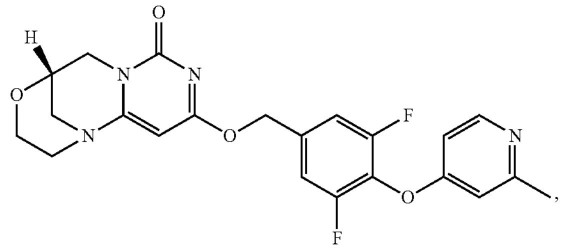
32
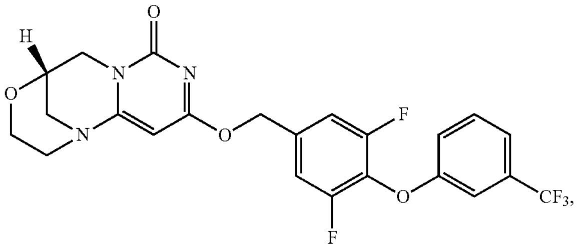
33
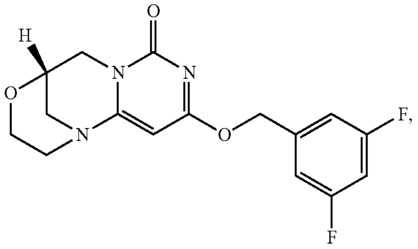
34
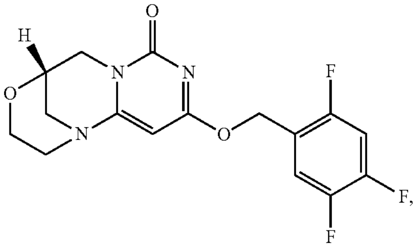
35
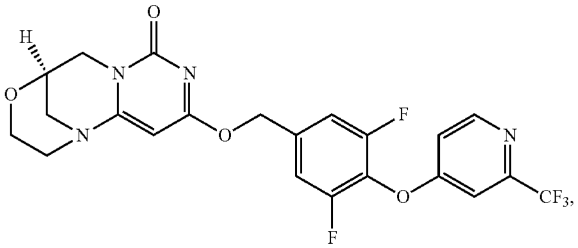
36
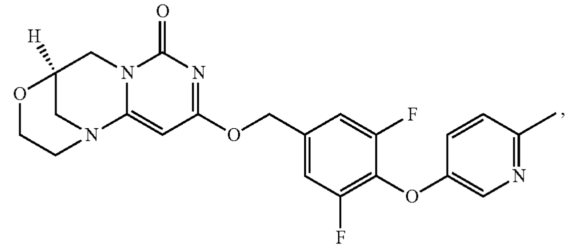

-continued

37

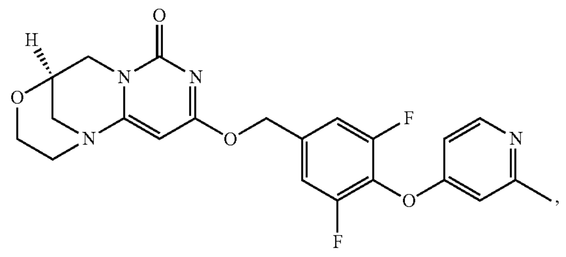

38

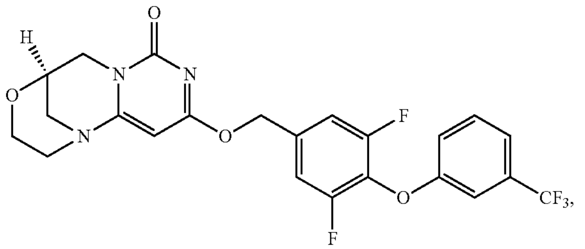

39

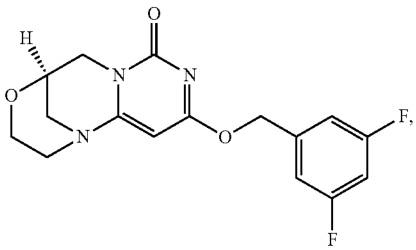

40

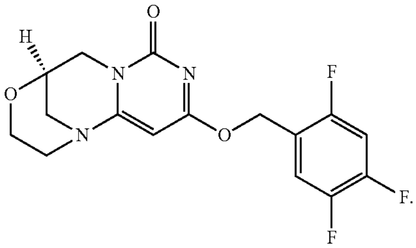

5. The compound of Formula (I) or a pharmaceutically acceptable salt thereof according to claim 1, wherein the pharmaceutically acceptable salt includes an anionic salt or cationic salt of the compound of Formula (I);

optionally, the pharmaceutically acceptable salt includes alkali metal salt, alkaline earth metal salt, or ammonium salt of the compound of Formula (I); optionally, the alkali metal includes sodium, potassium, lithium, or cesium, and the alkaline earth metal includes magnesium, calcium, or strontium;

optionally, the pharmaceutically acceptable salt includes salt formed by the compound of Formula (I) and an organic base;

optionally, the organic base includes trialkylamine, pyridine, quinoline, piperidine, imidazole, picoline, dimethylaminopyridine, dimethylaniline, N-alkylmorpholine, 1,5-diazabicyclo[4.3.0]nonene-5, 1,8-diazabicyclo[5.4.0]undecene-7, 1,4-diazabicyclo[2.2.2]octane; optionally, the trialkylamine includes trimethylamine, triethylamine, or N-ethyldiisopropylamine; and optionally, the N-alkyl morpholine includes N-methylmorpholine;

optionally, the pharmaceutically acceptable salt includes salt formed by the compound of Formula (I) and an acid;

optionally, the acid includes inorganic acid, or organic acid; optionally, the inorganic acid includes hydrochloric acid, hydrobromic acid, hydroiodic acid, sulfuric acid, nitric acid, phosphoric acid, or carbonic acid; optionally, the organic acid includes formic acid, acetic acid, propionic acid, oxalic acid, malonic acid, succinic acid, fumaric acid, maleic acid, lactic acid, malic acid, citric acid, citric acid, tartaric acid, carbonic acid, picric acid, methanesulfonic acid, ethanesulfonic acid, p-toluenesulfonic acid, glutamic acid, or pamoic acid.

6. A preparation method of the compound of Formula (I) or a pharmaceutically acceptable salt thereof according to claim 1, comprising the step of reacting a compound of Formula (II) with a compound of Formula (III) to produce the compound of Formula (I):

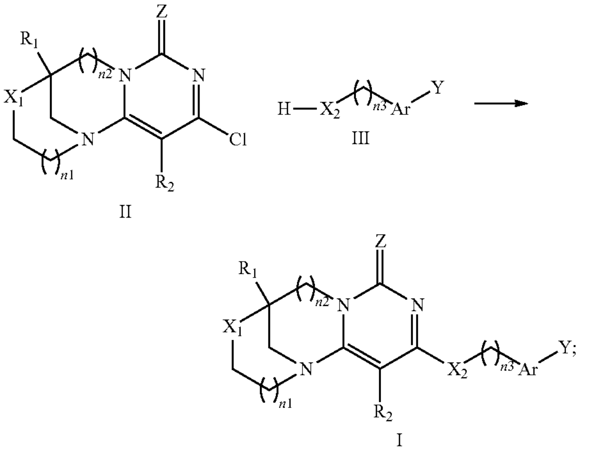

optionally, the preparation method comprises the step of reacting a compound of Formula (IV) with phosphorus oxychloride to produce the compound of Formula (II):

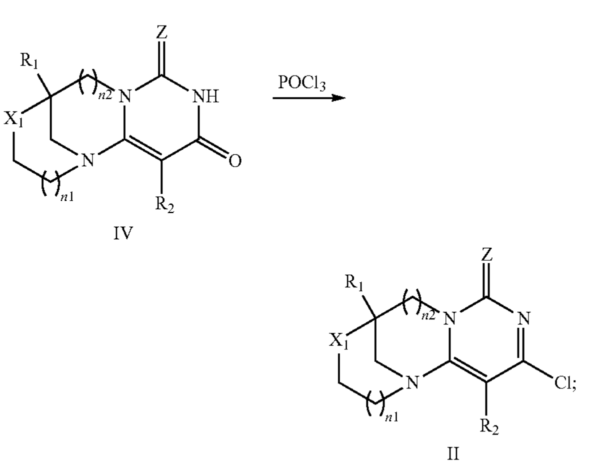

optionally, the preparation method comprises the step of subjecting a compound of Formula (V) to cyclization reaction to produce the compound of Formula (IV):

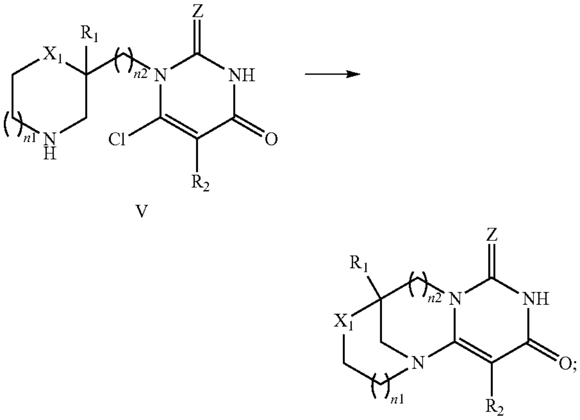

V

IV optionally, the preparation method comprises the step of reacting a compound of Formula (VII) with a compound of Formula (VIII) to produce a compound of Formula (VI), and further removing the protective group from the compound of Formula (VI) to produce the compound of Formula (V):

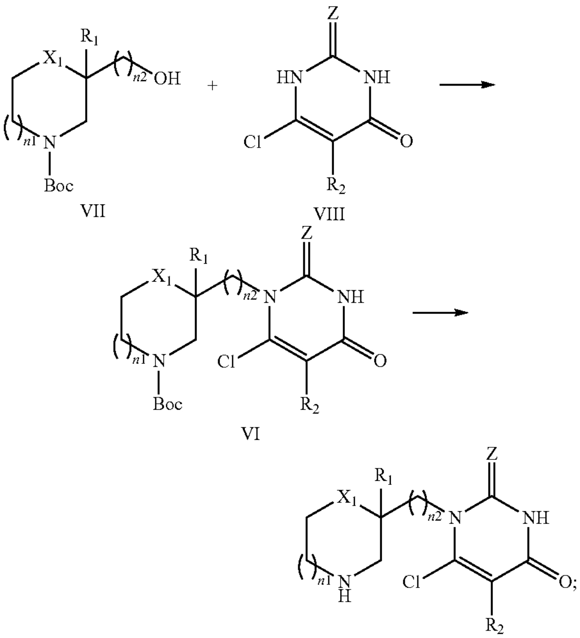

VII

VIII

VI

V optionally, the preparation method includes the following reaction scheme:

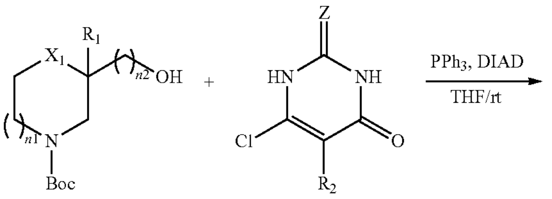

-continued

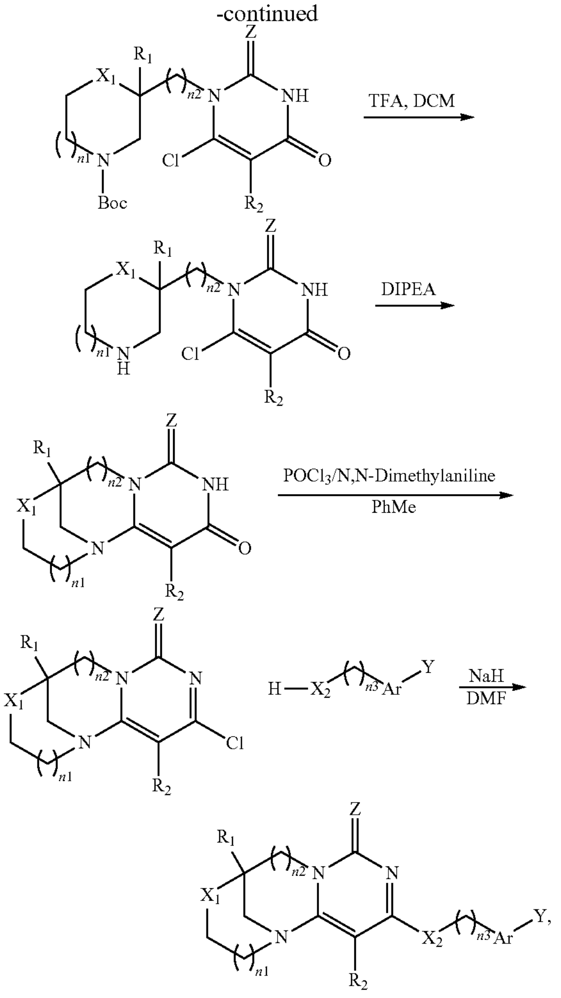

wherein in each of the formulas, $n_1$, $n_2$, $n_3$, $R_1$, $R_2$, $X_1$, $X_2$, Z, Ar, and Y are defined as in claim 1.

7. A pharmaceutical composition, comprising a therapeutically effective amount of one or more of the compound of Formula (I) or a pharmaceutically acceptable salt thereof according to claim 1, and optionally, pharmaceutically acceptable excipient(s).

8. The pharmaceutical composition according to claim 7, wherein the dosage form of the pharmaceutical composition includes oral, rectal, or parenteral formulation;

optionally, the oral formulation includes solid or liquid formulation;

optionally, the solid formulation includes tablet, powder, granule, or capsule;

optionally, the liquid formulation includes aqueous or oily suspension, or syrup;

optionally, the parenteral formulation includes solution for injection, or aqueous or oily suspension.

9. A method for treatment of Alzheimer's disease, comprising administering to a subject in need thereof an amount of a compound of Formula (I) or a pharmaceutically acceptable salt thereof according to claim 1 effective to treat or alleviate Alzheimer's disease.

10. A method for treatment of diabetic macular edema or atherosclerosis, comprising administering to a subject in need thereof an amount of a compound of Formula (I) or a pharmaceutically acceptable salt thereof according to claim 1 effective to treat or alleviate diabetic macular edema or atherosclerosis.

* * * * *